United States Patent [19]

Cook et al.

[11] 4,091,209
[45] * May 23, 1978

[54] 7β-[2-ETHERIFIED OXIMINO-2-(PHENYL OR NAPHTHYLACETAMIDO)]CEPHALOSPORINS HAVING A 2-HALOALKYLCARBAMOYLOXYMETHYL GROUP AT THE 3-POSITION

[75] Inventors: Martin Christopher Cook, Liverpool; Gordan Ian Gregory, Chalfont St. Peter; Janice Bradshaw, Harrow, all of England

[73] Assignee: Glaxo Laboratories Limited, Greenford, England

[*] Notice: The portion of the term of this patent subsequent to Aug. 10, 1993, has been disclaimed.

[21] Appl. No.: 762,942

[22] Filed: Jan. 26, 1977

Related U.S. Application Data

[60] Division of Ser. No. 587,065, Jun. 16, 1975, Pat. No. 4,024,137, which is a division of Ser. No. 304,524, Nov. 7, 1972, Pat. No. 3,971,778, which is a continuation-in-part of Ser. No. 252,666, May 12, 1972, abandoned.

[30] Foreign Application Priority Data

May 14, 1971 United Kingdom ............... 15082/71
Oct. 1, 1971 United Kingdom ............... 45884/71
Oct. 25, 1972 United Kingdom ............... 49255/72

[51] Int. Cl.² .......................................... C07D 501/20
[52] U.S. Cl. ...................................... 544/16; 424/246
[58] Field of Search ...................... 260/243 C; 544/16

[56] References Cited

U.S. PATENT DOCUMENTS

| 3,966,717 | 6/1976 | Cook et al. | 260/243 C |
| 3,971,778 | 7/1976 | Cook et al. | 260/243 C |
| 3,974,153 | 8/1976 | Cook et al. | 260/243 C |
| 4,007,174 | 2/1977 | Laundon | 260/243 C |
| 4,024,137 | 5/1977 | Cook et al. | 260/243 C |
| 4,033,950 | 7/1977 | Cook et al. | 260/243 C |

Primary Examiner—Nicholas S. Rizzo
Attorney, Agent, or Firm—Bacon & Thomas

[57] ABSTRACT

The invention provides novel antibiotic compounds which are 7β-acylamidoceph-3-em-4-carboxylic acids, and non-toxic derivatives thereof characterized in that the acylamido group has the structure

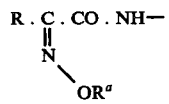

where R is a hydrogen atom or an organic group and $R^a$ is an etherifying monovalent organic group linked to the oxygen atom through a carbon atom. The compounds are syn isomers or exist as mixtures containing at least 75% of the syn isomer. These antibiotic compounds possess high antibacterial activity against a range of gram positive and gram negative organisms coupled with particularly high stability to β-lactamases produced by various gram negative organisms. The invention is also concerned with the administration of the compounds.

2 Claims, No Drawings

7β-[2-ETHERIFIED OXIMINO-2-(PHENYL OR NAPHTHYLACETAMIDO)]CEPHALOSPORINS HAVING A 2-HALOALKYLCARBAMOYLOXYMETHYL GROUP AT THE 3-POSITION

CROSS REFERENCE TO RELATED APPLICATION

This is a division of application Ser. No. 587,065, filed June 16, 1975, now U.S. Pat. No. 4,024,137, which is in turn a division of application Ser. No. 304,524, filed Nov. 7, 1972, and now U.S. Pat. No. 3,971,778, which is in turn a continuation-in-part of application Ser. No. 252,666, filed May 12, 1972, and now abandoned.

This invention is concerned with improvements in or relating to antibiotics of the cephalosporin series.

The cephalosporin compounds referred to in this specification are generally named with reference to cepham (J. Amer. Chem. Soc. 1962, 84 3400). The term "cephem" refers to the basic cepham structure with one double bond.

As is well known, antibiotics of the cephalosporin series are 7β-acylamido-ceph-3-cm-4-carboxylic acids and their various non-toxic derivatives, e.g. salts, esters, lactones (if such can be formed), amides, hydrates or the corresponding sulphoxides. These antibiotics may contain various substituents particularly at the 3-position including unsubstituted methyl and methyl groups substituted with a variety of substituents as is described in the literature.

The new compounds of the present invention are characterized in that said acylamido group of the cephalosporin antibiotic is an (α-etherified oximino) acylamido group, the compounds being syn isomers or mixtures wherein the syn isomeric form predominates.

According to one embodiment of the invention, therefore, we provide a compound selected from the group of 7β-acylamidoceph-3-cm-4-carboxylic acids (and non-toxic derivatives thereof) characterized in that said acylamido group has the structure:

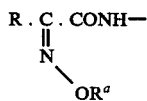

where R is a hydrogen atom or an organic group and $R^a$ is an etherifying monovalent organic group linked to the oxygen atom through a carbon atom, said compound being a syn isomer or existing as a mixture containing at least 75% of the syn isomer. Preferably, the mixtures of isomers contain at least 90% of the syn isomer and not more than 10% of the anti isomer.

The compounds of the invention are defined as having the syn (cis) isomeric form as regards the configuration of the group $OR^a$ with respect to the carboxamido group. In this specification, the syn configuration is structurally denoted thus:

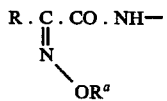

and the anti configuration thus:

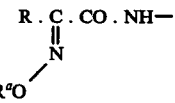

These configurations are assigned on the basis of the work of Ahmad and Spencer (Can. J. Chem., 1961, 39, 1340).

The compounds of the invention may be defined by the formula:

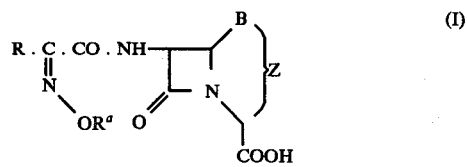

where R and $R^a$ have the above-defined meanings, B is $> S$ or $> S \rightarrow O$ and Z is a group in which 2 carbon atoms link the nuclear sulphur atom and the carbon atom bearing the carboxylic acid group and which possesses $\Delta^3$ unsaturation.

The term "non-toxic" as applied to the derivatives of the compounds of the invention means those derivatives which are physiologically acceptable in the dosage at which they are administered.

Salts which may be formed, where applicable, from the compounds according to the invention include (a) inorganic base salts such as alkali metal, e.g. sodium and potassium, alkaline earth metal e.g. calcium, and organic base, e.g. procaine, phenylethylbenzylamine, dibenzylethylene diamine, ethanolamine, diethanolamine and N-methylglucosamine salts and (b) acid addition salts, e.g. with hydrochloric, hydrobromic, sulphuric, nitric, phosphoric, toluene-p-sulphonic and methane sulphonic acids. The salts may also be in the form of resinates, formed e.g. with a polystyrene resin containing amino, quaternary amino, or sulphonic acid groups, or a resin containing carboxyl groups, e.g. a polyacrylic acid resin. The resin may if desired be cross-linked, e.g. it may be a copolymer of styrene and divinyl-benzene containing the appropriate groups. Additionally, the derivatives may be in the form of a chelate with a heavy metal such as iron or copper.

The compounds of the invention, include the non-toxic derivatives thereof, are characterized by their high antibacterial activity against a range of gram-positive and gram-negative organisms coupled with particularly high stability to β-lactamases produced by various gram negative organisms.

Stability to β-lactamases may be assessed as compared with cephaloridine which may be arbitrarily defined as having a value of 1 with respect to the particular organism.

The properties possessed by the compounds according to the invention render them useful in the treatment of a variety of diseases caused by pathogenic bateria in human beings and animals.

Preferred cephalosporin compounds according to the invention may be defined as compounds of the general formula

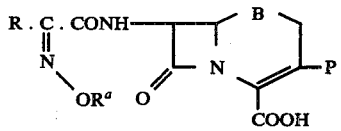

(wherein R, R$^a$ and B have the above defined meanings and P is an organic group) and non-toxic derivatives thereof. In formula (II) B is preferably > S.

The invention also includes cephalosporin compounds not specifically embraced by formula (II), e.g. 2-methyl and 2-methylene cephalosporins.

The group R$^a$ in the above formulae may be any group having a carbon atom with one free valency so that forms the desired ether group with the adjacent oxygen atom. The group R$^a$ desirably contains not more than 16 carbon atoms.

R$^a$ may thus be, for example, an alkyl group containing 1-16 carbon atoms, particularly a lower alkyl group containing 1-8 carbon atoms, e.g. a methyl, ethyl, n-propyl, iso-propyl, n-butyl, iso-butyl secbutyl, t-butyl, octyl or dodecyl group; an alkenyl group containing 2-16 carbon atoms, preferably 2-8 carbon atoms, e.g. a vinyl, allyl, isopropenyl, or dimethylallyl group; an alkynyl group containing 2-16 carbon atoms, preferably 2-8 carbon atoms, e.g. a propynyl group such as propargyl; a cycloalkyl group containing 3-7 carbon atoms, e.g. a cyclopropyl, cyclopentyl or cyclohexyl group; a cycloalkenyl group containing 4-7 carbon atoms, e.g. a cyclopentenyl, cyclohexenyl, cyclopentadienyl or cyclohexadienyl group; a carbocyclic aryl group, e.g. a phenyl or naphthyl group; a heterocyclic group, particularly one having a 5- or 6-membered heterocyclic ring, containing at least one hetero atom selected from oxygen, nitrogen and sulfur, e.g. a pyridyl, pyrimidyl, furyl, thienyl, thiazolyl, thiadiazolyl, diazolyl, triazolyl, tetrazolyl, thiatriazolyl, oxazolyl, oxadiazolyl, benzimidazolyl, benzoxazolyl or purinyl group; or a carbocyclic or heterocyclic aryl lower allkyl group in which the lower alkyl portion contains 1-4 carbon atoms, e.g. a benzyl, phenylethyl, diphenylmethyl, triphenylmethyl, thienylmethyl such as thien-2-ylmethyl, furylmethyl such as furfuryl, pyridylmethyl, or pyrrolylmethyl group.

In general R$^a$ may be unsubstituted or may carry one or more substituents such as, for example, hydroxy; alkoxy, e.g. methoxy, ethoxy, n-propxy or isopropoxy, as in, for example, methoxymethyl or 1-ethoxyethyl; aryloxy, e.g. phenoxy; aralkoxy, e.g. benzyloxy; mercapto; alkylthio, e.g. methylthio or ethylthio; arylthio; aralkylthio; amino as in, for example, 2-aminoethyl; substituted amino, e.g. methylamino, ethylamino or dimethylamino; halo, e.g. chloro or bromo, as in, for example 2-bromoethyl; nitro; azido, carboxy, esterified carboxy, e.g. lower alkoxycarbonyl such as methoxycarbonyl or ethoxycarbonyl, or benzyloxycarbonyl; formyl; acyl, e.g. acetyl, propionyl or benzoyl; acyloxy e.g. acetoxy, propionyloxy or pivaloyoxy; cyano; phthalimido; acylamido, e.g. acetamido or benzamido; alkoxycarbonylamino, e.g. methoxycarbonylamino or ethoxycarbonylamino; or aralkoxycarbonylamino, e.g. benzyloxycarbonylamino.

The group R in the above general formulae may be chosen from the following list which is not intended to be exhaustive:

i. Hydrogen, ii. R$^u$, where R$^u$ is aryl (carbocyclic or heterocyclic), cycloalkyl, substituted aryl, substituted cycloalkyl, cycloalkadienyl, or a non-aromatic or mesionic group. Examples of this group include phenyl; naphthyl e.g. naphth-1-yl; phenyl or naphthyl substituted by halo e.g. chloro or bromo as in o-chlorophenyl, hydroxy, lower alkyl e.g. methyl, nitro, amino, lower alkylamino e.g. methylamino, diloweralkylamino e.g. dimethylamino, lower alkanoyl e.g. acetyl, lower alkanoylamido, lower alkoxy e.g. methoxy or ethoxy, or lower alkylthio e.g. methylthio; a 5- or 6-membered heterocyclic group containing at least one hetero atom selected from S, N an O e.g. thien-2-yl, thien-3-yl, furyl such as fur-2-yl, pyridyl such as pyrid-3-yl, pyrrolyl, N-substituted pyrrolyl e.g. N-methylpyrrolyl or N-benzyloxymethylpyrrolyl, isothiazolyl, thiadiazolyl, oxadiazolyl, 3- or 4-isoxazolyl; substituted 3- or 4-isoxazolyl e.g. 3-aryl-5-methylisoxazol-4-yl, the aryl group being e.g. phenyl or halophenyl; fused heterocyclic groups containing at least one hetero atom selected from S, N and O, e.g. benzothinyl such as benzothien-3-yl, benzofuryl, indolyl; cyclohexyl; cyclopentyl; sydnone; and cyclohexadienyl.

iii. R$^u$ (CH$_2$)$_m$Q$_n$(CH$_2$)$_p$ where R$^u$ has the above defined meaning and $m$ is O or an integer from 1 to 4, $n$ is 0 or 1, $p$ is an integer from 1 to 4 and Q is S, O or NR wherein R is hydrogen or an organic group e.g. alkyl such as methyl or aryl such as phenyl. Examples of this group include methyl, ethyl or butyl substituted by the various specific R$^u$ groups listed under (ii) e.g. benzyl and the appropriate substituted benzyl groups.

iv. C$_n$H$_{2n+1}$ wherein $n$ is an integer from 1 to 7.

The group may be straight or branched and, if desired, may be interrupted by an oxygen or sulphur atom or the group NR wherein R is hydrogen or an organic group e.g. alkyl such as methyl or aryl such as phenyl; or be substituted by a cyano, carboxy, alkoxycarbonyl, hydroxy or carboxycarbonyl (HOOC.CO.) group or by a halogen atom. Examples of such groups include hexyl, heptyl, butylthiomethyl, cyanomethyl or trihalomethyl.

v. C$_n$H$_{2n-1}$ where $n$ is an integer from 2 to 7. The group may be straight or branched and, if desired, may be interrupted by an oxygen or sulphur atom or the group NR wherein R is hydrogen or an organic group e.g. alkyl such as methyl or aryl such as phenyl. An example of such a group is vinyl or propenyl.

vi. C$_n$H$_{2n-3}$ where $n$ is an integer from 2 to 7. An example of such a group is ethynyl.

vii. Miscellaneous carbon-linked organic groups including cyano, amido and lower alkoxycarbonyl.

The 3-substituents P of the above compounds of formula II may be any organic group, the characterising feature of the invention being the nature of the 7-substituent. P may thus be saturated or unsaturated, substituted or unsubstituted, organic group containing 1-20 carbon atoms. Preferred saturated organic groups include methyl and ethyl; preferred unsaturated organic groups include vinyl and substituted vinyl groups of the formula

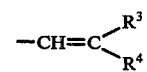

wherein R$^3$ and R$^4$, which may be the same or different, are each hydrogen or a substituted or unsubstituted aliphatic (e.g. alkyl, preferably C$_1$-C$_6$ alkyl such as methyl, ethyl, iso-propyl, n-propyl etc.), C$_5$-C$_7$ cycloaliphatic (e.g. cyclopentyl or cyclohexyl), $C_7$–$C_{10}$ araliphatic (e.g. benzyl or phenylethyl), $C_6$–$C_{12}$ aromatic (e.g. phenyl or nitrophenyl) group, nitrile or lower alkoxycarbonyl.

When P is a substituted methyl group it may be depicted by the formula

—CH$_2$Y wherein Y is an atom or group e.g. the residue of a nucleophile or a derivative of a residue of a nucleophile. Y may thus, for example, be derived from the wide range of nucleophilic substances characterised by possessing a nucleophilic nitrogen, carbon, sulphur or oxygen atom described widely in earlier patents and literature pertaining to cephalosporin chemistry. Examples of such nucleophiles include:

NITROGEN NUCLEOPHILES

Examples of nitrogen nucleophiles include tertiary aliphatic, aromatic, araliphatic and cyclic amines including trialkylamines, for example, triethylamine, pyridine bases such as pyridine and alkyl pyridines; heterocyclic amines having more than one heteroatom, at least one heteroatom being nitrogen, such as pyrimidines, purines, pyridazines, pyrazines, pyrazoles, imidazoles, triazoles and thiazoles.

A preferred class of nitrogen nucleophile are those compounds of the formula:

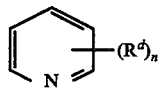

in which $n$ is 0 or an integer from 1 to 5 $R^d$, which when $n$ is from 2 to 5, may be the same or different, is an aliphatic, e.g. lower alkyl such as methyl, ethyl, n-propyl, iso-propyl etc.; an aryl e.g. phenyl; an araliphatic, e.g. phenyl lower alkyl such as benzyl, phenylethyl etc; or an alkoxymethyl e.g. methoxymethyl, ethoxymethyl, n-propoxymethyl, iso-propoxymethyl etc; or acyloxymethyl e.g. alkanoyloxymethyl such as acetoxymethyl; formyl; carbamoyl; acyloxy e.g. alkanoyloxy such as acetoxy; esterified carboxyl; alkoxy e.g. methoxy, ethoxy, n-propoxy, iso-propoxy etc.; aryloxy, e.g. phenoxy, aralkoxy e.g. benzyloxy; alkylthio e.g. methylthio, ethylthio; arylthio; aralkylthio; cyano; hydroxy; N-monoloweralkylcarbamoyl e.g. N-methylcarbamoyl, N-ethylcarbamoyl etc; N,N-diloweralkylcarbamoyl e.g. N,N-dimethylcarbamoyl, N,N-diethylcarbamoyl etc; N-(hydroxyloweralkyl)carbamoyl e.g. N-(hydroxymethyl)carbamoyl, N-(hydroxyethyl)carbamoyl etc; or carbamoylloweralkyl e.g. carbamoylmethyl, carbamoylethyl etc. group.

Another preferred class of nitrogen nucleophiles are azides e.g. alkali metal azides such as sodium azide.

When the group Y is a derivative of a residue of a nucleophile it may be an amino group or an acylamido group. Compounds in which Y is amino may be derived from the corresponding azide by reduction e.g. by catalytic hydrogenation of the azide using a precious metal catalyst such as palladium or platinum.

The amino group may be acylated to form a corresponding 3-acylaminomethyl compound. The formation of such compounds may, for example, be effected by any method suitable for acylating an aminocephalosporin e.g. reaction of the 3-aminomethyl compound with an acid chloride, acid anhydride or mixed anhydride or an acid corresponding to the desired acyl group and another acid.

The 3-aminomethyl compounds may also be reacted with a substituted isocyanate or isothiocyanate to yield urea or thiourea derivatives.

Other compounds in which Y is a derivative of a residue of a nucleophilic may be obtained by reacting 3-azidomethyl compounds with a dipolarophile. Preferred classes of dipolarophiles include acetylenic, ethylenic and cyano dipolarophiles.

Acetylenic dipolarophiles may be shown as having the structure $R^1.C \equiv C.R^2$ wherein $R^1$ and $R^2$ which may be the same or different are atoms or groups.

In general we prefer that $R^1$ and preferably also $R^2$ should be of an electronegative nature. Examples of such groups include cyano, $CO_2R^3$, $COR^3$ (where $R^3$ is for example, lower alkyl, aryl or lower aralkyl), and trihalomethyl e.g. trifluoromethyl.

However, $R^1$ and preferably also $R^2$ could be electropositive e.g. alkoxy or alkylamino.

$R^1$ and $R^2$ may together form a ring system with the acetylenic group such as, for example, in an aryne.

Where $R^1$ and $R^2$ are discrete atoms or groups which are identical a single compound will result on reaction with the azido cephalosporin; if they are different one will in general obtain a mixture of position isomers.

Ethylenic dipolarophiles may be shown as having the structure

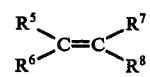

where $R^5$, $R^6$, $R^7$ and $R^8$ which may be the same or different are atoms or groups. Although $R^5$, $R^6$, $R^7$ and $R^8$ may all be hydrogen, ethylene per se, like acetylene, reacts sluggishly with azido groups. $R^5$ and $R^7$ may together form a cyclic structure, e.g. a carbocyclic structure, with the ethenoid group such that the double bond is strained. Examples of ethylenic dipolarophiles containing strained double bonds include norbornenes, transcycloalkenes and acenaphthalene.

Further ethylenic dipolarophiles which may be used include compounds of the formula $R^5.R^6.C = CR^7.R^8$ where at least one $R^5$, $R^6$, $R^7$ and $R^8$ is an electronegative group. $R^5$ and $R^7$ may thus be identical electronegative groups, $R^6$ and $R^8$ being other groups as desired. $R^6$ and $R^8$ may thus together form a ring system. Examples of such dipolarophiles include benzoquinone and nuclear substituted benzoquinones and maleimide. Again all of $R^5$, $R^6$, $R^7$ and $R^8$ may be identical electronegative groups. Electronegative groups which may be used include those listed under the section on acetylenic dipolarphiles and examples of such compounds thus include dicyanoethylene and lower mono- and di-alkoxycarbonyl ethylenes.

One or more of $R^5$, $R^6$, $R^7$ and $R^8$ may if desired be electropositive.

Cyano compounds, especially those which are activated by electronegative groups, may function as cyano dipolarophiles. Examples of such dipolarophiles include lower alkoxy carbonyl cyanides and cyanogen.

CARBON NUCLEOPHILES

Examples of "carbon nucleophiles" include inorganic cyanides, pyrroles and substituted pyrroles, e.g. indoles, and compounds giving stabilised carbanions, for example, acetylenes and compound having β-diketone groups, for example acetoacetic and malonic esters and cyclohexane-1,3-diones or enamines, ynamines or enols.

The carbon nucleophile may thus give rise to cephalosporin compounds characterized by possessing a substituent at the 3-position in which a carbonyl group is linked to the cephalosporin nucleus through two carbon atoms. Such compounds may thus possess as the 3-substituent a group of the formula

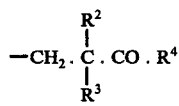

where $R^2$ and $R^3$, which may be the same or different, are selected from hydrogen, cyano, lower alkyl e.g. methyl or ethyl, phenyl, substituted phenyl e.g. halo, lower alkyl, lower alkoxy, nitro, amino or lower alkylamino phenyl, lower alkoxycarbonyl, mono- or di-aryl lower alkoxycarbonyl, lower alkylcarbonyl, aryl lower alkyl or $C_5$ or $C_6$ cycloalkyl and $R^4$ is selected from hydrogen, lower alkyl e.g. methyl or ethyl, phenyl, substituted phenyl e.g. halo, lower alkyl, lower alkoxy, nitro, amino or lower alkylamino phenyl, aryl lower alkyl or $C_5$ or $C_6$ cycloalkyl.

SULPHUR NUCLEOPHILES

Examples of "sulphur nucleophiles" include thiourea and aliphatic, aromatic, araliphatic, alicyclic and heterocyclic substituted thioureas; dithiocarbamates; aromatic, aliphatic and cyclic thioamides, for example thioacetamide and thiosemicarbazide; thiosulphates; thiols; thiophenols; thioacids; e.g. thiobenzoic acid or thiopicolinic acid; and dithioacids.

A preferred class of sulphur nucleophile includes those compounds of the formula: $R_1.S(O)_nH$ in which $R^1$ is an aliphatic e.g. lower alkyl such as methyl, ethyl, n-propyl etc. group; an alicyclic e.g. cyclohexyl, cyclopentyl etc. group; an aromatic e.g. phenyl, naphthyl etc. group; an araliphatic e.g. benzyl group; or a heterocyclic group, and $n$ is 0, 1 or 2. A particularly preferred class of nucleophiles falling within the above formula is that having the general formula: $R^6SH$ in which $R^6$ is an aliphatic e.g. lower alkyl e.g. methyl, ethyl, n-propyl etc.; loweralkylcarbonyl e.g. acetyl araliphatic, e.g. phenyl lower alkyl e.g. benzyl, phenylethyl etc. or substituted phenyl lower alkyl; alicyclic e.g. cycloalkyl e.g. cyclopentyl or cyclohexyl; aromatic e.g. phenyl or substituted phenyl or a 5- or 6-membered heterocyclic group containing at least one of O, N and S e.g. thiadiazolyl, particularly 5-methyl-1,3,4-thiadiazol-2-yl or 2-phenyl-1,3,4-oxadiazol-5-yl, diazolyl, triazolyl, tetrazolyl, particularly 1-methyltetrazole-5-yl or 1-ethyltetrazole-5-yl thiazolyl, thiatriazolyl, oxazolyl, oxadiazolyl, pyridyl and pyrimidyl, or a substituted heterocyclic group, including such groups substituted by a divalent group to give a fused ring system, e.g. benzimidazolyl, benzoxazolyl, triazolpyridyl, benzothiazolyl, particularly nitrobenzothiazolyl and purinyl.

OXYGEN NUCLEOPHILES

Examples of oxygen nucleophiles include water, alcohols, for example alkanols such as methanol, ethanol, propanol and butanol and lower alkanoic and alkenoic acids.

The term "oxygen nucelophile" thus includes compounds of the following formula: $R'OH$ in which the group $R'$ may be lower alkyl (e.g. methyl, ethyl, n-propyl, isopropyl, n-butyl, isobutyl etc.); lower alkenyl (e.g. allyl); lower alkynyl (e.g. propynyl, etc); lower cycloalkyl (e.g. cyclopropyl, cyclopentyl, cyclohexyl, etc); lower cycloalkyl lower alkyl (e.g. cyclopropylmethyl, cyclopentylmethyl, cyclohexylethyl etc); aryl (e.g. phenyl or naphthyl); aryl lower alkyl (e.g. benzyl); heterocyclic; heterocyclic lower alkyl (e.g. furfuryl) or any of these groups substituted by, for example, one or more of lower alkoxy (methoxy, ethoxy, etc.), lower alkylthio (methylthio, ethylthio, etc), halogen (chlorine, bromine, iodine or fluorine), lower alkyl (methyl, ethyl etc), nitro, hydroxy, acyloxy, carboxy, carbalkoxy, lower alkylcarbonyl, lower alkylsulphonyl, lower alkoxysulphonyl, amino, lower alkylamino or acylamino groups.

In the case in which water is the nucleophile there will be obtained 3-hydroxymethyl cephalosporin compounds. Such compounds have the formula

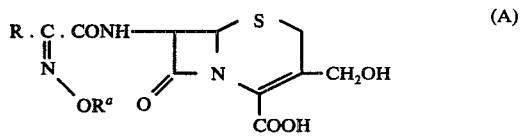

where R and $R^a$ have the above defined meanings. Compounds of formula (A) and non-toxic derivatives thereof possess antibacterial activity and it is of note that they may be metabolites of compounds of general formula II where B is > S and P is acetoxymethyl. Compounds of formula (A) may be acylated to form derivatives characterised by possessing the group 3-$CH_2.O—.CO.R^9$ or 3—$CH_2O.CO.AR^{10}$ where A is O, S or NH, $R^9$ is methyl or an organic group having an atomic weight sum of at least 16 and $R^{10}$ is hydrogen or $R^9$.

The group $R^9CO$— or, $R^{10}A.CO$— may be chosen from among the wide class of such groups described in the literature and may have up to 20 carbon atoms. The group $R^9$ may thus be a hydrocarbon group or such a group carrying one or more substituent atoms or groups. The group $R^9$ may thus be chosen from the following list which is not intended to be exhaustive:

(i) $C_nH_{2n+1}$ where $n$ is an integer from 1 to 7, e.g. 2 to 4. The group may be straight or branched and, if desired, may be interrupted by an oxygen or sulphur atom or an imino group or substituted by cyano, carboxy, alkoxycarbonyl, hydroxy, carboxycarbonyl (HOOC.CO.), halogen e.g. chlorine, bromine or iodine, or amino. Examples of such groups include ethyl, propyl, isopropyl, n-butyl, t-butyl, sec.butyl and 2-chloroethyl.

(ii) $C_nH_{2n-1}$ where $n$ is an integer from 2 to 7. The group may be straight or branched and, if desired, may be interrupted by an oxygen or sulphur atom or an imino group. An example of such a group is vinyl or propenyl.

(iii) $R^v$, where $R^v$ is aryl (carbocyclic or heterocyclic), cycloalkyl, substituted aryl and substituted cycloalkyl. Examples of this group include phenyl; substituted phenyl e.g. hydroxyphenyl, chlorophenyl, fluorophenyl, tolyl, nitrophenyl, aminophenyl, methoxyphenyl or methylthiophenyl; thien-2- and -3-yl; pyridyl; cyclohexyl; cyclopentyl; cyclopropyl; sydnone; naphthyl; substituted naphthyl e.g. 2-ethoxynaphthyl.

(iv) $R^v(CH_2)_m$ where $R^v$ has the meaning defined above under (iii) and $m$ is an integer from 1 to 4. Examples of this group include methyl, ethyl or butyl substituted by the various specific $R^v$ groups listed under (iii) e.g benzyl and the appropriate substituted benzyl groups.

An important class of cephalosporin compounds are those possessing the group 3-$CH_2$Hal wherein Hal is chlorine, bromine or iodine. Such compounds may be primarily of value as intermediates of use in the preparation of active cephalosporin compounds.

Important antibiotic compounds according to the invention by virtue of their generally broad spectrum antibiotic properties including activity against strains of *Haemophilus influenzae* coupled with stability to β-lactamases produced by a variety of gram-negative organisms are compounds of the general formula

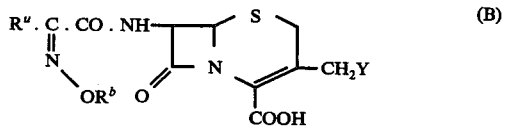

and non-toxic derivatives thereof. In formula (B) $R^u$ is phenyl; naphthyl; thienyl; furyl; benzothienyl, benzofuryl or pyridyl or any of these groups substituted by halo (chloro, bromo, iodo or fluoro), hydroxy, lower alkyl, nitro, amino, loweralkylamine, diloweralkylamine, lower alkanoyl, lower alkanoylamido, lower alkoxy, lower alkylthio or carbamoyl; $R^b$ is lower alkyl, cycloalkyl ($C_{3-7}$), or aryl (carbocyclic e.g. phenyl or heterocyclic e.g. thienyl or furyl) lower alkyl or any of these groups substituted by hydroxy, carboxy, esterified carboxy, amido, cyano, alkanoyl, amino, substituted amino, nitro halogen or lower alkoxy; and the group Y is selected from a. acetoxy;

b. the residue of a nitrogen nucleophile of the formula

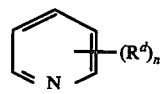

(wherein $R^d$ and $n$ have the above defined meanings); in this case the 4-position group of the compound of formula (B) will be present as $-CO_2^-$;

c. the group —SW wherein W is thiadiazolyl preferably 5-methyl-1,3,4-thiadiazol-2-yl, diazolyl, triazolyl, tetrazolyl, preferably 1-methyltetrazol-5-yl and 1-ethyltetrazol-5-yl, thiazolyl, thiatrazolyl, oxazolyl, oxadiazolyl, benzimidazolyl, benzoxazolyl, triazolopyridyl, benzothiazolyl, preferably nitrobenzothiazolyl, purinyl, pyridyl or pyrimidyl;

d. lower ($C_1$-$C_4$) alkylthio;

e. the group —O.CO.$R^9$ wherein $R^9$ is $C_2$-$C_4$ alkyl or $C_2$-$C_4$ alkenyl;

f. the group —O.CO.NH.$(CH_2)_m$D wherein $m$ is an integer of from 1–4 and D is chlorine, bromine, iodine of fluorine; and g. azido: Particularly important compounds of general formula (B) by virtue of their broad spectrum antibiotic properties, including high activity against strains of *Pseudomonas pyocyanea* are those having the general formula

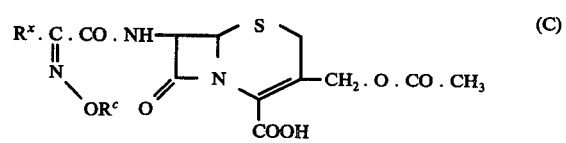

(wherein $R^x$ is phenyl; naphthyl; thienyl; furyl; benzothienyl or benzofuryl and $R^c$ is $C_2$-$C_4$ alkyl, cyclopentyl, phenyl, benzyl, phenethyl, thienylmethyl, furylmethyl) and non-toxic derivatives thereof.

Important compounds falling within general formula (C) include the following compounds in their syn isomeric form:

3-acetoxymethyl-7β-(2-ethoxyimino-2-phenylacetamido)-ceph-3-em-4-carboxylic acid;

3-acetoxymethyl-7β-[2-t-butoxyimino-2-(2-thienyl)acetamido]ceph-3-em-4-carboxylic acid;

3-acetoxymethyl-7β-[2-(2-thienyl)methoxyimino-2-(2-thienyl)acetamido]ceph-3-em-4-carboxylic acid;

3-acetoxymethyl-7β-[3-t-butoxyimino-2-(2-furyl)acetamido]ceph-3-em-4-carboxylic acid;

3-acetoxymethyl-7β-[2-benzyloxyimino-2-(2-thienyl)acetamido]ceph-3-em-4-carboxylic acid;

3-acetoxymethyl-7β-[2-t-butoxyimino-2-(1-naphthyl)acetamido]ceph-3-em-4-carboxylic acid; and 3-acetoxymethyl-7β-[2-n-butoxyimino-2-(2-thienyl)acetamido]ceph-3-em-4-carboxylic acid;

3-acetoxymethyl-7β-(2-phenoxyimino-2-phenylacetamido) ceph-3-em-4-carboxylic acid;

3-acetoxymethyl-7β-[2-phenoxyimino-2-(2-thienyl)acetamido] ceph-3-em-4-carboxylic acid;

3-acetoxymethyl-7β-[2-cyclopentyloxyimino-2-(2-furyl) acetamido]ceph-3-em-4-carboxylic acid;

3-acetoxymethyl-7β-[2-cyclopentyloxyimino-2-(2-thienyl) acetamido]ceph-3-em-4-carboxylic acid;

3-acetoxymethyl-7β-(2-cyclopentyloxyimino-2-phenyl-acetamido)ceph-3-em-4-carboxylic acid;

especially as their sodium, potassium or di ethanolamine salts.

An important group of compounds falling within general formula (B) by virtue of their broad spectrum antibiotic properties including high activity against strains of *Haemophilus influenzae* and those having the general formula

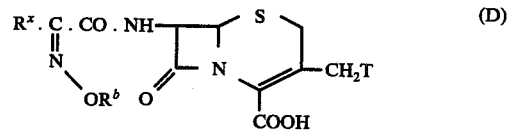

[wherein $R^x$ and $R^b$ are as defined above and T is acetoxy, azido, the residue of a nitrogen nucleophile of the formula

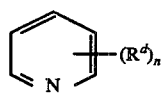

(wherein $R^d$ and $n$ have the above defined meanings) or the group —O.CO.$R^9$ wherein $R^9$ is $C_2$–$C_4$ alkyl, $C_2$–$C_4$ alkenyl or phenyl] and non-toxic derivatives thereof.

A further important group of compounds falling within general formula (B) by virtue of their broad spectrum antibiotic properties coupled with significant absorption on oral administration as evidenced by animal tests are those having the general formula

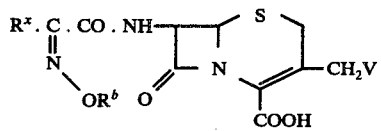
(E)

(wherein $R^x$ and $R^b$ have the meanings defined above and V is lower ($C_1$–$C_4$) alkylthio, $C_2$–$C_4$ alkanoyl or $C_2$–$C_4$ alkenoyl) and non-toxic derivatives thereof.

A still further important group of compounds falling within general formula (B) which possess a very high degree of activity against a variety of gram positive and gram negative organisms coupled with high stability to β-lactamases produced by a variety of organisms are those having the general formula

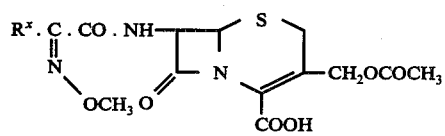
(F)

[wherein $R^x$ is a defined above the formula (C)] and non-toxic derivatives thereof. A particularly important compound of formula (F) is 3-acetoxymethyl-7β-(2-methoxyimino-2-phenylacetamido)ceph-3-em-4-carboxylic acid (syn-isomer), especially as its sodium or potassium salt.

Preparation

The compounds according to the invention may be prepared by any convenient method. According to one embodiment of the invention we provide a process for the preparation of a compound of the formula

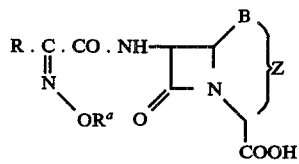
(I)

(wherein R is a hydrogen atom or an organic group, $R^a$ is an etherifying monovalent organic group linked to the oxygen atom through a carbon atom, B is > S or > S → O and Z is a group in which 2 carbon atoms link the nuclear sulphur atom and the carbon atom bearing the carboxylic acid group and which possesses $\Delta^3$ unsaturation) and derivatives thereof, which comprises either (A) condensing a compound of the formula

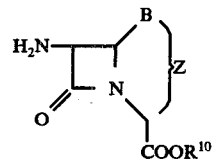
III (wherein B and Z have the above defined meanings and $R^{10}$ is hydrogen or a carboxyl blocking group) with an acylating agent, advantageously the syn isomer, corresponding to the acid

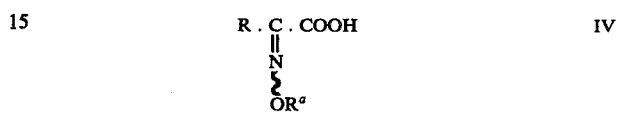
IV (wherein R and $R^a$ have the above defined meanings) or with an acylating agent corresponding to an acid which is a precursor for the acid IV; or (B) reacting a compound of the formula

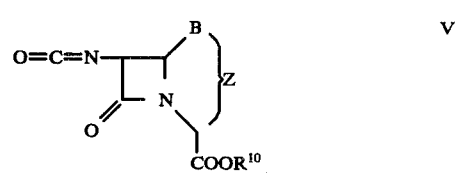
V (wherein B, Z and $R^{10}$ have the above defined meaning except that $R^{10}$ is not hydrogen) with an acid, or precursor, of formula IV; or (C), where Z is the group

(wherein Y is the residue of a nucleophile or a derivative of the residue of a nucleophile and the dotted line bridging the 2,3 and 4 positions indicates that the compound may be a ceph-2-em or a ceph-3-em compound) reacting a compound of the formula

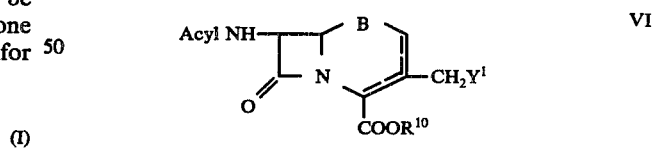
VI (wherein Acyl is the group

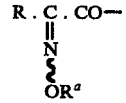

or a precursor therefore; B, $R^a$, $R^{10}$ and the dotted line have the above meanings and $Y^1$ is a replaceable residue of a nucleophile) with a nucleophile whereafter, if necessary and desired in each instance, any of the following reactions (D) are carried out (i) conversion of a precursor for the

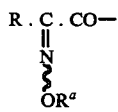

group into that said group (ii) conversion of a Δ² isomer into the desired Δ³ isomer (iii) removal of any carboxyl blocking groups (iv) reduction of a compound in which Z is > S → O to form the desired Z = > S compound (v) reduction of a compound in which Y is azide to form a 3-aminomethyl compound and, if required, acylation of the resulting amino group to form a corresponding 3-acylaminomethyl compound (vi) reaction of a compound in which Y is azide with a dipolarophile to form a compound having a polyazole ring linked to the 3-methylene group (vii) deacylation of a compound in which Y is an acyloxy group to form a 3-hydroxymethyl compound and (viii) acylation of a compound in which Y is hydroxy to form a 3-acyloxymethyl or 3-carbamoyloxymethyl compound and (E) recovering the desired compound of formula (I), after separation of isomers if necessary.

Salts of the compounds according to the invention may be formed in any convenient way. For example base salts may be formed by reaction of the cephalosporin acid with sodium or potassium 2-ethylhexanoate.

In practice it is convenient to condense an acylating agent corresponding to the acid

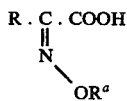

where R and R<sup>a</sup> have the above defined meanings, with an amino compound

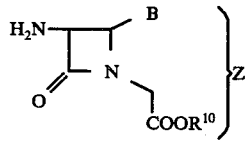

[where Z and B have the above defined meanings and R¹⁰ is hydrogen or a carboxyl blocking group e.g. the residue of an ester-forming alcohol (aliphatic or araliphatic), phenol, silanol, stannanol or acid] the condensation if desired being effected in the presence of a condensation agent, and being followed, if necessary, by removal of the group R¹⁰.

In the case of the preparation of the preferred cephalosporin compounds of formula (II) above, the amino compound (III) may have the formula

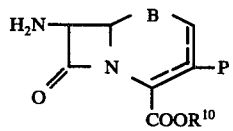

wherein R¹⁰, B and P have the above defined meanings. There may also be used a derivative of the amino compounds such as salt e.g. a tosylate, or an N-silyl derivative.

The compounds of formula I may thus be prepared by employing as the acylating agent an acid halide, particularly an acid chloride or bromide. The acylation may be effected at temperatures of from −50° to +50° C, preferably −20° to +30° C. The acylating agent may be prepared by reacting the acid VII or a salt thereof with a halogenating agent e.g. phosphorus pentachloride, thionyl chloride or oxayl chloride. Use of oxalyl chloride with the sodium or potassium salt of the acid (VII) is preferred since under these conditions isomerisation in minimal. The acylation may be effected in aqueous or non-aqueous media and suitable media include an aqueous ketone such as aqueous acetone, an ester e.g. ethyl acetate, or an amide e.g. dimethylacetamide, or a nitrile e.g. acetonitrile, or mixtures thereof.

Acylation with an acid halide may be effected in the presence of an acid binding agent e.g. a tertiary amine (e.g. triethylamine or dimethylaniline), an inorganic base (e.g. calcium carbonate or sodium bicarbonate) or an oxirane, which binds hydrogen halide liberated in the acylation reaction. The oxirane is preferably a lower-1,2-alkylene oxide e.g. ethylene oxide or propylene oxide.

When using the free acid form of a compound of formula (VII), suitable condensing agents for use in the preparation of the compounds according to the invention include carbodiimides, for example N,N'-diethyl-, dipropyl- or diisopropylcarbodiimide, n,N'-dicylohexylcarbodiimide, or N-ethyl-N'-γ-dimethylaminopropylcarbodiimide; a suitable carbonyl compound, for example carbonyldiimidazole; or an isoxazolinium salt, for example, N-ethyl-5-phenylisoxazolinium-3'-sulphonate and N-t-butyl-5-methylisoxazolinium perchlorate. The condensation reaction is desirably effected in an anhydrous reaction medium, e.g. methylene chloride, dimethylformamide or acetonitrile.

Alternatively, acylation may be effected with other amide-forming derivatives of the free acid such as, for example, a symmetrical anhydride or mixed anhydride, e.g. with pivalic acid or formed with a haloformate, e.g. a lower alkylhaloformate. The mixed or symmetrical anhydrides may be generated in situ. For example, a mixed anhydride may be generated using N-ethoxycarbonyl-2-ethoxy-1, 2-dihydroquinoline. Mixed anhydrides may also be formed with phosphorus acids (for example phosphoric or phosphorous acids), sulphuric acid or aliphatic or aromatic sulphonic acids (for example p-toluene sulphonic acid). Another convenient acylating agent is an activated ester e.g. a compound of the formula

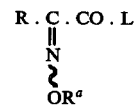

where L, is for example, azide, oxysuccinimide, oxybenztriazole, pentachlorophenoxy or p-nitrophenoxy group.

Alternatively the compound of formula (I) may be prepared from a compound of formula

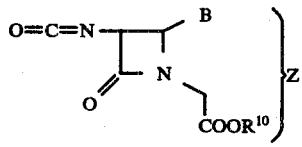
(V)

(where B, Z and $R^{10}$ have the above defined meanings except that $R^{10}$ is not hydrogen) by reaction with an acid, or precursor, of formula VII and subsequently removing the group $R^{10}$ (see for example Belgian Pat. No. 760,494).

The reaction of the compound of formula (III) or (V) may be carried out towards the end of a preparative sequence, the only additional reactions being deprotection reactions and purifications.

If desired, one can first prepare a compound of formula

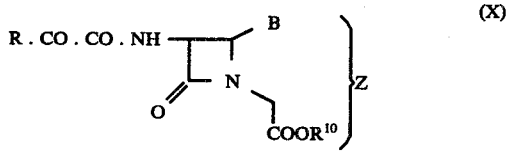
(X)

(where R, $R^{10}$, B and Z have the above defined meanings) and then effect reaction of the compound of formula (X) with $R^aO.NH_2$ ($R^a$ having the above defined meaning), followed, if necessary by removal of the group $R^{10}$. The reaction product may be separated to give the required syn isomer before or after removal of $R^{10}$.

A useful precursor of the desired R.C.CO—

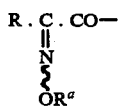

group is the corresponding 2-hydroxyiminoacyl group

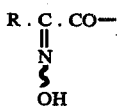

since this may readily be converted to the desired group by etherification. Thus compounds of formula (I) may be prepared by reacting a compound of formula

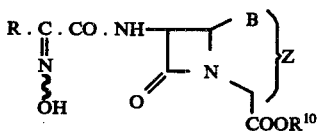
XI wherein R, $R^{10}$, B and Z are as hereinbefore defined, with an etherifying agent serving to introduce the group $R^a$ and subsequently if necessary and desired carrying out any of reactions D(ii)–(viii) described above and recovering the desired compound of formula (I), after separation of isomers if necessary.

The etherifying agent may be, for example, an organic halide or sulphate, or a sulphonate such as tosylate. Other etherifying agents include diazoalkanes, e.g. diazomethane or diazoethane, alkyl fluorosulphonates, e.g. methyl fluorosulphonate, and alkyloxonium tetrafluoroborates, e.g. a trialkyloxonium tetrafluoroborate such as triethyloxonium tetrafluoroborate and diphenyliodonium bromide. Etherifications using a diazo compound, fluorosulphonate or tetrafluoroborate may require assistance, e.g. with a Lewis acid such as $BF_3$.

One may prepare compounds of formula (I) wherein R is an activating group such as cyano or 2- or 4- pyridyl by a technique involving nitrosation and etherification of the resulting oxime. Thus a compound possessing the acylamido group

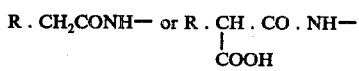

may be nitrosated using, for example, nitrous acid (which may be prepared in situ by reaction of an alkali metal nitrite with a weak acid e.g. acetic acid), nitrosyl chloride, or an organic nitrosating agent e.g. an alkyl, cycloalkyl, or aralkyl nitrite. In the case of nitrosation of a compound containing the group

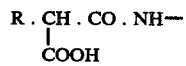

decarboxylation will occur. Separation of syn and antiisomers may be necessary after the nitrosation or etherification reaction.

If desired the replacement of one P group by another and preferred P group may be carried out after acylation of the 7-amino or 7-isocyanato compound has taken place. In particular when P is the group

where Y has the above defined meaning the Y group may be introduced by methods described in the literature. Thus compounds in which Y is a halogen atom, an ether group, or a thioether group may be prepared as described in Belgian Pat. Nos. 719,711; 719,710; 734,532 and 734,533. Compounds wherein Y is the residue of a nucleophile may also be prepared by the reaction of a 3-acetoxymethyl cephalosporin compound with a nucleophile, for example, pyridine or other tertiary amine as described in British Pat. No. 912,541; a sulphur-linking, nitrogen-linking or inorganic nucleophile as described in British Pat. No. 1,012,943; a sulphur-linking nucleophile as described in British Pat. Nos. 1,059,562, 1,101,423 and 1,206,305; or a nitrogen-linking nucleophile as described in British Pat. Nos. 1,030,630, 1,082,943 and 1,082,962.

Compounds in which Y is a derivative of a residue of a nucleophile, e.g. where Y is an amino or acylamido group derived from an azido group may be prepared as described in British Pat. Nos. 1,057,883 and 1,211,694 these patents further describing the reaction of compounds in which Y is azido with a dipolarophile. Compounds of the invention wherein Y is the residue of a nucleophile may also be prepared by the reaction of a 3-halomethyl-cephalosporin with any of the nucleophiles disclosed in the above references, such a process being described in Belgian Pat. No. 719,711. Where Y is a hydroxy group the compound may be prepared by the methods described in British Pat. No. 1,121,308.

Compounds having a vinyl or substituted vinyl group as 3-position substituent may be obtained by the method described in Belgian Pat. No. 761,897.

Where Y is a halogen (i.e. chlorine, bromine or iodine) ceph-3-em starting compounds may be prepared by halogenation of a 7β-acylamido-3-methylceph-3-em-4-carboxylic acid ester 1β-oxide followed by reduction of the 1β-oxide group later in the sequence as described in Belgian Pat. No. 755,256.

The corresponding ceph-2-em compounds may be prepared by the method of Dutch published Patent Application No. 6,902,103 by reaction of a ceph-2-em-3-methyl compound with N-bromo-succinimide to yield the ceph-2-em-3-bromomethyl compound.

Where Y is a hydrogen atom the compound may be prepared by the method described in British Pat. No. 957,569 or from a penicillin compound by the method described in U.S. Pat. No. 3,275,626 and Belgian Pat. Nos. 747,119 and 747,120.

Cephalosporin compounds possessing an acyloxymethyl group as 3-position substituent may be prepared by any convenient method e.g. they may be prepared from a cephalosporin having a 3-$CH_2Y$ group where Y = OH or the residue of the acid H Y which has a pKa of not more than 4.0 and preferably not more than 3.5 (as measured in water at 25° C).

The group Y may be a chlorine, bromine or iodine atom, formyloxy or an acetoxy group having at least one electron-withdrawing substituent on the α-carbon atom or a nuclear substituted benzoyloxy group, the nuclear substituent being of the electron withdrawing type as described in British Pat. No. 1,241,657 and the nucleophilic displacement reaction to introduce the desired 3-position substituent may be carried out as described in our aforesaid British Pat. No. 1,241,657.

Alternatively where Y is hydroxy the desired 3-acyloxymethyl cephalosporin may be obtained by acylation analogous with that described in British Pat. No. 1,141,293, which patent describes a process for the preparation of a Δ³-cephalosporin having a 3-acyloxymethyl substituent from a corresponding 3-hydroxymethyl analogue which comprises aralkylating the 4-carboxy group, acylating the 3-hydroxymethyl group of the protected compound and subsequently removing the aralkyl group.

The acylation may be carried out by any convenient method, using for example an acid chloride, acid anhydride or a mixed acid anhydride as the acylating agent, preferably in the presence of an acid binding agent, for example an organic base such as pyridine or a lower alkylene oxide such as ethylene oxide or propylene oxide, and carrying out the reaction in solution in an inert anhydrous solvent, for example methylene chloride. Alternatively the acylation may be carried out in aqueous acetone/sodium bicarbonate solution. The preferred acylating agent is the acid chloride.

The acylation reaction should be effected as rapidly as possible, since under the conditions of the acylation rearrangement to the Δ²-derivative can occur, particularly when an aroyloxy group is being introduced at the exocyclic methylene group at the 3-position.

Compounds of the formula III may be employed as esters; those of formula V are esters. One may also use the free amino acid or an acid addition salt of the free amino acid or ester thereof. Salts which may be used include acid addition salts e.g. with hydrochloric, hydrobromic, sulphuric, nitric, phosphoric, toluene-p-sulphonic and methane sulphonic acids.

The ester may be formed with an alcohol, phenol, silanol or stannanol having up to 20 carbon atoms which may readily be split off at a later stage of the overall reaction.

Any esterifying group substituting the 4-carboxyl group of a compound of formula (III), (V) or (X) is preferably formed with an alcohol (aliphatic or araliphatic), phenol, silanol, stannanol or acid which may readily be split off at a later stage of the reaction.

Suitable esters thus include compounds containing as ester group a group selected from the following list which is not intended to be an exhaustive list of possible ester groups.

(i) —$COOCR^fR^gR^h$ wherein at least one of $R^f$, $R^g$ and $R^h$ is an electron-donor e.g. p-methoxyphenyl, 2,4,6-trimethylphenyl, 9-anthryl, methoxy, acetoxy, or fur-2-yl. The remaining $R^f$, $R^g$ and $R^h$ groups may be hydrogen or organic substituting groups. Suitable ester groups of this type include p-methoxybenzyloxycarbonyl and 2,4,6-trimethylbenzyloxy carbonyl.

(ii) —$COOCR^fR^gR^h$ wherein at least one of $R^f$, $R^g$ and $R^h$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining $R^f$, $R^g$, and $R^h$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) —$COOCR^fR^gR^h$ wherein at least two of $R^f$, $R^g$ and $R^h$ are hydrocarbon such as alkyl e.g. methyl or ethyl, or aryl e.g. phenyl and the remaining $R^f$, $R^g$ and $R^h$ group, if there is one, is hydrogen. Suitable esters of this type include t-butyloxycarbonyl, t-amyloxycarbonyl, diphenylmethoxycarbonyl and triphenylmethoxycarbonyl.

(iv) —$COOR^i$ wherein $R^i$ is adamantyl, 2-benzyloxyphenyl, 4-methylthiophenyl, tetrahydrofur-2-yl or tetrahydropyran-2-yl. (v) Silyloxycarbonyl groups obtained by reaction of a carbonyl group with a derivative of a silanol. The derivative of a silanol is conveniently a halosilane or a silazane of the formula $R^{11}_3SiD$; $R^{11}_2SiD_2$; $R^{11}_3Si.NR^{11}_2$; $R^{11}_3Si.NH.SiR^{11}_3$;
$R^{11}_3Si.NH.COR^{11}$; $R^{11}_3Si.NH.CO.NH.SiR^{11}_3$;
$R^{11}NH.CO.NR^{11}.SiR^{11}_3$; or $R^{11}C(OSir^{11}_3)$:
$NSiR^{11}_3$ where D is a halogen and the various groups $R^{11}$, which can be the same or different, represent hydrogen atoms or alkyl, e.g. methyl, ethyl, n-propyl, iso-propyl; aryl, e.g. phenyl; or aralkyl e.g. benzyl groups. Preferred derivatives of silanols are silyl chlorides such as for example trimethylchlorosilane and dimethyldichlorosilane.

The carboxyl group may be regenerated from an ester by any of the usual methods, for example, acid- and base-catalysed hydrolysis is generally applicable, as well as enzymically-catalysed hydrolyses; however, aqueous mixtures may be poor solvents for these compounds and they may cause isomerizations, rearrangements, side-reactions, and general destruction, so that special methods may be desirable. Five suitable methods of deesterification are (1) Reactions with Lewis acids.

Suitable Lewis acids for reaction with the esters include trifluoroacetic acid, formic acid, hydrochloric acid in acetic acid, zinc bromide in benzene and aqueous solutions or suspensions of mercuric compounds. The reaction with the Lewis acid may be facilitated by addition of a nucleophile such as anisole.

(2) Reduction.

Suitable systems for effecting reduction are zinc/acetic acid, zinc/formic acid, zinc/lower alcohol, zinc/pyridine, palladised-charcoal and hydrogen, and sodium and liquid ammonia.

(3) Attack by nucleophiles.

Suitable nucleophiles are those containing a nucleophilic oxygen or sulphur atom for example alcohols, mercaptans and water.

(4) Oxidative methods, for example, those which involve the use of hydrogen peroxide and acetic acid.

(5) Irradiation.

Where at the end of a given preparative sequence compounds are obtained wherein B is > S → O and a compound is desired in which B is > S conversion to a sulphide may for example, be effected by reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of −20° to +50° C.

Alternatively, reduction of the 1-sulphinyl group may be affected by phosphorus trichloride or tribromide in solvents such as methylene chloride, dimethylformamide or tetrahydrofuran, preferably at a temperature of −20° C to +50° C.

Where the resultant compound is a ceph-2-em-4-ester the desired ceph-3-em compound may be obtained by treatment of the former with a base.

The acid IV to which the acylating agent corresponds may be obtained by reacting a glyoxylic acid of formula

R.CO.COOH (where R has the above defined meaning) or an ester thereof with R$^a$O.NH$_2$ (R$^a$ having the above defined meaning).

The resulting acid or ester may then be separated into its syn and anti isomers e.g. by crystallisation, chromatography or distillation, followed when necessary by hydrolysis of the ester.

Separation of the syn and anti components of an ester derivative of an α(-etherified oximino)carboxylic acid existing as a mixture of the syn and anti isomers may be effected by selective hydrolysis of the ester under basic conditions, since the less sterically hindered anti isomer tends to saponify more rapidly and may thus be removed as the free acid, leaving purified syn ester. The separated syn ester may then be converted to a corresponding acylating agent as desired. This process as described in greater detail in copending application Ser. No. 304,491 of the Janice Bradshaw and Godfrey Basil Webb filed on even date herewith.

The acid (IV) may also be prepared by carrying out an O-alkylation or O-arylation type of reaction on a compound of the formula

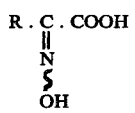

i.e. an 2-hydroximino acid, or more preferably on an ester of such an 2-hydroximino acid. The desired reaction may be achieved with an organic halide, sulphate or sulphonate, e.g. a compound of formula R$^a$J where R$^a$ has the above-defined meaning and J is halogen, sulphate or a sulphonate such as tosylate. Alternatively the 2-hydroximino acid or an ester thereof may be reacted with a diazoalkane, e.g. diazomethane, an alkyl fluorosulphonate, e.g. methyl fluorosulphonate, or an alkyloxonium tetrafluoroborate, e.g. a trialkyloxonium tetrafluoroborate such as trimethyloxonium tetrafluoroborate to give the required alkoxyimino acid (VII) or an ester thereof, or with diphenyliodonium bromide to give the required phenoxyimino acid (VII). Such reactions with a diazo compound, fluorosulphonate or tetrafluoroborate may require assistance, e.g. with a Lewis acid such as BF$_3$.

When converting the acid (IV) to a corresponding acylating agent it will be appreciated that any amino groups present in R or R$^a$ should desirably be protected to avoid undesirable side reactions; similar protection of amino groups is also desirable when reacting the consequent acylating agent with a compound of formula (III) or (V).

Syn and anti isomers may be distinguished by appropriate techniques, e.g. by their ultraviolet spectra, by thin layer or paper chromatography or by their nuclear magnetic resonance spectra. For example, for DMSO-d$_6$ solution compounds of Formula I exhibit the doublet for the amide NH at a lower field for the syn isomers than for the anti-isomers. These factors may be employed in monitoring reactions.

The antibacterial compounds according to the invention may be formulated for administration in any convenient way, by analogy with other antibiotics and the invention therefore includes within its scope a pharmaceutical composition comprising an antibacterial compound of formula I or a non-toxic derivative e.g. salt thereof (as herein defined) adapted for use in human or veterinary medicine. Such compositions may be presented for use in conventional manner with the aid of any necessary pharmaceutical carriers or excipient.

The antibacterial compounds according to the invention may be formulated for injection and may be presented in unit dose form in ampoules, or in multidose containers with an added preservative. The compositions may take such forms as suspensions, solutions, emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The compositions may be presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinyl-pyrollidone; fillers, for example lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparation may be in the form of aqueous or oily suspensions, solutions, emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats, emulsifying agents, for example, lecithin, sorbitan monooleate or acacia, non-aqueous vehicles which may include edible oils, for example, almond oil, fractionated coconut oil, oly esters, propylene glycol, or ethyl alcohol; preservatives, for example, methyl or propyl p-hydroxybenzoates or sorbic acid. Suppositories will contain conventional suppository bases, e.g. cocoa butter or other glyceride.

The composition may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-liquid form, or may be used as drops etc. Topical applications may be formulated in hydrophobic or hydrophilic bases as ointments, creams, lotions, paints, powders etc.

For veterinary medicine the composition, may, for example, be formulated as an intramammary preparation in either long acting or quick-release bases.

The compositions may contain from 0.1% upwards, preferably from 10–60% of the active material, depending on the method of administration. Where the compositions comprise dosage units, each unit will preferably contain 50–500 mg. of the active ingredient. The dosage as employed for adult human treatment will preferably range from 100–3000 mg. for instance 1500 mg per day, depending on the route and frequency of administration.

The compounds according to the invention may be administered in combination with other therapeutic agents such as antibiotics, for example other cephalosporins, the penicillins or tetracyclines.

The following examples illustrate the invention.

PREPARATION 1

2-Methoxyiminophenylacetic acids (syn- and anti-isomers)

A solution of sodium (5 g.) in dry methanol (100 ml) was added to a solution of O-methylhydroxylamine hydrochloride (15 g.) in dry methanol (100 ml) until neutral to phenolphthalein. The precipitated sodium chloride was removed by filtration, and the filtrate added to a solution of phenylglyoxylic acid (25 g.) in dry methanol (100 ml). The solution was refluxed for 2 hours, cooled, and evaporated to an oil, which was dissolved in ether (200 ml), refiltered and evaporated to an oil (32.9 g.). This was crystallised from petroleum spirit, (bp. 60°–80°) producing a white solid (19.61 g.) and oil (3.9 g.).

The solid (17.8 g.) and the oil (3.9 g.) were combined (21.7 g.) and methylated with ethereal diazomethane, producing an oil (24.2 g.). This was purified by chromatography on silica gel (600 g.), producing syn-methyl 2-methoxyiminophenylacetate as an oil (13.6 g. 55%), $\lambda_{max}$. (EtOH) 259 nm ($\epsilon$ 10,400) and anti-methyl 2-methoxyiminophenylacetate, the slower component, as a solid (8.7 g.; 35%), m.p. 54°, $\lambda_{max}$. (EtOH) 251 nm ($\epsilon$ 7,260).

Methyl 2-methoxyiminophenylacetate (anti-isomer) (8.7 g.) was dissolved in methanol (100 ml) and 2N-sodium hydroxide solution (22 ml.) was added. The solution was stirred at room temperature for 1 hour, and the pH adjusted to 7 with 2N-hydrochloric acid. Methanol was removed by evaporation, water (150 ml.) was added, and the solution acidified to pH 1.5 with 2N-hydrochloric acid. The mixture was extracted with ethyl acetate (3 × 100 ml), the organic extracts were combined, dried and evaporated to give a solid (6.74 g.) which was crystallised from petroleum spirit (b.pt. 60°–80°): benzene, producing anti-2-methoxyiminophenylacetic acid (4.84 g.), m.p. 103°–104°, $\lambda_{max}$(EtOH) 248 nm ($\epsilon$ 7,010). $\tau$ (CDCl$_3$) values include 2.64 (Ph), 5.92 (CH$_3$).

Methyl 2-methoxyiminophenylacetate (syn-isomer) (13.6 g.) was hydrolysed in a similar manner, but the hydrolysis mixture was stirred for 40 hours at room temperature. The white solid (11.13 g.) formed was crystallised from petroleum spirit (b.pt. 60°–80°); benzene producing syn-2-methoxyiminophenylacetic acid as a white solid (10.02 g.). m.p. 96°–97°, $\lambda_{max}$. (EtOH) 255 nm, ($\epsilon$ 13,200), $\epsilon$ (CDCl$_3$) values include 2.2–2.8 (Ph), 5.92 (CH$_3$).

PREPARATION 2

2-Methoxyimino-(thien-2-yl)-acetic acids (syn- and anti-isomers)

A solution of methoxyamine hydrochloride (5.85 g.) in dry methanol (60 ml.) was neutralised (phenolphthalein) with a solution of sodium methoxide in methanol [from sodium (2.5 g.) and dry methanol (50 ml.)]. The precipitated sodium chloride was removed by filtration, and the filtrate was added to a solution of thien-2-ylglyoxylic acid (10 g.) in dry methanol (60 ml.). The resulting solution was refluxed for 1 hour, cooled, and evaporated to an oil. Ether (100 ml.) was added, the mixture was filtered, and the filtrate was evaporated to an oil (13.06 g.).

The oil (12.5 g.) was dissolved in ether (50 ml.) and an ethereal solution of diazomethane was added until a permanent yellow colour remained. The excess diazomethane was destroyed by leaving the solution in sunlight for 1 hour. Evaporation of this solution produced an oil (13.2 g.).

The oil (10.33 g.) was purified by preparative plate chromatography (Kieselgel) PF$_{254\ +\ 366}$) developing 3 times with 75% petroleum spirit (b.p. 60°–80°) in benzene, producing (a) methyl 2-methoxyimino-2(thien-2-yl)-acetate (syn isomer) (3.44 g., 27%), $\lambda$max.$^{EtOH}$ 290 nm ($\epsilon$ 11,250), $\lambda_{inf}$271 nm ($\epsilon$ 5,400) $\nu_{max}$. (CHBr$_3$) 1738 and 1230 cm$^{-1}$(CO$_2$Me). $\tau$ values (CDCl$_3$) include 6.06 (s, CO$_2$CH$_3$), 5.78 (s, OCH$_3$). (b) methyl 2-methoxyimino-2-(thien-2-yl)-acetate (anti-isomer) (1.21 g., 9.5%), $\lambda_{max}$. $^{EtOH}$ 221 and 288 nm ($\epsilon$ 5,020 and 11,000). $\theta_{max}$.(CHBR$_3$) 1732 and 1212 cm$^{-1}$(CO$_2$Me), $\tau$ (CDCl$_3$) values include 6.06 (s, CO$_2$Me), 6.00 (s, OCH$_3$) and further fractions which were isomeric mixtures.

2N-Sodium hydroxide (8.27 ml.) was added to a solution of methyl 2-methoxyimino-2-(thien-2-yl)-acetate (syn-isomer) (3.28 g.) in methanol (50 ml.) and the solution was stirred at room temperature for 18 hours.

Water (20 ml.) was added and the solution was evaporated to remove methanol, and then washed with ethyl acetate. The pH of the solution under ethyl acetate (50 ml.) was altered to 2 with 2N-hydrochloric acid. The layers were separated and the aqueous phase was extracted with ethyl acetate. The organic extracts were combined, dried, and evaporated to a white solid (2.58 g.). This was crystallised from cyclohexane, producing the title compound (syn-isomer) (2.23 g., 73%), m.p. 105.5°, $\lambda_{max.}^{EtOH}$ 289 nm ($\lambda$ 10,100), $\lambda_{inf.}$ 262 and 271 nm. ($\epsilon$ 7,750 and 8,150), $\tau$ (CDCl$_3$) values include 0.32 (OH) and 5.92 (OCH$_3$). Similar hydrolysis of the anti-methyl ester gave 2-methoxyimino-(thien-2-yl)acetic acid (anti-isomer) (0.85 g.), $\lambda_{max.}^{EtOH}$ 286–287 nm ($\epsilon$ 10,200), $\tau$ (CDCl$_3$) values include 1.31 (OH) and 5.73 (OCH$_3$).

PREPARATION 3 syn-t-Butoxyiminothien-2-ylacetic acid

A solution of thien-2-ylglyoxylic acid (6.2 g.) and sodium bicarbonate (3.36 g.) in water (100 ml.) was added dropwise to a stirred solution of t-butoxyamine hydrochloride (5.65 g.) and sodium bicarbonate (3.78 g.) in water (100 ml.) at 0°–5° and the mixture was stirred at room temperature for 18 hr. The mixture was acidified with 2N hydrochloric acid to pH 2.0 and extracted with ethyl acetate. The combined extracts were washed with water, dried and concentrated to give a solid (9.75 g.). Recrystallisation from petroleum (b.p. 60°–80°) gave the title compound (4.0 g., 44%), m.p. 106°–107°, $\lambda_{max.}$(EtOH)290 nm ($\epsilon$ 11,600), $\tau$ (CDCl$_3$) values include 2.46, 2.66, 2.98 (d doublets, thienyl protons), 8.60 (C(CH$_3$)$_3$).

PREPARATION 4

2-Ethoxyiminophenylacetic acids (syn and anti-isomers)

Ethoxamine hydrochloride (4.0 g.) and phenylglyoxylic acid (6.0 g.) were dissolved in water (50 ml.), and the resulting solution was basified to pH 4.5, and stirred at this pH for 15 hr. Acidification and extraction of the mixture gave, after evaporation of the ethyl acetate, a mixture of syn and anti ethoxyiminophenylacetic acids (7.4 g., 94%). Four recrystallisations from cyclohexane failed to give the pure syn acid. However, evaporation of the mother-liquors from the first crystallisation, and recrystallisation of the residue from cyclohexane gave anti-ethoxyiminophenylacetic acid (1.36 g., 17%), m.p. 90.9°–91.6°, $\lambda_{max.}$ (ethanol) 249 nm ($\epsilon$ 7,600), $\tau$ (DMSO-d$_6$) values include 2.52 (s, Ph) 5.74 (q, CH$_2$), 8.76 (t, —CH$_3$).

A solution of the mixed acids (4.0 g.) in ether (100 ml.) was treated with an ethereal solution of diazomethane until a yellow colour persisted. Acetic acid was added to destroy excess diazomethane and the ether solution was washed with sodium bicarbonate solution, water, and brine, then dried. Evaporation of the ether gave the methyl esters (4.1 g.) as an orange oil. These were separated on five 40 × 20 cm. preparative plates, eluting with petroleum spirit (b.p. 40°–60°)/ether (3:1). The slower band was eluted with chloroform, and removed of the solvent gave antimethyl 2-ethoxyiminophenylacetate (1.45 g.) as a pale-yellow oil; $\tau$ (CDCl$_3$) values include 2.58 (Ph), 5.66 (q, CH$_2$), 6.12 (s, OCH$_3$), 8.72 (t, CH$_3$). Similar treatment of the faster band gave syn-methyl 2-ethoxyiminophenylacetate (2.45 g.) as a pale yellow oil, $\tau$ (CDCl$_3$) values include 2.3–2.7 (m, Ph) 5.72 (q, CH$_2$), 6.06 (s, OCH$_3$), 8.67 (t, CH$_3$).

The above syn-methyl ester (2.39 g.) in methanol (60 ml.) was treated with sodium hydroxide solution (2N; 12 ml.), and the solution was stirred for 18 hr. The methanol, was removed, and the aqueous-mixture, after being acidified to pH 1.5, was extracted with ethyl acetate. The washed and dried extracts were evaporated to dryness, and the residue was recrystallised from cyclohexane to give syn-ethoxyiminophenylacetic acid (836 mg.), m.p. 77.9°–79.0°, $\lambda_{max.}$ (ethanol) 256.5 nm ($\epsilon$ 12,800); $\tau$ (DMSO-d$_6$) values include 2.48 (m, Ph), 5.74 (q, CH$_2$), 8.71 (t, CH$_3$).

PREPARATIONS 5–23

2-Alkoxyiminoarylacetic Acids

General Procedures

A mixture of the substituted glyoxylic acid and an excess (10 to 15%) of the alkoxyamine hydrochloride was suspended in water or aqueous ethanol, stirred, and the pH of the mixture adjusted to between 4 and 5 (Method B) with sodium hydroxide solution (N to 10N). A clear solution at pH 4 to 5 was maintained during the reaction by further additions of sodium hydroxide solution and ethanol as needed. The reaction mixture was kept at room temperature until all of the keto-acid was consumed (it may be necessary to add a further portion of the more volatile alkoxyamines). The progress of the reaction was followed by acidification of an aliquot, extraction with ethyl acetate and thin layer chromatography of the extract on silica plates (developed with a mixture of chloroform:methanol:acetic acid; 18:2.1). the alkoxyiminoacetic acids were less polar than the starting keto-acids. The reaction times were 2 hr. to 2 days. Reactions carried out at pH 7–8 are designated Method A. When reaction was complete the pH of the mixture was adjusted to between 7 and 8 and the ethanol (if any) was removed by evaporation. The aqueous mixture was extracted with ether, the extract discarded and the aqueous phase acidified to pH < 2 with dilute hydrochloric acid. The mixture was extracted with ethyl acetate, the extract dried and evaporated to give the crude product which was purified by one of the following methods:

(a) Crystallisation and recrystallisation (if needed) from a suitable solvent.

(b) The crude product dissolved in ether was treated with a small excess of a solution of diazomethane in ether. The excess reagent was destroyed with acetic acid and the solution washed with sodium bicarbonate solution and evaporated to give the crude methyl esters. The esters were separated by preparative thick layer chromatography or column chromatography on silica, and then hydrolysed conventionally with alkali to give the pure syn acid, (c) The mixture of methyl esters was prepared as in (b) and the isomers separated by crystallisation from a suitable solvent and similarly hydrolysed.

These methods were employed to prepare the intermediates listed in Table 1 (syn-isomers)

TABLE 1

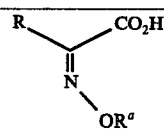

| Preparation No. | R | $R^a$ | Method | Purification | Mp.° | τ values R | (solvent) $R^a$ | $\lambda_{max.}$ nm (EtOH) | $\epsilon$ | Yield % (before purification) |
|---|---|---|---|---|---|---|---|---|---|---|
| 5 | Ph | $C(CH_3)_3$ | A | (a) | 127–129° | 2.2–2.7 (DMSO-$D_6$) | 8.62 | 257 | 13,060 | 100 |
| 6 | Ph | $CH_2Ph$ | A | (a) | 103.3° | 2.2–2.7 ($CDCl_3$) | 4.67 ($CH_2$) | 257 | 15,150 | 100 |
| 7 | Ph | ⟨S⟩-$CH_2$ | B | (a) | 110–111° | 2.44 (DMSO-$d_6$) | 4.58 ($CH_2$) 2.92,2.78,2.44 (thien-2-yl) | — | — | — |
| 8 | ⟨S⟩ | $CH_3$ | B | (a) | 108–109° | 2.61–2.91 ($CDCl_3$) | 5.92 | 289 | 10,700 | 911 |
| 9 | ⟨S⟩ | $C_2H_5$ | B | (a) | 89.5–91.5° | 2.29,2.76,2.86 (DMSO-$d_6$) | 5.79 ($CH_2$) 8.72 ($CH_3$) | 289.5 | 12,500 | 87 |

| Preparation No. | R | $R^a$ | Method | Purification | Mp.° | τ values R | (DMSO-$d_6$) $R^a$ | $\lambda_{max.}$ nm (EtOH) | $\epsilon$ | Yield % (before purification) |
|---|---|---|---|---|---|---|---|---|---|---|
| 10 | ⟨S⟩ | $CH_2Ph$ | B | (a) | 114–115° | 2.29,2.73,2.84 | 2.59 (Ph) 4.77 ($CH_2$) | 290 | 12,300 | 88 |
| 11 | ⟨S⟩ | $CH_2CH_2Br$ | B | (b) | 92.6° | 2.23;2.71;2.83 | 5.54;6.28 | 289 | 12,200 | 77 |
| 12 | naphthyl | $CH_3$ | B | (b) | 98–99° | 1.38 1.8–2.1 2.1–2.5 | 5.9 | 294.2 | 8,100 | 96 |
| 13 | naphthyl | $C(CH_3)_3$ | A | (b) | 122–123° | 1.3–1.5 1.3–2.1 2.2–2.5 | 8.62 | 296.5 | 9,300 | 96 |
| 14 | naphthyl | $CH_2Ph$ | A | (a) | — | 1.53,1.92,2.2–2.7 | 2.50 (Ph) 4.64 ($CH_2$) | 294 | 8,300 | 86 |
| 15 | ⟨O⟩ | $CH_3$ | B | (a) | 85–87° | 2.10,3.18,3.33 | 6.06 | 275 | 21,500 | 81 |
| 16 | ⟨O⟩ | $C(CH_3)_3$ | B | (a) | 110.5–111.5° | 2.12,3.24,3.35 | 8.70 | 275.5 | 16,040 | 95 |
| 17 | ⟨O⟩ | $CH_2Ph$ | B | (a) | 104–105.5 | 2.12,3.19,3.33 | 2.58 (Ph) 4.75 ($CH_2$) | 277 | 17,650 | 81 |
| 18 | benzothienyl | $CH_3$ | B | (c) | 129–130° | 1.40,1.83,1.95,2.44 | 5.92 | 233 284 296.5 306.5 | 22,900 10,900 10,500 9,270 | |
| 19 | benzothienyl | $C(CH_3)_3$ | B | (a) | 175–176° | 1.88,2.03,2.3–2.7 | 8.6 | 234 284.5 297 307.5 | 21,900 11,200 10,800 9,400 | 93 |
| 20 | benzothienyl | $CH_3$ | B | (a) | 143–144° (dec) | 2.00,2.36,2.56 | 6.00 | 231 252.5 296.5 | 5,400 7,300 23,600 | 98 |

TABLE 1-continued

| | | | | | | | | | |
|---|---|---|---|---|---|---|---|---|---|
| 21 | (thienyl) | CH₂Ph | B | (a) | 103–103.5° | 2.22,2.32,2.65 | 2.59 (Ph) 4.76 (CH₂) | 259 | 15,400 | — |
| 22 | (furyl)—CH₃ | (furyl) | B | (a) | 104.8–105.4° | 2.17;3.25; 3.40 | 4.92 (CH₂) 2.33,3.5 (furyl protons) | 276 | 16,300 | 97 |
| 23 | (furyl) | —C₂H₄ | B | (a) | 91–92° | 2.10,3.19, 5.79,8.25 | 5.79,274.5 | 15,800 | 92 |

PREPARATION 24

2-Methoxyiminopyrid-3'-ylacetic acid (syn- and anti-isomers)

Pyrid-3-ylglyoxylic acid (3.02 g.) and methoxylamine hydrochloride (2.59 g) were heated under reflux in ethanol (50 ml.) and treated with a solution of sodium ethoxide in ethanol until the mixture was just alkaline to phenophthalein. The mixture was maintained under reflux for 1½ hours. Further portions of methoxylamine hydrochloride (0.5 g) and ethanolic sodium ethoxide were added and refluxing continued for a further 1 hour. The resulting mixture was filtered through Kieselguhr and evaporated to dryness. The residue was dissolved in a small volume of ethanol and the remaining fine suspension was removed by filtration through Kieselguhr. Dilution of the filtrate with ethyl acetate gave a crystalline solid. The solid was washed well with ethyl acetate and dried to yield 2-methoxyiminopyrid-3'-ylacetic acid as an isomeric mixture (2.72 g., 76%), $\lambda_{max}$ (pH 6 buffer) 250 nm ($\epsilon$ 6,630), $\nu_{max}$ (Nujol) 1610 (CO₂116) and 1038 cm⁻¹ (=C—O—), $\tau$ (d₆DMSO) 1.21, 1.43, 2.02, 2.60 (multiplets; aromatic protons), 6.20 (s; OCH₃).

PREPARATION 25

(A) Methyl 2-(1-ethoxy)ethoxyimino-2-(thien-2-yl)acetate (syn-isomer)

To a stirred mixture of methyl 2-hydroxyimino-2-(thien-2-yl)acetate syn-isomer (3.98 g.) and ethyl vinyl ether (2.5 mls) in ethyl acetate (25 mls) was added phosphorus oxychloride (2 drops). After 20 mins. at 50° the ethyl acetate was washed with saturated sodium bicarbonate solution, dried over sodium sulphate and evaporated to an oil, giving methyl 2-(1-ethoxy)ethoxyimino-2-(thien-2-yl)acetate (syn-isomer) (5.7 g; 100%) $\lambda_{max}$ (EtOH) 289 nm ($\epsilon$ 11,700), $\tau$ (CDCl₃; 60 MHz) 2.61 (multiplet; thienyl H₅), 2.82 to 2.97 (multiplet; thienyl H₃ and H₄), 4.64 (quarter, J 5 Hz;

6.06 (singlet, —COOCH₃), 6.24 (quartet, J 7 Hz, OCH₂), 8.56 (doublet J 5 Hz; CH—C<u>H</u>₃), 8.79 (triplet, J 7 Hz; O.CH₂C<u>H</u>₃).

(b) 2-(1-Ethoxy)ethoxyimino-2-(thien-2-yl)acetic acid sodium salt (syn-isomer)

1N-Sodium hydroxide (1 equiv.) and enough methanol to form a homogeneous system were added to methyl 2-(1-ethoxy)ethoxyimino-2-(thien-2-yl)acetate (syn-isomer) (5.7 g.). After 4 hrs. at 50° the methanol was evaporated and the residue azeotroped with benzene/methanol giving a white solid, 2-(1-ethoxy)ethoxyimino-2-(thien-2-yl)acetic acid sodium salt syn-isomer) (4.6 g, 78.5%), $\lambda_{max}$ (pH 6 buffer) 287.5 nm ($\epsilon$ 10,650), $\tau$ (D₂O) values include 2.42 (multiplet; thienyl H₅), 2.68 to 2.84 (multiplet; thienyl H₃ and H₄), 4.63 (quartet, J 5 Hz;

6.21 (quartet, J 7 Hz; —C<u>H</u>₂—CH₃), 8.57 (doublet, J 5 Hz;

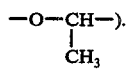

8.82 (triplet, J 7 Hz; —CH₂—C<u>H</u>₃).

PREPARATION 26 syn-Then-2-yloxyimino(thien-2-yl)acetic acid

Then-2-yloxamine hydrochloride (7.37 g.) and thien-2-ylglyoxylic acid (6.24 g.) were dissolved in ethanol (110 ml.) and water (20 ml.). The pH of the solution was adjusted to 5.0, and this solution was stirred for 22 hr. The ethanol was evaporated off, and the aqueous mixture was neutralised, washed twice with ether, then acidified to pH 1.5. The acid mixture was extracted with ethyl acetate. The combined extracts were washed, dried and evaporated to dryness to give a yellow oil (9.2 g., 86%) which crystallised on standing. TLC indicated the solid to be a mixture of isomers. Recrystallisation of this solid several times from cyclohexane effected no separation of isomers. The mixture of acids (5.0 g.) was esterified with diazomethane to give the mixture of methyl esters, as a pale-yellow oil.

To a solution of the mixture of methyl esters (2.14 g.) in methanol (50 ml.) was added 2N sodium hydroxide solution (7.6 ml.). After stirring this solution for 0.5 hr., the solution was neutralised. The methanol was evaporated and the aqueous residue was extracted with ethyl acetate. The extracts were washed, dried, and evaporated to dryness to give a yellow oil (1.0 g.). This oil was dissolved in methanol (25 ml.) and stirred for 18 hr. with 2N sodium hydroxide solution (5 ml.). Methanol was removed by evaporation and the aqueous residue, after washing with ethyl acetae then acidification to pH 1.7, was extracted with ethyl acetate. The extracts were washed, dried, and evaporated to dryness to give a solid (730 mg.). Recrystallisation of this solid twice from cyclohexane gave syn-then-2-yloxyimino(thien-2-yl)acetic acid (369 mg.), m.p. 101°–102°, $\lambda_{max}$ (EtOH), 239, 289.5 nm (ε 11,700, 12,300), τ (DMSO-d₆) values include 4.67 (s, CH₂).

PREPARATION 27 syn-2-Benzyloxyiminobenzo[b]-thien-3'-ylacetic acid

Benzo[b]-thien-3-ylglyoxylic acid (3.37 g) and benzyloxyamine hydrochloride (1.915 g) were dissolved in ethanol (70 ml) and water (30 ml). The solution was adjusted to pH 4.5 with 40% w/v sodium hydroxide solution and stirred at this pH for 2 hr. The solution was stood overnight and adjusted to pH 9 then washed with either. The aqueous phase was acidified under ethyl acetate and the organic layer was washed with water, saturated brine and dried. Evaporation gave a mixture of syn and anti-isomers as a buff crystalline solid (3.4 g., 99%). The crude acid in ether was treated with excess diazomethane in ether at 0°-5°. The excess reagent was destroyed with acetic acid and the ether solution was washed with sodium bicarbonate, water and dried. Evaporation gave a pale brown oil (3.34 g., 93%). the crude product in methanol (100 ml.) was treated with sodium hydroxide solution (1N, 10 ml) at room temperature for 1 hr. The hydrolysis was followed by thin layer chromatography on silica. Hydrochloric acid (2N 5 ml.) was added to stop the hydrolysis and methanol was removed by evaporation. Ethyl acetate was added and the anti-2-benzyloxyimino benzo[b]-thien-3'-ylacetic acid was removed by washing with sodium bicarbonate. The ethyl acetate layer was washed with water and dried and evaporated to a pale orange oil (1.99 g., 56%). This was treated in methanol (90 ml.) with sodium hydroxide (1N; 10 ml) at room temperature for 7 hr. A further aliquot of sodium hydroxide (1N; 5 ml) was added and the solution stood for 2 days to complete hydrolysis. The methanol was removed by evaporation and the residue dissolved in ethyl acetate and water. The mixture was adjusted to pH 1.5 and the ethyl acetate layer was washed with water, saturated brine and dried. Evaporation gave yellow crystals (1.82 g, 50%) Crystallisation from a mixture of benzene and cyclohexane gave the title compound as pale orange crystals (1.29 g., 36%), m.p. 120.5°-121°, λ$_{max}$ (EtOH) 232, 285.5, 296.5, 306.5 nm. (ε 22,500, 11,800, 11,500, 10,400), τ values (DMSO-d₆) include 1.90, 197, 2.3-2.7 (aromatic protons), 4.64 (CH₂ singlet).

PREPARATION 28 syn-2-Benzyloxyiminobenzo-[b]-thien-2'-ylacetic acid

Benzo[b]-thien-2-ylglyoxylic acid (3.092 g) and benzyloxyamine hydrochloride (2.72 g.) in ethanol (170 ml.) and water (70 ml.) were adjusted to pH 4.5 with sodium hydroxide (40%). the solution was stirred at this pH at room temperature for 6 hr. Benzyloxyamine hydrochloride (500 mg.,) was added and the solution stood at room temperature overnight. The solution was adjusted to pH 8 and washed with ether. The aqueous phase was acidified under ether to pH 1.5. The ether layer was washed with water and dried. Evaporation gave a cream coloured solid (4.28 g. 91%) as an isomeric mixture.

The crude isomeric mixture was treated in ether with excess diazomethane in ether at b 0°-5°. The excess reagent was destroyed with acetic acid and the ether solution was washed with sodium bicarbonate, water and dried. Evaporation gave an oil (4.45 g., 91%). This was dissolved in methanol (140 ml.) and treated at room temperature with sodium hydroxide solution (1N; 14 ml.) for 2¼ hr. Hydrochloric acid (2N, 7 ml.) was added and the alcohol was removed by evaporation. The aqueous phase was partitioned between sodium bicarbonate solution and ether. The ether layer was washed with water and dried. Evaporation gave an oil (2.16 g., 44%). This was hydrolysed directly in refluxing methanol (70 ml.) with sodium hydroxide (1N; 7 ml) for 4 hr. The methanol was removed by evaporation and the residue partitioned between water and a little ether. The aqueous layer was acidified under ether to pH 1.5 and the ether layer was washed with water, dried and evaporated to give a pale cream solid (1.97 g, 42%). Crystallisation from a mixture of benzene and cyclohexane gave the title compound as a white crystalline solid, (1.61 g; 35%), m.p. 141°-143° (dec.), λ$_{max}$ (EtOH) 230.5, 253, 297.5 nm (ε 16.400; 7,400; 24,100); τ (DMSO-d₆) values include 2.00, 2.36, 2.55 (aromatic protons), 4.71 (CH₂ singlet).

PREPARATION 29

(2-t-Butoxycarboxamido)ethoxyimino-thien-2-ylacetic acid (syn-isomer)

N-Carbo-t-butoxy-2-bromoethylamine (1.12 g.) was added to a solution of the sodium salt of methyl synhydroxyimino-thien-2-ylacetate (1.035 g.) in benzene: dimethylformamide (2:1 v/v, 30 ml.), and the mixture was stirred for 16 hr. Ethyl acetate (50 ml.) was added, and the mixture was washed several times with water, dried, and evaporated to dryness to give methyl syn-(2-t-butoxycarboxamidoethoxy)imino-thien-2-ylacetate (1.21 g, 75%); τ (CDCl₃) values include 2.62, 2.86, 2.99 (thienyl protons), 5.10 (NH), 6.06 (s, CH₃) 8.58 (s, C(CH₃)₃).

The crude ester (1.1 g) in methanol (20 ml) was treated with 2N sodium hydroxide solution (3.4 ml.), and stood 16 hr. The methanol was evaporated off, and the aqueous residue, after washing with ether, was acidified to pH 2.0, and extracted with ethyl acetate. The extracts were washed (water, saturated brine), dried, and evaporated to dryness. Recrystallisation of the residue from cyclohexane gave the title compound (951 mg., 90%), m.p. 112.8°-114.4° λ$_{max}$ (EtOH) 290.5 nm. (ε 11,600), τ (DMSO-d₆) values include 2.19, 2.6–2.9 (thienyl protons), 3.14 (NH), 8.52 (s, C(CH₃)₃).

The alkylating agent used for the above preparation was made as follows:

(b) N-Carbo-t-butoxy-2-bromoethylamine

A mixture of t-butyl azidoformate (15.81 g) and triethylamine (30 ml) was added dropwise to a stirred suspension of 2-bromoethylamine hydrobromide (20.5 g.); in methylene chloride (100 ml.). The mixture was stirred for 3 hr., then filtered. The filtrate was concentrated to a small volume, and the residue was distributed between ether and water. The ether layer was dried, then distilled under reduced pressure, collecting the fraction b.p. 92°-94°/0.9 mm as N-carbo-t-butoxy-2-bromoethylamine (1.756 g.)

PREPARATION 30

Pyrid-2-ylmethoxyimino(thien-2-yl)acetic acid (syn-isomer)

2-Chloromethylpyridine (a 25% solution in toluene, 2.8 ml.) was added to a solution of the sodium salt of methyl syn-hydroxyimino-thien-2-ylacetate (1.035 g.) in benzene:dimethylformamide (30 ml, 2:1, v/v). The solution was stirred for 18 hr., ethyl acetate (50 ml.) was added, and the mixture was washed several times with water, dried and evaporated to dryness to give a dark-green oil (1.4 g.). This oil was chromatographed on two 40 × 20 cm. preparative chromatography plates, eluting with chloroform. The single major band was eluted off the silica with chloroform:ethanol (9:1 v/v) to give after evaporation of the solvent, methyl pyrid-2-ylmethoxyimino(thien-2-yl)acetate (889 mg., 47%) (75% syn, 25% anti-siomer). A solution of the crude ester (828 mg.) in methanol (20 ml) and 2N sodium hydroxide solution (3 ml.) was stood 16 hrs. After removal of the methanol, the aqueous mixture was acidified to pH 2.0 in the presence of methylene chloride. The acid mixture was extracted with methylene chloride and the extracts were washed (water, brine), dried, and evaporated to dryness. Trituration of the residue with ether gave the title compound (210 mg. 27%), m.p. 152.1°–152.9°, $\lambda_{max}$ (EtOH) 260.5, 266, 289 nm ($\epsilon$ 12,300; 12,000; 11,700), $\tau$ (DMSO-$d_6$) values include 4.66 (singlet, $CH_2$).

PREPARATION 31 n-Butoxyimino-thien-2-ylacetic acid(syn-isomer)

1-Bromobutane (0.6 ml.) was added to a solution of methyl syn-hydroxyimino-thien-2-ylacetate sodium salt (prepared by treating methyl syn-hydroxyimino-thien-2-ylacetate with 1 equivalent sodium methoxide) (1.0 g.) in benzene:dimethylformamide (2:1; 15 ml.) and the mixture was stirred for 17 hours at room temperature then poured into water. The aqueous solution was extracted with ethyl acetate, washed with water, dried and evaporated to give syn methyl ester (0.88 g.) as a pale yellow oil.

2N-Sodium hydride (4.0 ml.) was added to a solution of the syn methyl ester (0.85 g.), in methanol (10 ml.) and the mixture was left at room temperature for 18 hr. The methanol was removed by evaporation; the aqueous residue was diluted with water, washed with ether and acidified to pH 2.0 with 2N-hydrochloric acid. The mixture was extracted with ethyl acetate; the combined extracts were washed with water, dried and evaporated to give the title compound (0.74 g., 81%) as a pale yellow oil, $\tau$ values (DMSO-$d_6$) include 2.30 2.7–3.0 (thien-2-yl protons), 5.84 ($OCH_2$), 9.10 ($CH_3$).

PREPARATION 32

2-Methoxymethoxyimino-(thien-2-yl)acetic acid (syn-isomer)

A solution of sodium methoxide in methanol (approx. 0.2 M) was added to methyl 2-hydroxyimino-2-(thien-2-yl) acetate (syn-isomer) (0.5 g.) and the solution formed was evaporated to a yellow oil which on azeotroping with petrol (b.p. 40°–60°) gave the sodium salt of methyl 2-hydroxyimino-2-(thien-2-yl) acetate (syn-isomer) (0.49 g. 88%). To a stirred solution of the sodium salt (0.49 g.) in benzene/DMF (5 mls., 2:1). was added chlorodimethyl ether (0.22 mls.). After 10 mins. the reaction was poured into saturated sodium bicarbonate solution and extracted with benzene. The combined extracts were washed with water, dried over sodium sulphate and evaporated to a yellow oil, methyl 2-methoxymethoxyimino-(thien-2-yl) acetate (syn-isomer) (0.62 g.; 100%), $\lambda_{max}$ (EtOH) 288 nm ($\epsilon$ 10,300), $\nu_{max}$(CHBr$_3$) 1730 (COOCH$_3$), 1660 cm.$^{-1}$(—C=N—), $\tau$ (CDCl$_3$) values include 2.61–2.83 (multiplet, thien-2-yl), 4.83 (singlet, $CH_2$), 6.06 ($CO_2CH_3$) 6.56 (singlet, $CH_2OCH_3$).

A solution of sodium hydroxide (4 ml, 2N) and methanol were added to the methyl ester (0.4 g.). After 30 mins. the reaction was poured into water and washed with ethyl acetate. The aqueous layer was acidified to pH 1 using 2N-hydrochloric acid and extracted with ethyl acetate. The ethyl acetate was dried and evaporated to a colourless oil which was azeotroped with petrol (bp. 40°–60°) to yield a white solid, syn 2-methoxymethoxyimino-(thien-2-yl)acetic acid (0.21 g; 55%), m.p. 61.2°, $\lambda_{max}$ (EtOH) 286 nm ($\epsilon$ 10,400), $\nu_{max}$ (Nujol) 1732, 2600 cm.$^{-1}$ (CO$_2$H) $\epsilon$ (DMSO-$d_6$) 2.26 (multiplet; thienyl H$_5$), 2.7–2.9 (multiplet, thienyl H$_3$ and H$_4$), 4.88 (singlet, O—CH$_2$—), 6.6 (singlet, OCH$_3$).

PREPARATION 33

2-t-Butoxyiminobenzo[b]-thien-2'-ylacetic acid (syn-isomer)

Benzo[b]-thien-2-ylglyoxylic acid (3.09 g) and t-butoxyaminohydrochloride (1.98 g) were dissolved in 50% aqueous ethanol (100 ml). The solution was adjusted to pH 4.5 with sodium hydroxide solution and maintained at such for 4 hr. at room temperature. Thin-layer chromatography showed incomplete reaction. t-Butoxyaminohydrochloride (500 mg.) was added and the solution kept at room temperature overnight. The alcohol was removed by evaporation and the aqueous phase adjusted to pH 8 and washed with ether. The aqueous phase was then acidified to pH 1.5 under ether. The ether solution was washed with water and dried. Evaporation gave a cream solid (4.05 g.). Fractional crystallisation from cyclohexane gave the anti-isomer of the title compound (1.6 g.). The mother liquors were combined and evaporated to give a cream solid (2.11 g.) that was treated in ether with excess diazomethane in ether at 0°–5°. The excess reagent was destroyed by acetic acid and the ether solution washed with sodium bicarbonate, water and dried. Evaporation gave an oil (1.75 g). This was dissolved in methanol (70 ml) and treated with sodium hydroxide solution (N: 7 ml.) at room temperature for 3 hr. Hydrochloric acid (2N: 3.5 ml) was added and the methanol was removed by evaporation. The aqueous residue was partitioned between ether and sodium bicarbonate solution. The ether layer was washed with water and dried. Evaporation gave an oil (0.92 g.) that was dissolved in methanol (20 ml.) and treated with sodium hydroxide (N: 7 ml) at reflux temperature for 3 hr. Sodium hydroxide (N: 5 ml) was added and the solution refluxed for 6 hr. The methanol was removed by evaporation and the residue partitioned between ether and water. The aqueous phase was acidified (pH 1.5) under ether and the ether layer washed with water, dried and evaporated to give a pale orange crystalline solid (760 mg. 18%). Crystallisation from benzene containing cyclohexane gave syn-t-butoxyiminobenzo[b]-thien-2-ylacetic acid (430 mg.) m.p. 108°–9°, $\lambda_{max}$ (EtOH) 231, 253, 297 nm ($\epsilon$ 17,000, 7,240, 24,500).

PREPARATION 34

Benzo[b]-thien-2-ylglyoxylic acid and

Benzo[b]-thien-3-ylglyoxylic acid

A mixture of 2- and 3-acetylbenzo[b]-thiophene (ca. 1:1) (11.0 g.) in pyridine (80 ml.) was warmed to 60° with vigorous stirring and selenium dioxide (9.92 g.) was added portionwise. The mixture was heated to 110° C and an exothermic reaction occurred, the temperature rising to 120°. The reaction was stirred at 90° for 45 mins. and then left to cool. Water (80 ml.) was added and the mixture filtered through a kieselguhr pad. The pyridine was removed by evaporation and the aqueous residue again filtered. The filtrate was acidified to pH 2 under ether with 40% orthophosphoric acid (40 ml).

The aqueous phase was extracted with ether and the ether fractions were combined, washed with water and dried. Evaporation gave an orange crystalline solid (b 11.0 g., 86%). Crystallisation from benzene (100 ml) gave bright yellow crystals of benzo[b]-thien-2-ylglyoxylic acid (b 2.3 g. 18%), m.p. 175.9°, $\lambda_{max}$. (EtOH), 233, 247, $\lambda$ infl. 308 nm. ($\epsilon$ 11,400; 7,200; 14,600), $\tau$ (DMSO-$d_6$) values include 1.83 (C-4 and C-7 protons), 1.42 (C-3 proton), 2.40 (C-5 and C-6 protons).

The mother liquor was concentrated to an orange oil which crystallised on standing (8 g.). Recrystallisation from benzene (20 ml.) gave pale yellow needles of benzo-[b]-thien-3-ylglyoxylic acid (1.6 g., 2.5%), m.p. 92°–93°, $\tau$ (DMSO-$d_6$) values include 0.83 (C-2 protons), 1.32 (C-4 proton), 1.79 (C-7 proton), 2.40 (C-5 and C-6 protons), $\lambda_{max}$. (EtOH) 235, 310.5 nm ($\epsilon$ 11,200 and 7,400).

2-ALKOXYIMINOARYLACETYL CHLORIDES

PREPARATION 35 syn-2-Methoxyiminophenylacetyl chloride

Phosphorous pentachloride (5.21 g) was added in portions to a stirred suspension of syn-2-methoxyiminophenylacetic acid (4.51 g.) in dry benzene (20 ml.). Thionyl chloride (0.3 ml) was added to the solution, which was refluxed for 30 minutes. Benzene was removed by evaporation, and the residue distilled, producing a mixture of syn- and anti-acid chlorides (ca. 1:1) as a colourless oil (3.08 g., 62%), b.p. 74° (0.01 mm). A repeat of this reaction (on 5.04 mmole) at room temperature also produced a mixture of the isomeric acid chlorides.

The acid chlorides were separated and purified by preparative plate chromatography, developing three times with petroleum spirit (b.p. 60°–80°) producing the title compound as a colourless oil (1.43 g. 24%).

In a further experiment a mixture of syn- and anti-2-methoxyiminophenylacetic acids (10 g., ca 1:1) were converted to a mixture of acid chlorides as above and chromatographed on silica gel (120 g., Hopkins and Williams, MFC) using petroleum spirit (b.p. 60°–80°) to give syn-2-methoxyiminophenylacetyl chloride (4.32 g., 39%).

GENERAL METHOD FOR CONVERTING A 2-ALKOXYIMINOARYLACETIC ACID INTO ITS ACID CHLORIDE WITHOUT ISOMERISATION

A solution of the pure syn- or 2-alkoxyiminoarylacetic acid (1 equiv.) in methanol (ca. 2–4 ml./mmole.) was treated with sodium methoxide (1 equiv.) in methanol at 0°–25° and the mixture evaporated to give the sodium salt which may be dried by azeotroping with several portions of benzene and/or drying in vacuo over phosphorus pentoxide.

The anhydrous sodium salt (1 equiv.) is suspended in dry benzene (ca. 5 ml/mmole) containing a few drops of dry dimethylformamide and treated with freshly distilled oxalyl chloride (1–2.5 equiv.). The mixture is stirred at room temperature for 1 hr. and then evaporated to remove benzene. The resulting acid chlorides were not characterized but were dissolved in acetone or methylene chloride and used immediately to acylate the appropriate cephalosporin nucleus.

The following acids were converted into their acid chlorides in this way:
Syn-2-Ethoxyiminophenylacetic acid,
Syn-2-t-Butoxyiminophenylacetic acid,
Syn-2-Benzyloxyiminophenylacetic acid,
Syn-2-Then-2'-yloxyiminophenylacetic acid,
Syn-2-Methoxyimino-(thien-2-yl)acetic acid,
Syn-2-Ethoxyimino-(thien-2-yl)acetic acid,
Syn-2-Benzyloxyimino-(fur-2-yl)acetic acid,
Syn-2-n-Butoxyimino-(thien-2-yl)-acetic acid,
Syn-2-t-butoxyimino-(thien-2-yl)-acetic acid,
Syn-2-(2-Bromoethoxy)imino-(thien-2-yl)-acetic acid,
Syn-2-(2-t-Butoxycarbonylaminoethoxy)imino-(thien-2-yl)acetic acid,
Syn-2-Benzyloxyimino-(thien-2-yl)acetic acid,
Syn-2-Then-2'-yloxyimino-(thien-2-yl)-acetic acid,
Syn-2-(1-Ethoxy)ethoxyimino-(thien-2-yl)-acetic acid,
Syn-2-(Pyrid-2-ylmethyl)-oxyimino-(thien-2-yl)acetic acid,
Syn-b 2-Methoxyiminonaphth-1'-ylacetic acid,
Syn-2-t-Butoxyiminonaphth-1-ylacetic acid,
Syn-2-Benzyloxyiminonaphth-1'-ylacetic acid,
Syn-2-Methoxyiminobenzo-[b]-thien-3'-ylacetic acid,
Syn-2-t-Butoxyiminobenzo-[b]-thien-3'-ylacetic acid,
Syn-2-Benzyloxyiminobenzo-[b]-thien-3'-ylacetic acid,
Syn-2-Methoxyiminobenzo-[b]-thien-2'-ylacetic acid,
Syn-2-t-Butoxyiminobenzo[b]-thien-2'-ylacetic acid,
Syn-2-Benzyloxyiminobenzo-[b]-thien-2'-ylacetic acid,
Syn-2-Methoxyimino(fur-2-yl)acetic acid,
Syn-b 2-t-Butoxyimino-(fur-2-yl)acetic acid,
Syn-2-Benzyloxyimino-(fur-2-yl)-acetic acid,
Syn-2-Furfuryloxyimino-(fur-2-yl)-acetic acid, and
Syn-b 2-ethoxyimino-(fur-2-yl)-acetic acid.

PREPARATION A

Then-2-yloxamine hydrochloride (used as a starting material in Preparation 7)

(a) N-(Then-2-yloxy)phthalimide

Anhydrous potassium carbonate (11.04 g.) was added to a stirred suspension of N-hydroxyphthalimide (17.12 g.) in dry dimethyl sulphoxide (200 ml.). A brown colour developed, 2-Chloromethylthiophene (28.5 g.) was added dropwise and the mixture was stirred for 16 hr., during which time the colour disappeared. The suspension was poured into water (800 ml.) and cooled to 5°. The white precipitate was filtered off and recrystallised from ethanol to give colourless needles of N-(then-2-yloxy)phthalimide (23.4 g., 83%), m.p. 129.7°–130.9° $\tau$ values (DMSO-$d_6$) are 4.58 (CH$_2$), 2.28, 2.68, 2.90 (thienyl protons) 2.08 (phthalimide protons).

(b) Then-2-yloxamine hydrochloride

A mixture of N-(then-2-yloxy)phthalimide (22.4 g.) 100% hydrazine hydrate (5 g) and ethanol (600 ml.) was heated under reflux for 2 hours. Initially, a yellow solution was formed, but soon solid began to precipitate. The mixture was cooled, then acidified with concentrated hydrochloric acid (12 ml.). The precipitated phthalhydrazide was filtered off and washed with ethanol (3 × 50 ml.) and water (100 ml.). The combined filtrate and washings were evaporated to dryness, and the residue, suspended in water, was basified with 2N sodium hydroxide solution. The basic mixture was extracted with ether, and the combined extracts were washed (water, saturated brine), dried, and saturated with dry hydrogen chloride. The precipitated solid was collected and well washed with ether to give then-2-yloxamine hydrochloride, (12.45 g., 87%), m.p. 157.1°–157.5°. A sample recrystallised from ethanol/ether had m.p. 161.7°–162.1° $\tau$ values (DMSO-$d_6$) include 4.69 (CH$_2$), 2.30, 2.72, 2.90 (thienyl protons).

PREPARATION B

Furfuryloxamine Hydrochloride (used as a starting material in Preparation 22)

(a) N-Furfuryloxyphthalimide

To a stirred mixture of N-hydroxyphthalimide (41 g.), anhydrous potassium carbonate (26.4 g.) and dry dimethyl sulphoxide (400 ml.) was added 2-chloromethylfuran (freshly prepared, but undistilled, from 46.2 g. furfuryl alcohol according to the method of W. R. Kirner JACS, 1928, 50, 1955). The mixture was stirred for 18 hr., then poured into water (1.5l). The precipitated solid was filtered off, washed well with water, and recrystallised from ethanol to give N-furfuryloxyphthalimide (42.8 g., 70%), m.p. 145.3°–146.2° $\tau$ values (DMSO-$d_6$) are 4.80 (CH$_2$), 2.22, 3.30, 3.50 (furyl protons) 2.08 (phthalimide protons). (b) Furfuryloxamine Hydrochloride.

100% Hydrazine hydrate (20 ml.) was added to a stirred solution of N-furfuryloxyphthalimide (42.0 g.) in methylene chloride (600 ml.) A copious precipitate formed immediately, and the mixture was stirred for 45 min. 5N Ammonium hydroxide solution (500 ml.) was added to dissolve the precipitate, the two layers were separated, and the aqueous layer was washed twice with methylene chloride. The combined methylene chloride extracts were washed (saturated brine) and dried. Methylene chloride was evaporated off, and the residual liquid was dissolved in ether (250 ml.) Dry hydrogen chloride was passed into this solution for 1 hour. The precipitated solid was filtered off, washed with ether, dried, and recrystallised from isopropanol to give furfuryloxamine hydrochloride (12.89 g., 50%), m.p. 135°–136° (decomp) $\tau$ values (DMSO-$d_6$) include 4.87 (CH$_2$), 2.20, 3.27, 3.44 (furyl protons).

PREPARATION C

The general procedures described in Preparations 5–23 for the preparation of 2-alkoxyiminoarylacetic acids were employed to prepare the intermediates listed in tabular form below (the Table may be regarded as a continuation of Table 1).

| Preparation No. | R | R$^a$ | Method | Purification | Mp.° | $\tau$ values (DMSO-$d_6$) R | R$^a$ | $\lambda_{max}$ nm (EtOH) | $\epsilon$ | Yield % |
|---|---|---|---|---|---|---|---|---|---|---|
| 36 | Ph | n-C$_4$H$_9$ | B | (b) | oil | 2.4–2.6 | 5.82, 2.3–2.8, 9.08 | 257 | 11,500 | 100 |
| 37 | Ph | n-C$_3$H$_7$ | B | (b) | oil | 2.48 | 5.88, 8.40, | 257 | 11,400 | 100 |
| 38 | (thienyl) | —C$_2$H$_5$ | B | (a) | 74.0° | 2.2–2.4, 2.65 | 5.81, 8.75 | 258.5 | 13,800 | 96 |
| 39 | (benzofuranyl) | —C$_2$H$_5$ | B | (a) | 125.5–126° | 2.1–2.8, 2.75 | 5.69, 8.71 | 228 inf 290 297 307 | 7,200 22,940 24,600 22,500 | |

Structure above table: R–C(=N–OR$^a$)–CO$_2$H

2-Alkoxyiminoarylacetyl Chloride (continued)

The following acids were converted into their acid chlorides using the general method for converting a 2-alkoxyimino arylacetic acid into its acid chloride without isomerisation described immediately after preparation 35:

Syn-2-Butoxyiminophenylacetic acid
Syn-2-Isopropoxyiminophenylacetic acid
Syn-2-Propoxyiminophenylacetic acid
Syn-2-Propoxyimino-(thien-2-yl)acetic acid
Syn-2-Ethoxyimino (benzo[b]-fur-2-yl)acetic acid
Syn-2-Ethoxyimino-(thien-3-yl)acetic acid.

PREPARATION 40

2-Phenoxyimino-2-phenylacetic acid (syn-isomer)

A solution of syn-2-hydroxyimino-2-phenylacetic acid (33 g) in dry methanol (500 ml) was treated with 1.105 N sodium methoxide solution (486 ml), and stirred for 15 minutes. To the solution was added diphenyliodonium bromide (90 g), and the resulting mixture was stirred for 18 hours under nitrogen. A small amount of solid was filtered off, and the filtrate was evaporated to dryness. Water (600 ml) and ether (600 ml) were added to the residue, and the pH of the mixture was adjusted to 7.0 with concentrated hydrochloric acid. The aqueous layer was washed twice with ether, and then acidified under ether to pH 1.8 with concentrated hydrochloric acid. The acid mixture was extracted into ether, and the combined extracts were washed (water, saturated brine), dried, and evaporated to give a dark brown solid (ca 35 g). This solid was triturated with ice-cold nitromethane. The solid was collected, washed with a little cold nitromethane, and dried in vacuo to give fawn crystals of the title acid (24.41 g, 51%), m.p. 104.8°–105.1° $\lambda_{max}$ (ethanol) 267.5, 285 mm ($\epsilon$ 11,600; 10,100).

Similarly were prepared:

PREPARATION 41

2-Phenoxyimino-2-(thien-2-yl)acetic acid (syn-isomer) (52%) m.p. 98.3°–99.5°, $\lambda_{max}$ (ethanol) 267.5, 303 nm. ($\epsilon$ 9,900; 12,000). and

PREPARATION 42

2-Phenoxyimino-2-(fur-2-yl)acetic acid (syn-isomer) (34%), m.p. 100.7°–100.9°, $\lambda_{max}$ (ethanol) 270.5, 292.5 nm ($\epsilon$ 14,300; 15,700).

PREPARATION 43

2-Cyclopentyloxyimino-2-(fur-2-yl)acetic acid (syn-isomer)

Fur-2-ylglyoxylic acid (2.80 g) and cyclopentyloxamine hydrochloride (3.3 g) were dissolved in a mixture of water (100 ml) and ethanol (50 ml), and the pH of the solution was adjusted to 5.0. The solution was stirred for 19 hours, the alcohol was evaporated off, and the solution was acidified to pH 1.5 under ethyl acetate. The acid mixture was extracted into ethyl acetate, and the combined extracts were washed, dried, and evaporated to give the crude acid (4.38 g). This acid was treated with charcoal in benzene for 15 minutes, filtered, and the filtrate was evaporated to give a solid, which was recrystallised twice from cyclohexane to give the title acid (2.28 g, 51%), m.p. 96.6°–97.7°, $\lambda_{max}$ (ethanol) 277.5 nm ($\epsilon$ 15,600).

PREPARATIONS 44–50

2-Alkoxyimino-2-arylacetic acids

General Procedures

A mixture of the substituted glyoxylic acid and an excess (10 to 15%) of the alkoxyamine hydrochloride was suspended in water or aqueous ethanol, stirred, and the pH of the mixture adjusted to between 4 and 5 with sodium hydroxide solution (N to 10N). A clear solution at pH 4 to 5 was maintained during the reaction by further additions of sodium hydroxide solution and ethanol as needed. The reaction mixture was kept at room temperature until all of the keto-acid was consumed (it may be necessary to add a further portion of the more volatile alkoxyamines). The progress of the reaction was followed by acidification of an aliquot, extraction with ethyl acetate and thin layer chromatography of the extract on silica plates (developed with a mixture of chloroform:methanol:acetic acid; 18:2:1). The alkoxyiminoacetic acids were less polar than the starting keto-acids. The reaction times were 2 hours to 2 days. When reaction was complete the pH of the mixture was adjusted to between 7 and 8 and the ethanol (if any) was removed by evaporation. The aqueous mixture was extracted with ether, the extract discarded and the aqueous phase acidified to pH <2 with dilute hydrochloric acid. The mixture was extracted with ethyl acetate or ether, the extract dried and evaporated to give the crude product which was purified by one of the following methods:

(a) Crystallisation and recrystallisation (if needed) from a suitable solvent.

(b) The crude product dissolved in ether was treated with a small excess of a solution of diazomethane in ether. The excess reagent was destroyed with acetic acid and the solution washed with sodium bicarbonate solution and evaporated to give the crude methyl esters. The esters were separated by preparative thick layer chromatography or column chromatography on silica, and then hydrolysed conventionally with alkali to give the syn acids, which were purified by crystallisation from a suitable solvent.

These methods were employed to prepare the intermediates listed in Table 4 (syn-isomers).

TABLE 4

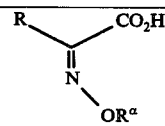

| Preparation No. | R | $R^a$ | Purification (solvent) | Mp° | τ values (DMSO-d6) R | τ values (DMSO-d6) $R^a$ | $\lambda_{max}$ nm (EtOH) | $\epsilon$ |
|---|---|---|---|---|---|---|---|---|
| 44 | (S-furyl) | cyclopentyl | (b) (cyclohexane) | 71.2 | 2.30, 2.7–3.0 | 5.25, 7.9–8.6 | 291.5 | 10,900 |
| 45 | (benzofuryl) | —C(CH₃)₃ | (a) (cyclohexane) | 124.5–125.5 | 2.1–2.45, 2.45–2.85, 2.78 | 8.66 | 232.5, 296, 307.5 | 6,700, 25,400; 23,500 |
| 46 | (N-methylpyrrolyl) | —CH₃ | (a) (benzene) | 114–115 | 3.03, 3.77, 3.92, 6.16 | 6.24 | 286 | 16,200 |
| 47 | (N-methylpyrrolyl) | —C(CH₃)₂ | (a) (benzene) | 146–147 | 3.00, 3.75, 3.90, 6.16 | 8.66 | 284 | 16,000 |
| 48 | Ph | cyclopentyl | (b) (cyclohexane) | 93.3 | 2.49 | 5.18 8.0–8.6 | 259 | 14,000 |
| 49 | (N-substituted pyrrolyl, CH₃, OCH₃Ph) | CH₃ | (b) (cyclohexane/ benzene) | 84–86 | 2.68(Ph), 2.78, 3.62, 3.78, 4.82, 5.47 | 6.14 | 285 | 12,400 |
| 50 | Ph | CH₂CO₂Bu$^t$ | (a) (carbon) | 88.5 | 2.47 | 5.32(CH₂) 8.58(Bu$^t$) | 253 | 13,800 |

TABLE 4-continued $$\underset{N}{\overset{R}{\underset{\|}{\diagup}}\overset{CO_2H}{\diagdown}}$$
$$\underset{OR^a}{\diagdown}$$

| Preparation No. | R | $R^a$ | Purification (solvent) | Mp° | τ values (DMSO-d6) R | $R^a$ | $\lambda_{max}$ nm (EtOH) | ε |
|---|---|---|---|---|---|---|---|---|
| | | | tetrachloride | | | | | |

PREPARATION 51

2-(Thien-2-ylmethoxyimino)-(1-methylpyrrol-2-yl)acetic acid (syn-isomer)

A solution of 1-methylpyrrol-2-ylglyoxylic acid (4.6 g) and thien-2-ylmethoxamine hydrochloride (5.46 g) in aqueous ethanol (100 ml, 1:1) was adjusted to pH 4.8 with 10N-sodium hydroxide solution and stirred at pH 4.8 for 24 hours at room temperature. A further portion of thien-2-ylmethoxamine (0.5 g) was added and the solution was maintained at pH 4.8 and room temperature for a further 2 days. The pH was then adjusted to 8 with sodium bicarbonate solution and the ethanol was removed by evaporation. The aqueous residue was washed with ether and the aqueous phase was acidified to pH 1.5 under ether with 2N-hydrochloric acid. The ether extracts were combined and washed with water, dried and evaporated to give an orange oil (8.8 g). The crude mixture of syn and anti-isomer was esterified with a slight excess of diazomethane in ether.

To a solution of the mixed methyl esters (7.7 g) in methanol (100 ml) was added N-sodium hydroxide (28 ml). The mixture was kept at room temperature for 3 hours when thin-layer chromatography of an aliquot showed only traces of remaining anti-ester. After a further 30 minutes 2N-hydrochloric acid (14 ml) was added and the methanol was removed by evaporation. The residue was partitioned between ether and excess sodium bicarbonate in water. The ether layer was separated, washed with water, dried and evaporated to a pale orange oil (5.0 g).

This oil in methanol (100 ml) was treated with 10N-sodium hydroxide solution (4.5 ml) and kept at room temperature for 16 hours. A further portion of 10N-sodium hydroxide solution (4.5 ml) was added and after 24 hours at room temperature the mixture was warmed to 60° for 30 minutes. The methanol was removed by evaporation and the residue divided between ether and sodium bicarbonate solution. The aqueous phase was acidified under ether with 2N-hydrochloric acid. The combined ether extracts were washed with water and dried. Evaporation of the ether gave a pale orange oil (4.8 g) which was crystallised from carbon tetrachloride to give the title compound as pale brown crystals (1.9 g); m.p. 70°-71°; $\lambda_{max.}$ (EtOH) 235, 287.5 nm (ε 11,600 and 17,100); τ (DMSO-d$_6$) values include 4.70 (S, CH$_2$) and 6.18 (S, CH$_3$).

General Method for Converting a 2-Substituted oxyimino-2-arylacetic Acid into its Acid Chloride without Isomerisation A solution of the pure syn-2-substituted oxyimino-2-arylacetic acid (1 equiv.) in methanol (ca. 2-ml/mmole) was treated with sodium methoxide (1 equiv.) in methanol at 0°-25° and the mixture evaporated to give the sodium salt which may be dried by azeotroping with several portions of benzene and/or drying in vacuo over phosphorus pentoxide.

The anhydrous sodium salt (1 equiv.) was suspended in dry benzene (ca. 5 ml/mmole) containing a few drops of dry dimethylformamide and treated with freshly distilled oxalyl chloride (1-2.5 equiv.). The mixture was stirred at room temperature for 0.5-1 hour and then evaporated to remove benzene. The resulting acid chlorides were not characterised but were dissolved in acetone and used immediately to acylate the appropriate cephalosporin nucleus.

The acids described in Preparations 40-51 were converted into their acid chlorides in this way.

PREPARATION 52

Cyclopentyloxamine hydrochloride

A mixture of bromocyclopentane (14.9 g), N-hydroxyphthalimide (16.3 g), triethylamine (15 ml), and dimethylformamide (30 ml) was stirred for 16 hours, then poured into water (500 ml). The oily mixture was extracted with ethyl acetate, and the combined extracts, after washing (water), drying, and removal of solvent gave a white solid. This solid was recrystallised from ethanol to give N-cyclopentyloxyphthalimide (11.37 g, 49%); m.p. 81.2°-82.5°; $\nu_{max.}$ (CHBr$_3$) include 1780, 1720 cm$^{-1}$ (CO—N—CO), 970 cm$^{-1}$

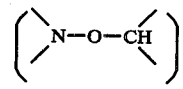

τ values (DMSO-d6) 2.08 (4 Ar-H), 5.12 (cyclopentyl 1-H), 8.18 (4-CH$_2$).

A mixture of N-cyclopentyloxyphthalimide (11 g), 100% hydrazine hydrate (2.6 g), and ethanol (30 ml) was heated under reflux for 5 minutes. Concentrated hydrochloric acid (6 ml) was added to the mixture, which was heated under reflux for a further 5 minutes. Water (20 ml) was added to the mixture, which was cooled to room temperature, and filtered. The filtrate was evaporated to dryness, ethanol (50 ml) was added to the residue, and a small amount of insoluble material was filtered off. The filtrate was evaporated to dryness, and the residue was recrystallised from ethanol/ether to give cyclopentyloxamine hydrochloride (6.28 g, 96%), m.p. 156.9°.

PREPARATION 63 t-Butoxycarbonylmethoxamine t-Butyl chloroacetate (13.0 g, prepared according to *Org. Synth.*, Coll. Vol. 4, 263) was added dropwise to a stirred mixture of N-hydroxyphthalimide (14.2 g), triethylamine (23.0 g), and dimethylformamide (30 ml), and the resulting mixture was stirred for 4 hr. The mixture was poured into water (500 ml), and the precipitated solid was collected, washed with water, and dried. Recrystallisation from ethanol gave N-t-butoxycarbonylmethoxyphthalimide (17.26 g. 72%); m.p. 145.6°; τ values (DMSO-d6) 2.09 (4 Ar—H), 5.28 (CH$_2$), 8.56 (Bu$^t$).

A solution of N-t-butoxycarbonylmethoxyphthalimide (21 g) in methylene chloride (250 ml) was treated with 100% hydrazine hydrate (7.6 ml) in methanol (15 ml), and the mixture was stirred for 1.5 hr. 5N-Ammonia solution was added to dissolve the precipitated solid. The organic layer was separated, and the aqueous layer was further extracted with methylene chloride. The combined extracts were washed with water, dried, and evaporated to give a pale-yellow solid. To this was added ether, the mixture was filtered, and the filtrate evaporated to give t-butoxycarbonylmethoxamine as a pale yellow liquid, (8.88 g, 80%); $v_{max.}$ (Nujol) includes 3330, 3260 cm.$^{-1}$ (NH$_2$), 1742 cm.$^{-1}$ (—COOBu$^t$); τ values (DMSO-d6) are 3.75 (—NH$_2$), 5.96 (CH$_2$) 8.55 (Bu$^t$).

PREPARATION 54

Methyl N-Benzyloxymethylpyrrol-2-ylglyoxylate

Methyl pyrrol-2-ylglyoxylate (306 mg) in diglyme was treated with sodium hydride (63 mg) and stirred at room temperature for 3 hr. Benzyloxymethyl chloride (376 mg) was added and the mixture stirred at room temperature for a further 3 hr. The suspension was filtered and the filtrate evaporated. The residue, in ether, was washed with sodium bicarbonate solution, water and dried. Evaporation gave the crude product as a brown oil (530 mg). Purification by preparative thin-layer chromatography gave the title compound as a colourless oil (250 mg, 46%); τ values (DMSO-d6) include 6.10 (—CH$_3$), 4.20 (>N—CH$_2$—), 5.47 (—OCH$_2$—), 2.70 (—Ph).

PREPARATION 55

N-Benzyloxymethylpyrrol-2-ylglyoxylic acid

Crude methyl-N-benzyloxymethylpyrrol-2-ylglyoxylate (10 g) in methanol (150 ml) was treated with sodium hydroxide solution (N: 40 ml) at room temperature for 1 hr. Thin-layer chromatography showed complete hydrolysis. Hydrochloric acid (2N: 20 ml) was added and the methanol was removed by evaporation. The residue was shaken with sodium bicarbonate solution and ether. The aqueous layer was acidified under ether and the ether extract was washed with water and dried. Evaporation gave the acid as an orange oil (4.5 g, 55%); this material was used directly to make the synmethoxime described in Preparation 49.

PREPARATION 56 syn-Isopropoxyiminophenylacetic acid

A mixture of phenylglyoxylic acid (3.0 g.), isopropoxyamine hydrochloride (2.5 g.), ethanol (100 ml) and water (50 ml) was stirred and adjusted to pH 4.5 to 5 with sodium hydroxide solution (2N). The solution was stirred for 5 hr. maintaining the pH at 4.5–5 with further additions of sodium hydroxide solution. The ethanol was removed by evaporation, the aqueous residue acidified and the product collected by extraction with ethyl acetate. Evaporation of the ethyl acetate gave a brown oil (4.2 g.). that was esterified conventionally with diazomethane to give a mixture of the syn and anti methyl esters of the title compound as an oil (4.04 g.).

The mixture of ester (4.0 g) in methanol (60 ml) was treated with sodium hydroxide solution (2N: 19.0 ml) and kept for 2 hr. at room temperature. The methanol was evaporated and the residue, diluted with water, extracted with ethyl acetate. Evaporation of the dried (MgSO$_4$) ethyl acetate solution gave the crude syn methyl ester (0.82 g.). The ester (0.82 g) in methanol (20 ml) was treated with sodium hydroxide solution (2N: 3.6 ml) and kept at room temperature for 31 hr. Conventional isolation of acidic material gave the crude syn isomer (0.706 g) which was recrystallised from cyclohexane to give the title compound (0.358 g.) m.p. 59.5° $\lambda_{max.}$ (EtOH) 258 nm ε 12,700), τ (DMSO-d$_6$) values include 2.47 (phenyl), 5.53 (O—CH<), 8.71 (CH$_3$).

PREPARATION 57 syn-Propoxyiminothien-2-ylacetic acid

A mixture of thien-2-ylglyoxylic acid (3.12 g), n-propoxyamine hydrochloride (2.8 g.), ethanol (75 ml) and water (75 ml) was adjusted to pH 4.5 to 5 with sodium hydroxide solution (2N) and stirred at room temperature. A clear solution at pH 4.5 to 5 was maintained by further addition of base and ethanol as required. After 4 hr. a further portion of n-propoxyamine hydrochloride (1.4 g) was added and the mixture stirred for a further 3 hr. (keeping the pH at 4.5–5) and then kept overnight. The ethanol was evaporated and the residual solution diluted with water, acidified and extracted with ethyl acetate. Evaporation of the dried (MgSO$_4$) ethyl acetate solution gave a mixture of the syn and anti forms of the title acid as an oil (4.8 g.).

The mixture of acids was esterified conventionally with diazomethane to give a mixture of the syn and anti methyl ester (3.175 g.).

The mixture of esters in methanol (50 ml.) was treated with sodium hydroxide soluton (2N; 14 ml) for 10 min. at room temperature. The methanol was removed, rapidly, by evaporation and the residue, in water, extracted with ethyl acetate. Evaporation of the dried (MgSO$_4$) ethyl acetate solution gave the syn methyl ester (0.416 g). The ester in methanol (10 ml) was treated with sodium hydroxide solution (2N: 1.7 ml) and kept at room temperature for 26 hr. Conventional isolation of acid material gave the title compound as an oil (0.235 g.) τ (DMSO-d$_6$) values include 2.28, 2.7–2.9 (thienyl), 5.90 (O—CH$_2$).

EXAMPLE 1

3-Acetoxymethyl-7β-(2-methoxyimino-2-phenylacetamido)ceph-3-em-4-carboxylic acid (syn-isomer)

To a solution of dicyclohexylcarbodiimide (1.15 g.) and t-butyl 3-acetoxymethyl-7β-aminoceph-3-em-4-carboxylate (1.83 g.) in dry methylene chloride (30 ml) was added a solution of syn 2-methoxyiminophenylacetic acid (1 g.) in dry methylene chloride (15 ml.) and the resulting solution was stirred at room temperature for 1.5 hours. After filtration the filtrate was washed with 2N hydrochloric acid, water, saturated sodium bicarbonate solution, water dried, and evaporated to an orange froth (2.60 g.). Part of this froth (0.21 g.) was triturated with petroleum spirit (b.p. 60°–80°) producing syn-t-butyl 3-acetoxymethyl-7β-(2-methoxyimino-2-phenylacetamido)ceph-3-em-4-carboxylate as a solid (0.15 g.), $\lambda_{max.}$ (EtOH) 258 nm. (ε 17,400), $v_{max.}$ (CHBr$_3$)

1784 cm$^{-1}$ (β-lactam), τ (CDCl$_3$) 2.99 (doublet J 9.0; NH), 2.2–2.7 (multiplet; Ph), 5.97 (singlet; OCH$_3$) 7.93 (singlet; acetate), 8.48 (singlet; t-butyl).

The remainder of the froth (2.4 g.) was shaken with trifluoroacetic acid (10 ml) at room temperature for 10 minutes, and evaporated to an oil. Ether (~80 ml) was added, producing a solution, which on standing precipitated syn-3-acetoxymethyl-3β-(2-methoxyimino-2-phenylacetamido)ceph-3-em-4-carboxylic acid as a white solid (1.58 g., 66%), [α]$_D^{23}$ + 55° (c, 1.02 in dioxan), λ$_{max.}$ (pH 6 phosphate buffer) 258 nm. (ε 19,550). $\nu_{max.}$ (Nujol) 1782 cm.$^{-1}$ (β-lactam), τ (DMSO-d$_6$) 0.21 (doublet, J 8.0 Hz; NH), 2.3–2.6 (multiplet; Ph), 6.08 (singlet; OCH$_3$), 7.98 (singlet, acetate).

EXAMPLE 2

3-Crotonoyloxymethyl-7β-(2-methoxyimino-2-phenylacetamido)ceph-3-em-4-carboxylic acid (syn-isomer)

A suspension of diphenylmethyl 7β-amino-3-crotonyloxymethylceph-3-em-4-carboxylate toluene-p-sulphonate salt (1.0 g) in ethyl acetate (20 ml) was shaken with sodium bicarbonate solution. The ethyl acetate layer was washed with water and brine, dried and concentrated under reduced pressure. The residue was dissolved in methylene chloride (10 ml) and dicylcohexylcarbodiimide (0.324 g) was added. This solution was treated with 2-methoxyimino-2-phenylacetic acid (syn-isomer) (0.281 g.) After 1 hour the mixture was filtered, and concentrated under reduced pressure. The residue was dissolved in ethyl acetate and the solution was washed with 2N-hydrochloric acid, sodium bicarbonate solution, water and brine, dried and concentrated under reduced pressure. The resulting foam (1.0 g) was dissolved in anisole (2 ml) and the solution was treated with trifluoroacetic acid (8 ml). After 5 minutes at 20° the solution was concentrated under reduced pressure. The residue was dissolved in ethyl acetate and this solution was repeatedly extracted with sodium bicarbonate solution. The combined extracts were washed with ethyl acetate and then acidified with 2N-hydrochloric acid and extracted with ethyl acetate. The extract was washed with water and brine, dried, concentrated under reduced pressure and added to stirred petroleum to precipitate the title methoxime (0.467 g; 67%) [α]$_D$ + 37.3° (c 0.9 in DMSO) λ$_{max}$ (pH 6 phosphate buffer) 258 nm (ε 17,800), β$_{max.}$ (Nujol) 1782 (β-lactam), 1710 (CO$_2$H), 1680 and 1540 (CONH) and 1660 cm.$^{-1}$ (unsaturated ester), τ (DMSO-d$_6$, 100 MHz) 0.19 (doublet, J 8 Hz); 3.03 (multiplet; CH=CH—CH$_3$) 6.06 (singlet; NOCH$_3$), 6.28 and 6.50 [2 doublets (branches of quartet), J 18 Hz; C-2 CH$_2$], and 8.12 (double doublets, J 7 and 1.5 Hz; CH=CH—CH$_3$).

EXAMPLES 3–11

General Procedures for the Preparation of 7β-(2-alkoxyimino-2-substituted-acetamido)-3-(substituted)-methylceph-3-em-4-carboxylic acids using Dicyclohexylcarbodiimide (i) Preparation of Intermediate 4-Carboxylic Acid Esters Method A To a solution of a t-butyl or diphenylmethyl ester of 7β-amino-3-(substituted)-methylceph-3-em-4-carboxylic acid (1 equiv.) and dicyclohexylcarbodiimide (1–1.2 equiv.) in dry methylene chloride (cosolvents e.g. dimethylformamide or dioxane have been used) was added, at 0°–20°, a solution of the syn 2-alkoxyiminosubstituted acetic acid (1 equiv.) in dry methylene chloride. After stirring for 45 min-3 hr. at room temperature the mixture was filtered, the filtrate was washed successively with 2N-hydrochloric acid, saturated sodium hydrogen carbonate solution, water and brine. The organic phase was dried and evaporated to give the required ester as an oil or foam.

Method B

As above using the dimethyl ether of diethylene glycol in place of methylene chloride.

Method C

As Method A with purification of the ester by chromatography on silica.

Method D As Method A but with prior regeneration of the 7β-amino ester from its p-toluene-sulphonic acid salt (1 equiv.) by shaking with ethyl acetate and an excess of saturated sodium bicarbonate solution. After washing with water and brine the organic layer was evaporated to dryness and redissolved in methylene chloride. cl (ii) Deprotection of the Intermediate Esters
Method E The t-butyl or diphenylmethyl ester was dissolved in trifluoroacetic acid (5–10 ml./gm. ester) and left at room temperature for (5–10 min.) then evaporated under reduced pressure. The crude product was taken up in ether or ethyl acetate, extracted into aqueous sodium hydrogen carbonate solution and washed with ethyl acetate. The aqueous layer was acidified with 2N-hydrochloric acid and extracted into ethyl acetate. The organic layer was washed, dried and evaporated to give the required syn-7β-(2-alkoxyimino-2-substituted acetamido)-3-(substituted)-methylceph-3-em-4-carboxylic acid.

Method F

The ester was dissolved in anisole (1–5 ml./grm. ester) and treated with trifluoroacetic acid (4–10 ml./grm. ester) at room temperature for 5–10 min. then worked up as described in Method E.

(iii) Preparation of Diphenylmethyl 7β-Amino-3-cyclopropylcarbonyloxymethylceph-3-em-4-carboxylate p-toluene-sulphonic acid salt used as Starting Material in Example 11

(a) Diphenylmethyl 3-cyclopropylcarbonyloxymethyl-7β-(thien-2-yl)-acetamidoceph-3-em-4-carboxylate To a stirred solution of diphenylmethyl 3-hydroxymethyl-7β-(thien-2-yl)acetamidoceph-3-em-4-carboxylate (8 g.) in dry tetrahydrofuran (20 ml.) containing anhydrous pyridine (6.7 ml.) was added a solution of cyclopropane carbonyl chloride (from the acid, 6.7 g. and thionyl chloride at room temperature for 90 mins.) in dry tetrahydrofuran (10 ml.) over a period of 10 mins. at room temperature. After stirring at room temperature for 2 hr. the mixture was evaporated to near dryness and diluted with ethyl acetate (100 ml.). The mixture was washed successively with sodium hydrogen carbonate solution, 2N-hydrochloric acid and water. The organic layer was stirred with charcoal at room temperature for 1 hr., filtered and the filtrate evaporated to a foam. Trituration with petroleum spirit (bp. 60°–80°) gave the title ester (7.8 g., 87%), [α]$_D$ + 28° (c 0.83 in dioxan), λ inf. (EtOH) 235, 255 nm (ε 12,800, 7,700), $\nu_{max.}$ (CHBr$_3$) 1790 (β-lactam), 1728 cm.$^{-1}$ (esters), τ (DMSO-d$_6$) values include 0.8 (doublet NH) 3.02 (CHPh$_2$), 8.4 (multiplet,

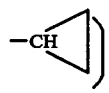

9.0 – 9.2 (CH$_2$ groups in the cyclopropane ring).

EXAMPLE 3

(a) t-Butyl 3-methyl-7β-(2-methoxyimino-2-phenylacetamido)-ceph-3-em-4-carboxylate (syn-isomer) was obtained as a yellow solid m.p. 66° (dec.), λ$_{max.}$ (EtOH) 255 nm (ε 16,350), ν$_{max.}$ (CHBr$_3$) 1785 (β-lactam), 1720 (t-butyl ester), 1690, 1520 cm.$^{-1}$ (CONH); τ (CDCl$_3$) 3.02 (doublet J 8.0 Hz; NH) 2.3–2.7 (multiplet, Ph), 5.96 (singlet; OCH$_3$), 7.89 (singlet, CH$_3$) 8.48, (singlet; t-butyl) by Method A. Deprotection by Method E gave:

(b) 3-Methyl-7β-(2-methoxyimino-2-phenylacetamido)ceph-3-em-4-carboxylic Acid (syn-isomer), as a cream solid (67%), m.p. 145° (dec.), [α]$_D^{17}$ + 100° (c. 1.32 in dioxan) λ$_{max.}$ (pH 6.0 phosphate buffer) 258–259 nm (ε 18,650), ν$_{max}$(Nujol) 1760 (β-lactam), 1702 (CO$_2$H), 1660, 1536 (CONH); τ (DMSO-d$_6$) 0.24 (doublet J 8.0 Hz; NH), 2.3–2.6 (multiplet; Ph), 6.05 (singlet, OCH$_3$), 7.94 (singlet; CH$_3$).

EXAMPLE 4

(a) t-Butyl (3-Acetoxymethyl-7β-(2-benzyloxyimino-2-phenylacetamido)ceph-3-em-4-carboxylate (syn-isomer) m.p. 123°–125°, ν$_{max}$ (EtOH) 259 nm (ε 20,500), ν$_{max}$ (CHBr$_3$) 1796 (ε-lactam), 1732 (acetate and ester), 1694, and 1522 cm$^{-1}$ (CONH); τ (CDCl$_3$) 3.00 (doublet J 9.0 Hz; NH) 2.38, 2.60 (multiplet, Ph), 2.60 (benzyl aromatic protons), 4.74 (singlet; methylene group of benzyl), 7.94 (singlet, acetate), 8.48 (singlet, t-butyl) was obtained by Method A. Deprotection by Method E gave:

(b) 3-Acetoxymethyl-7β-(2-benzyloxyimino-2-phenylacetamido)-ceph-3-em-4-carboxylic acid (syn-isomer) as a white solid (58%), m.p. 167° (dec.) [α]$_D^{26}$ + 50.5° (c, 0.85 in dioxan), λ$_{max.}$ (pH 6.0 phosphate buffer) 259 nm (ε 20,700)., ν$_{max.}$ (Nujol) 1771 (ε-lactam), 1735, 1252 (acetate), 1650 and 1530 cm.$^{-1}$ (CONH), τ (DMSO-d$_6$) 0.14 (doublet J 8.0 Hz; NH), 2.3–2.7 (multiplet; aromatic protons), 4.79 (singlet, CH$_2$ of benzyl group), 7.96 (singlet, acetate).

EXAMPLE 5

(a) Diphenylmethyl 7β-(2-methoxyimino-2-phenylacetamido)3-methylthiomethylceph-3-em-4-carboxylate (syn-isomer) λ$_{max.}$ (EtOH) 259 nm (ε 18,550), ν$_{max.}$ (CHBr$_3$) 1785 (β-lactam), 1722 (benzhydryl ester), 1688 and 1518 cm.$^{-1}$ (CONH); τ (CDCl$_3$) 3.01 (doublet 7 Hz; NH), 2.32, 2.64, 2.65 (aromatic protons) 5.97 (singlet; OCH$_3$), 8.16 (singlet, SCH$_3$) was prepared by Method A. Subsequent deprotection by method E gave:

(b) 3-Methylthiomethyl-7β-(2-methoxyimino-2-phenylacetamido)-ceph-3-em-4-carboxylic acid (syn-isomer) as a precipitated solid., (51%), [α]$_D^{26}$ + 51° (c, 0.98 in dioxan), λ$_{max.}$ (pH 6.0 phosphate buffer) 259 nm, (ε 18,300), ν$_{max.}$ (Nujol) 1781 (β-lactam), 1770 (CO$_2$H), 1670 and 1531 cm.$^{-1}$ (CONH); τ (DMSO-d$_6$) 0.22 doublet J 9 Hz; NH), 6.06 (singlet OCH$_3$), 8.01 (singlet SCH$_3$).

EXAMPLE 6

(a) Diphenylmethyl 3-Benzoyloxymethyl-7β-(2-methoxyimino-2-phenylacetamido)ceph-3-en-4-carboxylate (syn-isomer) was prepared as a crude orange solid (80%) by Method A. Deprotection by Method F gave:

(b) 3-Benzoyloxymethyl-7β-(2-methoxyimino-2-phenylacetamido)-ceph-3-em-4-carboxylic Acid (syn-isomer) as a white powder (48%) [α]$_D$ + 46.5° (c 0.9 in DMSO) λ$_{max.}$ (pH 6 phosphate buffer) 232.5 (ε 22.400) and 258.5 nm (ε21,400) ν$_{max.}$ (Nujol) 1780 (ε-lactam), 1720 and 1265 (benzoate), 1705 (CO$_2$H), 1675 and 1532 cm$^{-1}$ (CONH) τ (DMSO-d$_6$, 100 MHz), 0.16 (doublet, J 8 Hz; NH) 4.06 (double doublet J 5 and 8 Hz; C-7H), 4.70 (doublet; J5 Hz; C-6 H), 6.03 (singlet; NOCH$_3$), and 6.14 and 6.44 [2 doublets (branches of quartet), J 18 Hz; C-2 CH$_2$].

EXAMPLE 7

(a) Diphenylmethyl 3-Isobutyryloxymethyl-7β-(2-methoxy-imino-2-phenylacetamido)ceph-3-em-4-carboxylate (syn-isomer) was prepared by Method A and deprotected without purification by Method Fto give:

(b) 3-Isobutyryloxymethyl-7β-(2-methoxyimino-2-phenylacetamido)ceph-3-em-4-carboxylic acid (synisomer) (73%) [α]$_D$ + 48.5° (c 1.0 in DMSO) λ$_{max.}$ (pH 6 phosphate) 258 nm (ε 18,700), ν$_{max.}$ (Nujol) 1783 (β-lactam), 1725 (carboxylic ester and acid), 1670 and 1530 cm.$^{-1}$ (CONH), τ (DMSO-d$_6$; 100 NHz) 0.19 (doublet, J 8 Hz; NH) 2.2–2.6 (multiplet; aromatic protons), 4.09 (double doublet, J 5 and 8 Hz; C-7H), 4.76 (doublet, J 5 Hz; C-6 H), 4.94 and 5.26 [2 doublets (branches of quartet), J 13 Hz; C-3 CH$_2$], 6.04 (singlet; NOCH$_3$), 6.28 + 6.50 [2 doublets (branches of quartet), J 18 Hz; C-2 CH$_2$], 7.40 (septet, J 7 Hz; C$\underline{H}$ (CH$_3$)$_2$) and 8.80 (doublet, J 7 Hz; CH(C$\underline{H}$$_3$)$_2$).

EXAMPLE 8

(a) t-Butyl 3-Acetoxymethyl-7β-[2-methoxyimino-2-(thien-2-yl)-acetamido]-ceph-3-em-4-carboxylate (syn-isomer) was obtained as a solid (85%), λ$_{max}^{EtOH}$262–263 nm (ε 14,900), λ$_{inf.}$ 280 nm (ε 13,280) ν$_{max.}$ (CHBr$_3$) 3400 (NH); 1780 (β-lactam); 1738, 1120 (CO$_2$R) and 1684, 1514 cm.$^{-1}$ (CONH) τ (CDCl$_3$) 2.5–2.7, 2.95 (thienyl protons); 5.97 (OMe); 7.93 (OAc), and 8.48 (t-butyl) by Method A. Deprotection by Method E gave the free acid:

(b) 3-Acetoxymethyl-7β-[2-methoxyimino-2-(thienyl-2-yl)-acetamido]-ceph-3-em-4-carboxylic acid (synisomer) (56%) [α]$_D^{23}$ + 60° (c, 0.8 in dioxan), λ$_{max.}$ 262 nm (ε 15,700), λ$_{inf.}$ 290 nm. (ε 10,700), ν$_{max.}$ 3275 (NH); 1768 (β-lactam); 1728 (OAc); 1700, 2600 (CO$_2$H); and 1648, 1520 cm.$^{-1}$ (CONH). τ (DMSO-d$_6$) 2.2–2.9 (thienyl); 6.08 (OMe); 0.13 (NH); 4.12, 4.76 (β-lactam); 6.28, 6.52 (J = 18 Hz. CH$_2$ in ring); 4.94, 5.27 (J = 13 Hz. C$\underline{H}$$_2$OAc), and 7.94 (OAc).

EXAMPLE 9

(a) t-Butyl 3-Acetoxymethyl-7β-(2-t-butoxyimino-2-phenylacetamido)-ceph-3-em-4-carboxylate (syn-isomer) was prepared by Method B and purified by chromatography on silica, Method C to give a pale yellow foam (43%) which was crystallised from isopropyl ether to give the ester, m.p. 150°–153°, τ (CDCl$_3$) 2.2–2.75 (multiplet, aromatic protons), 2.83 (doublet, NH), 8.61 (t-butoximine), 8.46 (t-butyl ester). Deprotection by Method F gave (b) 3-Acetoxymethyl-7β-(2-t-butoxyimino-2-phenylacetamido)ceph-3-em-4-carboxylic Acid (synisomer) as a pale yellow foam, $\nu_{max}$. (CHBr$_3$) 1782 (β-lactam) 1685, 1522 cm.$^{-1}$(CONH), τ (DMSO-d$_6$) 2.2–2.75 (multiplet, aromatic protons), 0.4 (doublet, NH), 8.70 (t-butoxime).

EXAMPLE 10

(a) t-Butyl 3-Acetoxymethyl-7β-[2-methoxymethoxyimino-2-(thien-2-yl)acetamido]-ceph-3-em-4-carboxylate (syn-isomer) $\lambda_{max}$. (EtOH) 260 nm (ε 12,940), $\nu_{max}$. (CHBr$_3$) 1778 (β-lactam), 1688 and 1510 cm.$^{-1}$ (CONH), τ (CDCl$_3$) 2.74 (doublet, NH), 4.76 (—OC$\underline{H}$$_2$OCH$_3$), 6.49 (OCH$_2$OC$\underline{H}$$_3$), 7.91 (OCOCH$_3$), 8.44 (Bu$^t$), was prepared by Method A and then treated with trifluoroacetic acid by Method E to give:

(b) 3-Acetoxymethyl-7β-[2-methoxymethoxyimino-2-(thien-2-yl)-acetamido]-ceph-3-em-4-carboxylic Acid (syn-isomer), [α]$_D$ + 51° (c 0.8, DMSO), $\lambda_{max}$. (pH 6 phosphate buffer) 262.5 nm (ε 16,400), $\nu_{max}$.(Nujol) 1778 (β-lactam), 1670, 1530 cm.$^{-1}$ (CONH), τ (DMSO-d$_6$) 0.11 (doublet; NH), 4.89 (OC$\underline{H}$$_2$OCH$_3$), 6.62 (OCH$_2$OC$\underline{H}$$_3$), 7.96 (OCOCH$_3$).

EXAMPLE 11

(a) Diphenylmethyl 3-Cyclopropylcarbonyloxymethyl-7β-(2-ethoxyimino-2-phenylacetamido)ceph-3-em-4-carboxylate (syn-isomer) $\lambda_{max}$. (EtOH) 256.5 nm (ε 15,800) $\nu_{max}$. (CHBr$_3$) 1780 (β-lactam), 1680, 1510 (CONH), 1720 cm.$^{-1}$ (esters), τ (DMSO-d$_6$) values include 0.19 (doublet, NH), 3.01 (CHPh$_2$), 5.76 (C$\underline{H}$$_2$CH$_3$), 8.68 (CH$_3$), 8.35

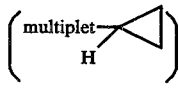
(multiplet $\triangleleft$ H)

9.2 (CH$_2$ groups in cyclopropane ring) was prepared by Method C and then deprotected by Method F to give (b) 3-Cyclopropylcarbonyloxymethyl-7β-(2-ethoxyimino-2-phenylacetamido)ceph-3-em-4-carboxylic Acid (syn-isomer), [α]$_D$ + 75°, (c 0.86 dioxan) $\lambda_{max}$. (pH 6 phosphate buffer) 257 nm (ε 16,000), $\nu_{max}$.(Nujol) 1780 cm.$^{-1}$ (β-lactam) τ (DMSO-d$_6$) values include 0.25 (doublet NH), 5.80 (CH$_2$CH$_3$), 8.73 (CH$_3$).

EXAMPLE 12

3-Acetoxymethyl-7β-(2-methoxyimino-2-phenylacetamido)ceph-3-em-4-carboxylic acid (syn-isomer).

To a cold (0°–5°) solution of 3-acetoxymethyl-7β-aminoceph-3-em-4-carboxylic acid (0.565 g.) in acetone (10 ml) and water (10 ml) containing anhydrous sodium bicarbonate (0.42 g) was added a solution of syn-2-methoxyiminophenylacetyl chloride (0.495 g.) in acetone (5 ml) over a period of 5 minutes. The solution was stirred at room temperature for 30 minutes and then evaporated to remove acetone. The solution was washed with ether (20 ml), and the aqueous phase acidified under ethyl acetate (50 ml) to pH 2 with 2N-hydrochloric acid. The mixture was filtered and the layers separated; the aqueous phase was extracted with ethyl acetate. The organic extracts were combined, dried and evaporated to give a white solid (0.48 g.). This was triturated with ether, producing the title compound (0.45 g. 64%), [α]$_D$$^{17}$ + 56° (1.04 in dioxan), $\lambda_{max}$.(pH 6 phosphate buffer) 259 nm (ε 19,700), $\nu_{max}$.(Nujol) 1778 (ε-lactam), 1740, 1262 (OCOCH$_3$) 1712 (CO$_2$H), 1660, 1543 cm.$^{-1}$(CONH); τ (DNSO-d$_6$) values include 0.2 (Doublet, J 8.0 Hz; NH), 2.3–2.6 (multiplet; Ph), 6.05 (singlet; OCH$_3$), 7.94 (singlet, acetate).

EXAMPLE 13

3-Acetoxymethyl-7β-(2-ethoxyimino-2-phenylacetamido)-ceph-3-em-4-carboxylic acid (syn-isomer)

Oxalyl chloride (0.26 ml.) was added to a suspension of sodium syn-ethoxyiminophenylacetate [prepared from the corresponding acid (300 mg.) and 0.43N sodium methoxide solution (3.62 ml.), and dried over phosphorus pentoxide] in dry benzene (20 ml.) containing 1 drop of dimethylformamide. After stirring for 1 hour, the mixture was evaporated to dryness at room temperature. The residue was dissolved in acetone (15 ml.), and this solution was added dropwise to an ice-cooled, stirred solution of 7β-aminocephalosporanic acid (424 mg.) in water (20 ml.) containing sodium bicarbonate (262 mg.). The mixture was stirred for 2 hr., then the acetone was evaporated and the aqueous solution was acidified to pH 1.5. This mixture was extracted with ethyl acetate, the extracts were combined, washed (water, brine) and dried. Evaporation of the extracts gave the title compound (622 mg., 89%) as a colourless foam, [α]$_D$ + 56° (c. 1.04 dioxan), $\lambda_{max}$.(pH 6 phosphate buffer), 257.5 nm (ε 20,200), $\nu_{max}$. (Nujol) 1772 (β-lactam), 1656 and 1518 cm.$^{-1}$(-CONH), τ values (DMSO-d$_6$) include 0.23 (doublet, J 8 Hz, NH), 2.314 2.6 (multiplet, aromatic protons), 5.75 (quartet, C$\underline{H}$$_2$CH$_3$), 8.68 (triplet, CH$_2$C$\underline{H}$$_3$). 7.96 (OCOCH$_3$).

EXAMPLE 14

3-Acetoxymethyl-7β-(2-t-butoxyiminothien-2-ylacetamido)ceph-3-em-4-carboxylic Acid (syn-isomer)

Methanolic sodium methoxide (0.53 N, 7.5 ml) was added dropwise to a stirred solution of syn-t-butoxyimino-thien-2-ylacetic acid (0.9 g.) in dry methanol (10 ml.) at 0° – 5°. The mixture was evaporated to remove methanol and dried by azeotroping with dry benzene. Oxalyl chloride (0.63 ml., 0.95 g.) was added to a stirred suspension of the sodium salt and dimethylformamide (3 drops) in dry benzene (40 ml.). The mixture was stirred at room temperature for 1 hr. and evaporated to remove benzene. The acid chloride in acetone (10 ml.) was added dropwise to a stirred solution of 7β-aminocephalosporanic acid (1.09 g.) and sodium bicarbonate (0.672 g.) in acetone (20 ml.) and water (20 ml.) at 0° – 5° and the mixture was stirred at room temperature for 2 hr. The resulting solution was evaporated to remove acetone and washed with ethyl acetate. The aqueous solution was acidified, in the presence of ethyl acetate, with 2N hydrochloric acid to pH 1.5 and extracted with ethyl acetate. The combined extracts were washed with water, dried and evaporated to give the title compound (1.15 g., 61%) as a pale yellow foam, [α]$_D$$^{23}$ + 61° (c 1.0 dioxan), $\lambda_{max}$.(pH 6 phosphate buffer) 260 nm (ε 12,500), $\lambda_{max}$. (Nujol) 1780 (β-lactam) 1666 and 1520 cm.$^{-1}$ (CONH) τ values (DMSO-d$_6$) include 0.28 (doublet, J 8 Hz; NH), 2.36 (1H) and 2.84 (2H) (thien-2-yl protons), 7.98 (OAc), 8.68 (Bu$^t$).

EXAMPLE 15

3-Acetoxymethyl-7β-(2-t-butoxyiminobenzo[b]-thien-3'-ylacetamido)ceph-3-em-4-carboxylic Acid (syn-isomer)

syn-t-Butoxyiminobenzo-[b]-thien-3-ylacetic acid (0.976 g.) was treated with sodium methoxide solution (0.445 M: 6.1 ml) at room temperature. Evaporation gave the sodium salt as a white powder (1.05 g.) This was dried over phosphorus pentoxide overnight.

The sodium salt (0.5 g.) suspended in dry benzene (10 ml) containing dimethylformamide (1 drop) was treated at room temperature with oxalyl chloride (0.4 ml) for 1 hr. The solvent was removed by evaporation and the residue in acetone (20 ml) was added dropwise to a solution of 7β-aminocephalosporanic acid (0.49 g.) and sodium bicarbonate (0.378 g.) in water (30 ml) at 0°–5°. The resulting pale yellow suspension was stirred at room temperature for 2½ hr. The acetone was removed by evaporation and the aqueous phase was acidifed to pH 2 under ether. The ether fraction was washed with water and dried. Evaporation gave a cream-coloured foam that was dissolved in methylene chloride and reevaporated to give, after drying, the title compound (0.85 g. 95%). $[\alpha]_D + 61°$ (c 1 dioxan), $\lambda_{max}$. (pH 6 buffer) 230, 297, 304 inf. nm ($\epsilon$ 27,600, 11,500, 10,630), $\tau$ (DMSO-$d_6$) values include 0.29 (doublet, NH), 4.04 (double doublet, 7 proton), 4.73 (doublet, 6-proton), 8.59 (Bu$^t$).

EXAMPLE 16

3-Acetoxymethyl-7β-(2-t-butoxyiminofur-2'-ylacetamido)ceph-3-em-4-carboxylic Acid (syn-isomer)

syn-t-Butoxyiminofur-2-ylacetic acid (2.11 g.) was treated at room temperature with sodium methoxide (0.525 M: 19.1 ml). The methanol was removed by evaporation and the resulting buff powder was dried over phosphorus pentoxide overnight. The sodium salt (933 mg.) in dry benzene (10 ml) containing dimethylformamide (1 drop) was treated with oxalyl chloride (0.8 ml) at room temperature for 1 hr. The solvent was removed by evaporation and the residue in acetone (30 ml) was added dropwise to a solution of 7β-aminocephalosporanic acid (1.09 g) and sodium bicarbonate (672 mg.) in water (50 ml) at 0°–5°. The resulting solution was stirred at room temperature for 1½ hr. The acetone was removed by evaporation and the aqueous phase was adjusted to pH 8 and washed with a little ether. The aqueous layer was acidified to pH 2.0 under ether and the organic layer was washed with water, dried and evaporated to give a pale yellow foam. This was dried over silica and potassium hydroxide pellets to give the title compound as a pale yellow foam (1.6 g. 86%), $[\alpha]_D + 62°$ (c 1 dioxan). $\lambda_{max}$. pH 6 phosphate buffer) 272 nm ($\epsilon$ 18,600), $\nu_{max}$. (CHBr$_3$) 1780 (β-lactam) 1674 and 1510 cm.$^{-1}$(CONH), $\tau$ (DMSO-$d_6$) values include 0.34 (doublet, NH), 2.17 and 3.34 (fur-2-yl, protons) 8.71 (Bu$^t$).

EXAMPLE 17

3-Azidomethyl-7β-(2-benzyloxyimino-phenylacetamido)-ceph-3-em-4-carboxylic Acid (syn-isomer)

syn-Benzyloxyiminophenylacetic acid (1.28 g.) was treated at room temperature with 0.525 molar sodium methoxide solution (9.55 ml). in methanol. Evaporation gave the sodium salt as a white powder.

The sodium salt, suspended in dry benzene (15 ml.) containing dimethylformamide (2 drops) was treated with oxalyl chloride (0.51 ml.) and kept at room temperature for 1 hr. After filtration through a dry sinter the filtrate was evaporated and the residue in dry methylene chloride (20 ml.) added to a solution of 7β-amino-3-azidomethylceph-3-em-4-carboxylic acid (1.27 g.) and triethylamine (2.07 ml.) in dry methylene chloride (50 ml.) at 0° – 5°. The resulting pale orange solution was stirred at room temperature for 1¼ hr. Evaporation gave a brown foam which was dissolved in water, washed with a little ether and acidified to pH 1.8 under ethyl acetate. The ethyl acetate gave the crude product as a yellow foam (1.9 g., 77%). Precipitation from sodium bicarbonate solution (50 ml.) with dilute acid gave the title compound (1.4 g., 56%). $[\alpha]_D + 49.5°$ (c 1 dioxan) $\lambda_{max}$. pH 6 phosphate buffer) 258.5 nm ($\epsilon$ 19,400) $\lambda_{max}$. (CHBr$_3$) 1782 (β-lactam) 1684 and 1512 cm.$^{-1}$(CONH). $\tau$ values (DMSO-$d_6$) include 0.07 (doublet, J 8 Hz; NH), 2.58 (multiplet, aromatic protons), 4.76 (CH$_2$Ph), 4.05 (double doublet, C 7 proton).

EXAMPLE 18

Sodium 3-azidomethyl-7β-(2-methoxyimino-2-phenylacetamido)ceph-3-em-4-carboxylate (syn-isomer).

To a cold (0°–5°) solution of 3-azidomethyl-7β-aminoceph-3-em-4-carboxylic acid (4.6 g.) in acetone (100 ml) and water (100 ml) containing sodium bicarbonate (3.66 g.), was added dropwise over 20 minutes a solution of syn 2-methoxyiminophenylacetyl chloride (4.32 g.) and the resulting yellow solution was stirred at room temperature for 30 minutes. Acetone was removed by evaporation, and the dark green solution was washed with ether. The pH of the aqueous phase under ethyl acetate (100 ml) was reduced to 2 with 2N-hydrochloric acid. The layers were separated, and the aqueous phase was extracted with ethyl acetate. The organic extracts were combined, dried, and evaporated to a pale brown froth (8.2 g.) which was triturated with petroleum spirit (b.p. 60°–80°) and decolourised with charcoal, producing a cream froth (7.67 g.)

This was dissolved in ethyl acetate (30 ml), and a 10% w/v solution of sodium 2-ethyl hexanoate in n-butanol (34.8 ml). was added dropwise to the stirred solution, precipitating the title compound (4.05 g, 51%), $[\alpha]_D^{23} + 63.5°$ (c, 1.0 in water), $\lambda_{max}$. (pH 6.0 phosphate buffer) 258–259 nm. ($\epsilon$ 18,850), $\nu_{max}$. (Nujol) 2102 (N$_3$), 1756 (β-lactam), 1596 (CO$_2^{31}$ ), 1682 and 1528 cm.$^{-1}$ (CONH); $\tau$ (DMSO-$d_6$) values include 0.22 (doublet J 8 Hz; NH), 2.3–2.6 (multiplet, Ph) and 6.04 (singlet, OCH$_3$).

EXAMPLE 19–46

General Procedures for the Preparation of 3-Substituted-methyl-7β-(2-substituted oxyimino-2-arylacetamido)-ceph:3-em-4-carboxylic Acids Method A A solution of the appropriate syn-2-substitutedoxyimino-2-arylacetyl chloride (prepared from 1 equiv. of the corresponding sodium salt with oxalyl chloride) was dissolved in acetone and the solution was added dropwise to a stirred, ice-cold (0°–5°) solution of 7β-aminocephalosporanic acid or 3-azidomethyl-7β-amino-ceph-3-em-4-carboxylic acid (1 equiv.) in water containing sodium bicarbonate (2–2.5 equiv.). The mixture was stirred for 30 min.-2.5 hr. allowing the temperature to rise to room temperature. Acetone was removed by evaporation under reduced pressure, the pH was adjusted to 1.5–2.0 and the product was extracted into ethyl acetate (or occasionally ether). The extracts were washed with water or saturated brine, dried and evaporated to a foam or a solid.

Method B

As in Method A but the product was purified by dissolving in aqueous sodium bicarbonate and re-precipitated by acidification.

Method C

As in Method A but the sodium salt was extracted into ethyl acetate and the extract washed successively with 2N-hydrochloric acid and water, dried and evaporated to a foam.

Method D

A solution of the appropriate acid chloride (1 equiv.) was dissolved in dry methylene chloride (ca. 5 ml/mmole) and the solution was added to a suspension or a solution of 7β-aminocephalosporanic acid or 3-azidomethyl-7β-aminoceph-3-em-4-carboxylic acid (1 equiv.) and triethylamine (3 equivs.) in methylene chloride at 0°–5°. After stirring at room temperature for 1–1.5 hr. the solution was evaporated to dryness, dissolved in water, washed with ethyl acetate and the aqueous layer acidified to pH 1.5 under ethyl acetate. The ethyl acetate extract was washed with water and saturated brine and evaporated to a foam or solid.

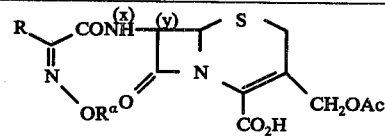

| Ex. No. | R | $R^a$ | Method | $[\alpha]_D$ (dioxan) | pH 6 $\lambda_{max}$ nm | $\epsilon$ | β-lactam $\nu_{max}$ cm.$^{-1}$ (solvent) | τ values for DMSO-$d_a$ at 100 MHz | | | Yield % |
|---|---|---|---|---|---|---|---|---|---|---|---|
| | | | | | | | | x | $R^a$ | y | |
| 19 | Ph | $C(CH_3)_3$ | D | +75° | 256 | 19,100 | 1775 (Nujol) | 0.39 | 8.63 | 4.07 | 70 |
| 20 | Ph | (5-methylthien-2-yl) | A | +44° | 251.5 | 12,900 | 1790 (Nujol) | 0.16 | 4.63 ($CH_2$) 2.50,2.76 2.93 (thien-2-yl) | 4.10 | 71 |
| 21 | (thien-2-yl) | $CH_3$ | A | +60° | 262 | 15,200 | 1768 (Nujol) 1780 ($CHBr_3$) | 0.13 | 6.08 | 4.12 | 76 |
| 22 | " | $C_2H_5$ | A | +88° | 262.5 | 16,600 | 1768 (Nujol) | 0.19 | 5.82 ($CH_2$) 8.75 ($CH_3$) | 4.12 | 77 |
| 23 | " | $n\text{-}C_4H_9$ | A | +55° | 262.5 | 16,500 | 1762 (Nujol) | 0.18 | 5.86, 8.2–8.8 and 9.06 $(CH_2)_3CH_3$ | 4.11 | 87 |
| 24 | " | $CHOC_2H_5$ \| $CH_3$ | A | +64° (DMSO) | 260.5 | 16,300 | 1776 (Nujol) | 0.16 | 8.6 ($CH_3$) 8.84 ($CH_2CH_3$) 4.66 ($CHCH_3$) | 4.10 | 54 |
| 25 | " | $CH_2CH_2Br$ | A | +53° | 262.5 | 15,500 | 1778 (Nujol) | 0.14 | 5.59 ($OCH_2$) 6.30 ($CH_2Br$) | 4.10 | 93 |
| 26 | " | $CH_2Ph$ | D | +58° | 262.5 293 | 16,000 12,000 | 1770 (Nujol) | 0.08 | 4.79 ($CH_2$) 2.58 (Ph) | 4.11 | 60 |
| 27 | " | (5-methylthien-2-ylmethyl) | A | +50° | 242 260 294.5 | 17,700 17,300 12,100 | 1762 (Nujol) | 0.04 | 4.63 ($CH_2$) | 4.09 | 94 |
| 28 | " | (pyrid-2-ylmethyl) | A | +36° | 260 | 18,200 | 1786 (Nujol) | −0.12 | 4.78 ($CH_3$) 1.44,2.16, 2.50 and 2.85 (pyrid-2-yl) | 4.11 | 63 |
| 29 | (5-methylthien-2-yl) | $CH_2Ph$ | A | +52° | 262 | 23,200 | 1768 (Nujol) | 0.14 | 4.77 ($CH_2$) 2.57 (Ph) | 4.08 | 96 |
| 30 | (naphth-2-yl) | $CH_3$ | A | +50° | 260 292 | 13,000 7,600 | 1762 (Nujol) | 0.09 | 5.95 | 4.12 | 79 |
| 31 | " | $C(CH_3)_2$ | C | +35° | 296 | 8,600 | 1780 (Nujol) | 0.26 | 8.59 | 4.09 | 80 |
| 32 | " | $CH_2Ph$ | C | +40° | 290 (infl.) | 8,200 | 1778 (Nujol) | 0.00 | 4.67 ($CH_2$) | 4.10 | 95 |
| 33 | (benzothien-3-yl) | $CH_3$ | A | +51.5° | 226 298.5 | 28,300 10,800 | 1783 ($CHBr_3$) | 0.2 | 5.97 | 4.11 | 77 |
| 34 | " | $CH_2Ph$ | C | +49° | 225 | — | 1760 ($CHBr_3$) | 0.06 | 4.62 ($CH_2$) | 4.13 | 33 |
| 35 | (5-methylfur-2-yl) | $CH_3$ | A | +54° | 273 | 18,100 | 1784 ($CHBr_3$) | 0.16 | 6.07 | 4.13 | 50 |
| 36 | " | $CH_2Ph$ | A | +51° | 275.5 | 19,000 | 1790 ($CHBr_3$) | 0.16 | 4.83 ($CH_2$) 2.64 (Ph) | 4.16 | 85 |
| 37 | (benzothien-2-yl) | $CH_2Ph$ | A | +55° | 231 254 306.5 | — — — | 1778 ($CHBr_3$) | −0.08 | 4.68 ($CH_2$) 2.50 (Ph) | 4.00 | 85 |

-continued

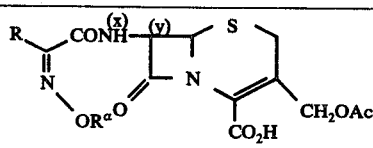

| Ex. No. | R | $R^a$ | Method | $[\alpha]_D$ (dioxan) | pH 6 $\lambda_{max.}$ nm | $\epsilon$ | β-lactam $\nu_{max.}$ cm.$^{-1}$ (solvent) | τ values for DMSO-$d_a$ at 100 MHz | | | Yield % |
|---|---|---|---|---|---|---|---|---|---|---|---|
| | | | | | | | | x | $R^a$ | y | |
| 38 | (furyl-CH₂) | (furyl) | B | +53° | 275 | 18,200 | 1782 (Nujol) | 0.17 | 4.86 (CH₂) 2.32, 3.4– 3.6 furyl protons | 4.18 | 87 |
| 39 | " | C₂H₅ | A | +59.5° | 274 | 19,300 | 1790 (CHBr₃) | 0.21 | 5.79;8.72 | 4.11 | 73 |
| 40 | (benzothienyl) | CH₃ | A | +58 | 230 253.5 305 | 20,800 18,450 20,800 | 1790 (CHBr₃) | −0.04 | 5.97 | 4.00 | 78 |
| 41 | (benzothienyl) | C(CH₃)₂ | A | +44.5 | 230 254 303 | 20,900 15,200 22,200 | 1780 (CHBr₃) | 0.12 | 8.61 | 4.00 | 83 |

TABLE 3

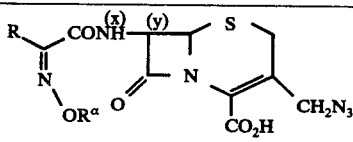

| Ex. No. | R | $R^a$ | Method | $[\alpha]_D$ (dioxan) | pH 6 $\lambda_{max.}$ nm | $\epsilon$ | β-lactam $\nu_{max.}$ cm.$^{-1}$ (solvent) | τ values for DMSo-$d_6$ at 100 MHz | | | Yield % |
|---|---|---|---|---|---|---|---|---|---|---|---|
| | | | | | | | | x | $R^a$ | y | |
| 42 | Ph | C(CH₃)₃ | D | +56° | 258 | 18,300 | 1785 | 0.38 | 8.65 | 4.07 | 30 |
| 43 | (thienyl) | CH₃ | D | +53° | 262 | 14,600 | 1780 (CHBr₃) | 0.09 | 6.10 | 4.10 | 55 |
| 44 | " | C₂H₅ | B | +58° | 263 | 15,600 | 1770 (Nujol) | 0.13 | 5.83 (CH₂) 8.74 (CH₃) | 4.09 | 59 |
| 45 | " | C(CH₃)₃ | B | +62° | 262 288 | 12,200 13,400 | 1780 (Nujol) | 0.25 | 8.68 | 4.07 | 50 |
| 46 | " | CH₂Ph | D | +48° | 263 | 15,800 | — | 0.05 | 4.79 (CH₂) 2.60 (Ph) | 4.12 | 11 |

EXAMPLE 47

7β-(2-Benzyloxyiminothien-2'-ylacetamido)-3-(2-methyl-1,3,4-thiadiazol-5-ylthiomethyl)ceph-3-em-4-carboxylic acid (syn isomer)

Oxalyl chloride (0.45 ml) was added to a stirred suspension of sodium syn-benzyloxyiminothien-2-yl-acetate (0.747 g.) in dry benzene (20 ml.) containing dimethylformamide (1 drop). The mixture was stirred for one hour, then evaporated to dryness. A solution of the residue in ethyl acetate (25 ml.) was added dropwise to a stirred suspension of diphenylmethyl 7β-amino-3-(2-methyl-1,3,4-thiadiazol-5-ylthiomethyl)ceph-3-em-4-carboxylate (1.35 g.) in ethyl acetate (20 ml), containing propylene oxide (1.0 ml.). The solid rapidly dissolved, and the resulting solution was stirred for 16 hr. The solvent was evaporated off, and the residue was redissolved in ethyl acetate (50 ml.) This solution was washed successively with 3% sodium bicarbonate solution, 2N hydrochloric acid, water, and saturated brine, dried, and evaporated to dryness to give the title compound as its diphenylmethyl ester (2.01 g.), as a pale brown foam. τ values include (DMSO-$d_6$) 0.03 (doublet, NH), 4.79 (CH₂Ph) 7.26 (CH₃).

To this crude ester (1.67 g.) was added anisole (0.24 g.), and trifluoroacetic acid (10 ml.). The resulting solution was left at room temperature for 10 min. then the trifluoroacetic acid was removed by evaporation at room temperature. The residue was distributed between ethyl acetate and aqueous sodium bicarbonate solution. The aqueous layer was acidified to pH 1.7 then extracted thrice with ethyl acetate. The combined extracts were washed (water, saturated brine), dried, and evaporated to dryness to give a red foam (1.04 g.). The foam was dissolved in aqueous sodium bicarbonate solution, then reprecipitated by addition of 2N hydrochloric acid. This was repeated to give the title compound (350 mg. 28%) $[\alpha]_D$ −96° (C. 0.97 dioxan), $\lambda_{max.}$ (pH 6 buffer) 274 nm ($\epsilon$ 18,500), $\nu_{max.}$ (Nujol) b 1784 (β-lactam) τ values include (DMSO-$d_6$) 0.07 (doublet, NH), 2.60 (Ph), 4.81 (CH₂Ph) and 7.32 (CH₃).

EXAMPLE 48

(a) t-Butyl 3-acetoxymethyl-7β-(2-methoxyiminopyrid3'-ylacetamido)-ceph-3-em-4-carboxylate (syn-isomer)

A suspension of 2-methoxyiminopyrid-3'-ylacetic acid (1.8 g.) in dichloromethane (50 ml.) was cooled to ca. −10° and treated with phosphorus pentachloride (2.08 g.). The mixture was stirred and maintained at ca. −10° for 1½ hours by which time most of the suspension had dissolved. The cold mixture was treated with t-butyl 7β-amino-3-acetoxymethylceph-3-em-4-carboxylate (8.0 g.) and propylene oxide (2 ml) and stirred for a further 30 minutes. The solution was partitioned between ethyl acetate and saturated sodium bicarbonate solution and extracted with ethyl acetate. The combined organic extracts were washed with water and then extracted with 2N hydrochloric acid. Unchanged amine was removed by the addition of an excess of sodium nitrite to the cooled acidic extract followed by washing with ethyl acetate after ca. 5 minutes at 0°. The resulting aqueous phase was neutralised with saturated sodium bicarbonate solution and extracted with ethyl acetate. The organic extract was washed with water, dried over magnesium sulphate and evaporated to give a mixture of the syn- and anti-isomers of the title compound as a foam (1.33 g.).

Chromatography on silica gel using chloroform-methanol (99:1) gave the anti-isomer (394 mg.) followed by the syn-isomer as a foam (683 mg.). The syn-isomer was dissolved in ethyl acetate and precipitated by adding to petroleum spirit bp. 40°–60°. The amorphous solid was collected, washed with petroleum spirit and dried to yield the title ester (484 mg., 10%), $[\alpha]_D^{20} + 49°$ (C 0.45, DMSO), $\lambda_{max.}$ (EtOH) 255 nm ($\epsilon$ 16,100), $\nu_{max.}$ (CHBr$_3$) 3396 (NH), 1786 (β-lactam), 1735 (OAc), 1724 (Cl$_2$R), 1682 and 1518 cm.$^{-1}$ (CONH), $\tau$ (D$_6$ DMSO) 0.14 (d, J 8 Hz;NH), 1.26, 1.30, 2.03 and 2.48 (multiplets; aromatic protons), 4.10 (q, J 5 and 8 Hz; C-7H), 4.74 (d, J 5 Hz; C-6H), 5.03 and 5.36 (2d, J 13 Hz; C-6H), 5.03 and 5.36 (2d, J 13 Hz; C-3 CH$_2$), 6.03 (s; OCH$_3$), 6.28 and 6.52 (2d, J 18 Hz; C-2 H$_2$), 7.97 (s; OCOCH$_3$), 8.52 (S; C(CH$_3$)$_3$).

(b)

3-Acetoxymethyl-7β-(2-methoxyiminopyrid-3′-ylacetamido)-ceph-3-em-4-carboxylic acid trifluoroacetic acid salt (syn-isomer)

A solution of t-butyl-3-actoxymethyl-7β-(2-methoxyiminopyrid-3-ylacetamido)-ceph-3-em-4-carboxylate syn-isomer (440 mg.), in trifluoroacetic acid (7 ml.) was stood at 20° for 15 minutes. The solvent was removed and the residue evaporated three times from benzene. The resulting gum was dissolved in a small volume of acetone and added slowly to an excess of stirred petroleum spirit (bp 40°–60°). The solid was collected by filtration, washed well with petroleum spirit and dried to afford the title syn acid salt as a solvated pale yellow powder (561 mg.), $[\alpha]_D^{20} + 30°$ (C 0.88, DMSO), $\lambda_{max.}$ (pH 6 buffer) 254 nm ($\epsilon$ 14,300), $\nu_{max.}$ (Nujol) 3250 (NH), 2600 and 1720 (CO$_2$H), 1782 (β-lactam), 1736 (OAc), 1670 (CF$_3$CO$_2^-$), 1670 and 1550 cm.$^{-1}$ (CONH), $\tau$ (D$_6$-DMSO) 0.08 (d, J 8 Hz; NH), 1.16, 1.22, 1.90 and 2.36 (multiplets; aromatic protons), 4.06 (q, J 5 and 8 Hz; C-7H), 4.73 (d, J 5 Hz; C-6H9, 4.93 and 5.26 (2d, J 13 Hz; C-3 CH$_2$), 5.98 (s; OCH$_3$), 6.26 and 6.49 (2d, J 1 Hz, C-2 H$_2$), 7.94 (s; OCOCH$_3$).

EXAMPLE 49

7β-(2-Methoxyimino-2-phenylacetamido)-3-pyridiniummethylceph-3-em-4-carboxylate (syn-isomer).

A solution of 3-acetoxymethyl-7β-(2-methoxyimino-2-phenylacetamido)ceph-3-em-4-carboxylic acid (synisomer) (5 g.) in water (30 ml), acetone (30 ml) and pyridine (2.8 ml.) was heated at 50° for 4 hours. More pyridine (2.8 ml) was added, and the solution (pH ~ 5) was heated at 50° for 16 hours. The dark brown solution was decanted from a gum, evaporated to remove acetone, and washed with methylene chloride. Excess solvent was removed by evaporation, and the solution passed down a column of Dowex 1 ion exchange resin in the acetate cycle and the column eluted with water. The eluate was freeze dried, and the solid was triturated with acetone, producing the title compound as a cream solid (0.84 g), $[\alpha]_D^{23} - 6.4°$ (C, 0.94 in water), $\lambda_{max}$ (pH 6.0 phosphate buffer) 257 nm ($\epsilon$ 19,900) $\nu_{max.}$ (Nujol) b 1770 (β-lactam), 1660, 1540 (CONH) and 1604 cm.$^{-1}$(CO$_2^-$); $\tau$ (D$_2$O) values include 1.03, 1.90 and 1.40 ($\alpha,\beta$ and $\gamma$-protons in the pyridinium ring), 2.2–2.6 (multiplet, Ph), 5.99 (singlet, OCH$_3$), $\tau$ (DMSO-d$_6$) values include 0.27 (doublet, J 8 Hz; NH), 6.10 (singlet, OCH$_3$).

EXAMPLE 50

7β-(2-Methoxyimino-2-phenylacetamido)-3-(4-carbamoylpyridiniummethyl)-ceph-3-em-4-carboxylate (syn-isomer)

3-Acetoxymethyl-7β-(2-methoxyimino-2-phenylacetamido)-ceph-3-em-4-carboxylic acid (syn isomer) (5 g) and isonicotinamide (4.2 g) were mixed in water (150 ml) and acetone (30 ml.) and the suspension heated at 50° for 20 hours. The mixture was cooled, filtered, evaporated to remove acetone, and the aqueous solution was passed down a column (3 × 16 cm.) of Dowex 1 ion exchange resin in the acetate cycle. After washing the column with water the elute was freeze dried, and the resulting solid was stirred with acetone (250 ml.) for 30 minutes, and the suspension filtered, producing the title compound (1.4 g.), $[\alpha]_D^{23} - 50°$ C (c 106 in DMSO), $\lambda_{max.}$ (pH 6 buffer) 260 nm. ($\epsilon$ 20,900), $\nu_{max.}$ Nujol 1770 (β-lactam), 1675 and 1560 (CONH) and 1605 cm.$^{-1}$ (CO$_2^-$), $\tau$ (DMSO-d$_6$) values include 0.33, 1.49 ($\alpha$, and $\beta$ protons in pyridinium ring), 1.19 and 1.74 (—CONH$_2$), 2.4–2.6 (multiplet, pH), 0.26 (J 8 Hz; NH), 6.10 (singlet; OCH$_3$).

EXAMPLE 51

Sodium 3-hydroxymethyl-7β-(2-methoxyimino-2-phenylacetamido)ceph-3-em-4-carboxylate (syn-isomer).

3-Acetoxymetyl-7β-(2-methoxyimino-2-phenylacetamido)ceph-3-em-4-carboxylic acid (synisomer) (2.0 g.) was dissolved in the minimum volume of saturated sodium bicarbonate solution and the solution was diluted with water (160 ml) and warmed to 37°. Defatted wheat-gram (15 g) was added and the mixture was stirred for 3½ hours during which time the pH remained at 7.4. The mixture was then poured into acetone (200 ml) and filtered through kieselguhr. The acetone was evaporated off under reduced pressure at 30° and the aqueous solution was covered with ethyl acetate, taken to pH 2.7 by the addition of concentrated hydrochloric acid. The layers were separated and the aqueous layer was reextracted with ethyl acetate. The combined ethyl acetate extracts were washed with water. More water was added to the ethyl acetate solution and the pH was taken to 7 by careful addition of 2N sodium hydroxide solution. The organic layer was further extracted with water and the combined aqueous solution was washed with ethyl acetate and ether, degassed and lyophilised to give the title methoxime as a brown solid (1.52 g; 82%) [α]$_D$ + 104° (c 1,1 DMSO) λ$_{max.}$ (pH 6 phosphate) 258.5 nm (g 14,100) ν$_{max.}$ (Nujol) 1730 (β-lactam), 1570 (COO−), 1640 and 1520 cm$^{-1}$ (CONH), τ (D$_2$O; 100 MHz) 2.2 to 2.6 (multiplet; aromatic protons), 4.16 (doublet, J 4 Hz; C-7H), 4.79 (doublet, J 4 Hz; C-6H), 5.72 (singlet; C-2 CH$_2$), 5.95 (singlet, NOCH$_3$), 6.32 and 6.59 [2 doublets (branches of quartet), J 18 Hz; C-3 CH$_2$].

EXAMPLE 52

3-Hydroxymethyl-7β-(2-benzyloxyiminothien-2'-ylacetamido)-ceph-3-em-4-carboxylic Acid (syn isomer)

To a suspension of 3-cetoxymethyl-7β-(2-benzyloxyiminothien-2'-ylacetamido)ceph-3-em-4-carboxylic acid (1.0 g.) in water (50 ml.) was added sufficient saturated sodium bicarbonate solution to dissolve the solid, and bring the solution to pH 7.0. Defatted wheat germ (8.0 g.) was added to the solution, and the mixture was stirred for 21 hr., keeping the pH at 6.8 to 7.0 by adding acetic acid. After 5 hr., the pH did not alter, and TLC (CHCl$_3$:MeOH:AcOH; 18:2:1) on an acidified aliquot showed reaction to be almost complete.

The mixture was filtered, and the pH of the filtrate was adjusted to pH 4.5. Filtration through kieselguhr gave a yellow solution, whose pH was adjusted to 2.5 under ethyl acetate. The aqueous mixture was extracted with ethyl acetate, and the combined extracts were washed (water, brine), dried, and evaporated to dryness to give a brown solid. Trituration of this solid with methylene chloride gave a colourless solid (480 mg.), whose n.m.r. spectrum was consistent with that expected of the hydroxymethyl compound.

A portion of the solid (366 mg.) dissolved in 50% aqueous ethanol (10 ml.) was carefully neutralised with 0.1N sodium hydroxide solution (3.02 ml., required). The ethanol was evaporated, and the aqueous mixture was extracted thrice with ether. Evaporation of the aqueous solution gave sodium 3-hydroxymethyl-7β-(2-benzyloxyiminothien-2'-ylacetamido)ceph-3-em-4-carboxylate dihydrate (132 mg.), [α]$_D$ + 88° (c, 0.89, DMSO) λ$_{max.}$ (pH 6 phosphate buffer) 262 nm (ε 16,100) ν$_{max.}$ (Nujol) 1744 (β-lactam), 1650 and 1522 (CONH), 1580 (CO$_2^-$) cm.$^{-1}$, τ (DMSO-d$_6$) values include 0.13 (doublet, NH), 2.54 (Ph) 4.76 (CH$_2$Ph), 4.26 (quartet, 7-proton).

EXAMPLE 53

3-(2-Chloroethylcarbamoyloxymethyl)-7β-(2-methoxyiminophenylacetamido)ceph-3-em-4-carboxylic acid (syn-isomer)

A solution of 3-hydroxymethyl-7β-(2-methoxyiminophenylacetamido)ceph-3-em-4-carboxylic acid (synisomer) (0.35 g.), 2-chloroethylisocyanate (0.097 g.) and triethylamine (1.79 g.) in dimethylformamide (10 ml.) was stirred at room temperature for 2 hours. The reaction mixture was poured into saturated sodium bicarbonate solution, and the aqueous phase washed with ethyl acetate, acidified and extracted with ethyl acetate. The combined extracts were dried, concentrated to ca. 5 ml. and dropped dropwise with stirring to petroleum spirit (250 ml.). The resulting solid was filtered and dried to give the title acid (0.157 g., 35%) λ$_{max}$ (pH 6 buffer) 258 nm (ε 6,800), λ$_{max}$ (Nujol) 3250 (NH), 2600 and 1715 (CO$_2$H), 1700 and 1530 (NHCO$_2$R), 1660 and 1540 cm.$^{-1}$ (CONH), τ (DMSO-d$_6$) values include 0.22 (doublet J 9 Hz; 7β-NH), 2.3 to 2.6 (multiplet; aromatic protons), 6.05 (singlet; OCH$_3$), 6.40 (multiplet; C-2 CH$_2$ and —CH$_2$Cl), 6.65 (multiplet; —NHCH$_2$).

EXAMPLE 54 (a)

t-Butyl-3-acetoxymethyl-7β-pyrid-4-ylacetamido) ceph-3-em-4-carboxylate

A suspension of pyrid-4-ylacetyl chloride hydrochloride (6.0 g.) in ethyl acetate (50 ml) containing propylene oxide (12 ml.) was stirred, cooled in ice and treated dropwise with a solution of t-butyl 3-acetoxymethyl-7β-aminoceph-3-em-4-carboxylate (5.0 g.) in ethyl acetate (50 ml.). The mixture was stirred at 20° for 20 hours and then washed with saturated sodium bicarbonate solution and extracted with 2N hydrochloric acid. Thd aqueous extract was washed with ethyl acetate, neutralized with saturated sodium bicarbonate solution and extracted with ethyl acetate. The extract was washed with water, dried over magnesium sulphate and evaporated to small bulk whereupon crystallisation began. The crystalline solid was washed well with petroleum spirit (bp. 40°–60°) and dried to give the title ester as a buff coloured powder (5.4 g., 80% based on amine). A portion (250 mg.) was recrystallised from ethyl acetate as white needles (170 mg.), [α]$_D$ +94° (c 0.9, DMSO) λ$_{max.}$ (EtOH) 256.5 nm (ε 9,900), ν$_{max.}$ (CHBr$_3$) 3412 (NH), 1784 (β-lactam), 1736 (OAc), 1722 (CO$_2$r), 1690 and 1512 cm.$^{-1}$ (CONH), τ (D$_6$-DMSO) 0.81 (d, J 8 Hz; NH), 1.47 and 2.68 (2d, J 5 Hz; aromatic protons); 4.27 (q, J 8 and 5 Hz; C-7H), 4.85 (d, J 5 Hz; C-6 H), 5.01 and 5.36 (2d, J 13 Hz; C-3CH$_2$), 6.38 (s; CH$_2$CONH), 6.39 (s; C-2H$_2$), 7.96 (s; OCOCH$_3$), and 8.50 (s; C(CH$_3$)$_3$). (b) t-Butyl 3-acetoxymethyl-7β-(2-hydroxyiminopyrid-4'-ylacetamido)-ceph-3-em-4-carboxylate A solution of t-butyl 3-acetoxymethyl-7β-(pyrid-4-ylacetamido)ceph-3-em-4-carboxylate (3.0 g.) in acetic acid (30 ml.) was stirred, cooled briefly in ice and treated dropwise over 3–4 minutes with a solution of sodium nitrite (1.38 g.), in water (10 ml.). The mixture was stirred at 20° for 30 minutes and was then diluted with water and extracted with ethyl acetate. The organic extract was washed with saturated sodium bicarbonate solution and water and then dried over magnesium sulphate. Evaporation almost to dryness gave a residue which was dissolved in the minimum volume of acetone and added dropwise to stirred petroleum spirit (bp. 40°–60°). The resulting solid was collected, washed with petroleum spirit and dried to yield the title oxime as a white powder (2.9 g., 91%) which was shown (NMR) to be a syn-/anti-mixture (30:70).

The oxime mixture (2.5 g) was chromatographed on silica gel and eluted with methanol-chloroform (1:49) to give the title compound (anti-isomer).

Further elution with methanol-chloroform (1:49) gave material which was dissolved in acetone and added to stirred petroleum bp. 40°–60°) to afford t-butyl 3-acetoxymethyl-7β-(2-hydroxyiminopyrid-4'-ylacetamido)-ceph-3-em-4-carboxylate (syn-isomer, 0.81 g/., 32% from mixture), [α]$_D$ + 57° (c 1.11, DMSO), λ$_{max.}$ (EtOH) 253.5 nm (ε 17,600), ν$_{max. (Nujol)}$ 3220 (NH), 1784 (β-lactam), 1744 (OAC), 1710 (CO$_2$R) 1640 and 1526 cm$^{-1}$ (CONH), τ (D$_6$-DMSO) −2.26 (s; NOH), 0.27 (d, J 8 Hz; NH), 1.33 and 2.47 (2d, aromatic protons), 4.04 (q, J 5 nd 8 Hz; C-7H), 4.71 (D, J 5 Hz; C-6H), 4.98 and 5.33 (2d, J 13 Hz; C-3 CH$_2$), 6.20 and 6.53 (2d, J 18 Hz; C-2 H$_2$) 7.94 (s, OCOCH$_3$), 8.49 (s, C(CH$_3$)$_3$).

(c) t-Butyl
3-acetoxymethyl-7β-(2-methoxyiminopyrid-4'-ylacetamido)-ceph-3-em-4-carboxylate (syn-isomer)

A solution of t-butyl 3-acetoxymehyl-7β-(2-hydroxyiminopyrid-4'-ylacetamido)-ceph-3-em-4-carboxylate (syn-isomer) (50 mg.), in tetrahydrofuran (10 ml.) was cooled to 0° and treated with an excess of ethereal diazomethane. The mixture was stirred at ca. 5° for 45 minutes and then washed with water. The organic extract was dried and evaporated to yield the title ester as a yellow foam (48 mg., 93%), $[\alpha]_D$ +55.5° (c 0.88, DMSO), $\lambda_{max}$ (EtOH) 257.5 nm ($\epsilon$ 16,580), $\nu_{max}$ (CHBr$_3$) 3390 (NH) 1784 (β-lactam), 1736 (OAc), 1726 (CO$_2$R), 1684 and 1516 1 c.$^{-1}$ (CONH), τ (d$_6$-DMSO) 0.20 (d, J 8 Hz; NH), 1.33 and 2.48 (multiplets; aromatic protons), 4.09 (q, J 5 and 8 Hz; C-7H), 4.74 (, J 5 Hz; C-6H), 5.01 and 5.35 (2d, J 13 Hz; C-3CH$_2$), 5.99 (s, NOCH$_3$), 6.38 (broad singlet; C-2H$_2$), 7.96 (s; OCOCH$_3$), 8.52 (s; C(CH$_3$)$_3$).

(d)
3-Acetoxymethyl-7β-(2-methoxyiminopyrid-4'-ylacetamido)-ceph-3-em-4-carboxylic acid trifluoroacetic acid salt (syn-isomer)

A solution of t-butyl-3-acetoxymethyl-7β-(2-methoxyiminopyrid-4'-ylacetamido)-ceph-3-em-4-carboxylate (syn-isomer) (0.35 g.) in trifluoroacetic acid (10 ml) was stood at 20° for 15 minutes. The solution was diluted with benzene and evaporated to dryness to give a gun which was triturated with ether to afford the title acid salt as a solid (0.26 g.m, 67%), $[\alpha]_D$ + 42° (c 0.45, DMSO), $\lambda_{max}$ (pH 6 buffer) 255 nm ($\epsilon$ 19,000), $\nu_{max}$ (Nujol) 3250 (NH), 2600 and 1720 (CO$_2$H), 1778 (β-lactam), 1734 (OAc), 1666 (CF$_3$CO$_2^-$), 1670 and 1520 cm.$^{-1}$(CONH), τ (DMSO-d$_6$) 0.10 (d, J 8 Hz; NH), 1.23 and 2.36 (multiplets; aromatic protons), 4.11 8q, J 5 and 8 Hz; C-7H), 4.76 (D, J 5 Hz; C-6H), 4.98 and 5.29 (2d, J 13 Hz; C-3CH$_2$), 5.97 (s; NOCH$_3$), 6.29 and 6.52 (2, J 18 Hz; C-2H$_2$), 7.98 (s; OCOCH$_3$).

EXAMPLE 55

3-Acetoxymethyl-7β-[2-aminoethoxyimino(thien-2-yl)acetamido]ceph-3-em-4-carboxylic acid, trifluoroacetate salt (syn isomer)

A solution of syn-(2-t-butoxycarboxamido)-ethoxyiminothien-2-ylacetyl chloride (from the acid 314 mg) dissolved in acetone (10 ml.), was added dropwise to an ice-cooled, stirred solution of 7β-aminocephalosporanic acid (272 mg.) in water (20 ml.) containing sodium bicarbonate (168 mg.). The solution was stirred for two hours, then the acetone was evaporated off. The aqueous mixture was acidifed to pH 2.0 under ethyl acetate, and extracted with ethyl acetate. The combined extracts were washed (water, brine), dried and evaporated to dryness to give 3-acetoxymethyl-7β-[2-t-butoxy-carboxamido ethoxyimino(thien-2-yl)acetamido]ceph-3-em-4-carboxylic acid (540 mg., 95%), τ (DMSO-d$_6$) values include 0.27 (d, NH), 7.96(s, OCOCH$_3$), 8.62 (s, C(CH$_3$)$_3$).

This crude acid (500 mg.), was dissolved in trifluoroacetic acid (5 ml.), and the solution was stood at room temperature for 5 min. and then was evaporated to dryness at room temperature. Dry benzene (25 ml.) was added to the residue, and the mixture wa reevaporated to dryness. The oily residue was triturated with ether to give the title compound (346 mg., 64%) as a colourless solid $[\alpha]_D$ + 39° (c 0/.97; dioxan), $\lambda_{max}$ (pH 6 phosphate buffer) 283 nm ($\epsilon$ 16,500), $\lambda_{max}$ (Nujol) 1780 cm.$^{-1}$, τ (DMSO-d$_6$) values include 0.31 (doublet, J 8 Hz; NH), 1.98 (MH$_3$) 4.08 (C-7 proton), 5.66 (—OCH$_2$), 6.8 (—CH$_2$N<O, 7.96 (OCOCH$_3$).

EXAMPLE 56

7β-[2-t-butoxyimino-2-(benzo-[b]-thien-3-yl)acetamido]-3-(5-methyl-1,3,4-thiadiazol-2-yl)thiomethylceph-3-em-4-carboxylic acid (syn-isomer)

A solution of 2-(t-butoxyimino)-2-(benzo-[b]-thien-3-yl)-acetic acid (1.11 g) in methylene chloride (5 ml.) and dimethylformamide (1 ml) was added to a solution of diphenylmethyl 7β-amino-3-(5-methyl-1,3,4-thiadiazol-2-yl)thiomethylceph-3-em-4-carboxylate (204 g) in methylene chloride (20 ml.). A solution of dicyclohexylcarbodiimide (0.823 g) in methylene chloride (5 ml) was added to the above stirred solution at 20°. The mixture was kept at 5° for 16 hours and was then filtered. The filtrate was washed with 2N hydrochloric acid, dilute sodium bicarbonate solution, water and brine, dried (MGSO$_4$), and concentrated under reduced pressure to give the crude diphenylmethyl ester of the title compound as an orange foam (3.37 g.). The foam was dissolved in anisole (6 ml) and the solution was treated with trifluoroacetic acid (25 ml.). After 5 minutes at 20° the solution was concentrated under reduced pressure. The residue was dissolved in ethyl acetate and the resulting solution was again concentrated. The residue was then partitioned between ethyl acetate and dilute sodium bicarbonate solution. The ethyl acetate layer was thoroughly extracted with dilute sodium bicarbonate solution and the combined extracts were washed with ethyl acetate and then were covered with ethyl acetate and taken to pH 2 with concentrated hydrochloric acid. The layers were separated and the aqueous layer was extracted with ethyl acetate. The combined ethyl acetate extracts were washed with water and brine, dried and concentrated under reduced pressure to a low volume. The solution was then added dropwise to stirred petroleum (bp. 40°–60°, 400 ml) and the precipitate was collected and washed with petroleum to give the title acid as a buff solid (1.0 g, 41%), $[\alpha]_D$ −87° (c 1 in DMSO) $\lambda_{max}$ (pH 6 phosphate buffer) 277.5 nm ($\epsilon$ 16,850) $\nu_{max}$ (Nujol) include 1786 (β-lactam), 1672 and 1520 cm.$^{-1}$ (CONH) τ values (DMSO-d$_6$) include 0.27 (d, J 8 Hz; NH), 1.38 (m; H-4benzo-[b]-thienyl) 1.86 (m; benzo-[b]thienyl H-7), 2.15 (s; benzo[b]thienyl H-2) 2.44 (m; benzo[b]-thienyl H-5 and H6) 4.05 (dd, J 8 and 5 Hz; H-7), 4.72 (dm J 5 Hz; H-6) 5.40 + 5.74 (2ds, J 13 Hz; C-3 CH$_2$), 6.13 + 6.37 (2ds, J 18 Hz; C-2 CH$_2$), 7.29 (s; CH$_3$) and 8.57 (s; C(CH$_3$)$_3$).

EXAMPLE 57

7β-[2-Ethoxyimino-2-phenylacetamido]-3-(5-methyl-1,3,4-thiadiazol-2-yl)thiomethylceph-3-em-4-carboxylic acid (syn-isomer), was prepared essentially as described in Example 56 (61% yield) $[\alpha]_D$ −86° (c 1.1 in DMSO) $\lambda_{max}$ (pH 6 phosphate) 262.5 nm ($\epsilon$ 22,350) $\nu_{max}$ (Nujol) include 1780 (β-lactam) and 1664 and 1520 cm.$^{-1}$ (CONH), τ values (DMSO-d$_6$) 0.21 (d, J 8 Hz; NH), 2.46 (m; aromatic protons) 4.06 (dd, J 8 and 5 Hz; H-7), 4.73 (d, J 5 Hz; H-6), 5.40 + 5.72 (2ds, J 14 Hz; C-3CH$_2$), 5.74 (q, J 7 Hz; CH$_3$CH$_2$O) 6.11 + 6.39 (2 ds, J 18 Hz; C-2CH$_2$), 7.27 (s; CH$_3$ in thiadiazole) 8.68 (t, J 7 Hz; CH$_3$CH$_2$O).

EXAMPLE 58

7β-[2-t-Butoxyimino-2-(thien-2-yl)acetamido]-3-(5-methyl-1,3,4-thiadiazol-2-yl)thiomethylceph-3-em-4-carboxylic acid (syn-isomer)

was prepared as in Example 56 to give the acid (58% yield) $[\alpha]_D -76°$ (c 1, DMSO) $\lambda_{max.}$(pH 6 phosphate) 271 nm (ε 14,400) $\nu_{max.}$ (Nujol) include 1780 (β-lactam) and 1670 and 1530 cm.$^{-1}$ (CONH), τ values (DMSO-$d_6$) include 0.26 (d, J 8 Hz; NH), 2.32 + 2.80 (ms; thienyl protons), 4.08 (dd, J 8 and 5 Hz; H-7), 4.73 (d, J 5 Hz; H-6) 5.38 + 5.73 (2 ds, J 13 Hz; C-3 $CH_2$), 6.10 + 6.36 (2 ds, J 18 Hz; C-2$CH_2$), 7.27 (s; $CH_3$) and 8.64 (s, $C(CH_3)_3$).

EXAMPLE 59

(a)

t-Butyl-3-acetoxymethyl-7β-(2-ethoxyiminopyrid-4-yl-acetamido)-ceph-3-em-4-carboxylate (syn-isomer)

t-Butyl-3-acetoxymethyl-7β-(2-ethoxyiminopyrid-4-yl-acetamido)-ceph-3-em-4-carboxylate (0.75 g) was deprotected with trifluoroacetic acid (10 ml) in the usual way to afford the title salt as a powder (0.61 g, 73%), $[\alpha]_D + 30°$ (c 0.4, DMSO), $\nu_{max.}$ (pH6 buffer) 257 nm (ε12,800), ε $_{max.}$ (Nujol) 3300 (NH), 2600 and 1720 ($CO_2H$), 1782 (β-lactam), 1740 (OAc), 1680 ($CF_3CO_2^-$), 1670 and 1552 cm.$^{-1}$ (CONH), τ ($d_6$-DMSO) values include 0.06 (d, J 8Hz; NH), 1.20 and 2.28 (multiplets; aromatic protons), 5.65 (q, J 7Hz; $OCH_2CH_3$), 7.92 (s; $OCOCH_3$) and 8.64 (t. J 7Hz; $OCH_2CH_3$).

EXAMPLES 60–65

The general procedures for the preparation of 3-substituted methyl-7β-(2-substituted oxyimino-2-arylacetamido)ceph-3-em-4-carboxylic acids described in Examples 19–46 were employed to prepare the compounds listed in tabular form below. (the Table may be regarded as a continuation of Table 2).

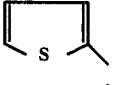

| Ex. No. | R | $R^a$ | Method | $[\alpha]_D$ (dioxan) | pH 6 $\lambda_{max.}$ nm | ε | β-lactam $\nu_{max.}$ cm.$^{-1}$ (solvent) | τ values for DMSO-$d_6$ 100 MHz | | | Yield % |
|---|---|---|---|---|---|---|---|---|---|---|---|
| | | | | | | | | x | $R^a$ | y | |
| 60 | Ph | n-$C_4H_9$ | A | +48° (dioxan) | 257.5 | 19,900 | 1782 (Nujol) | 0.25 | 5.84, 8.2 – 8.8, 9.08 | 4.09 | 92 |
| 61 | Ph | n-$C_3H_7$ | A | +49° dioxan) | 258 | 18,900 | 1778 (Nujol) | 0.26 | 5.89, 8.32, 9.07 | 4.12 | 82 |
| 62 | Ph | —$CH(CH_3)_2$ | A | +50° (dioxan) | 258 | 18,400 | 1780 (Nujol) | 0.31 | 5.56, 8.72 | 4.08 | 73 |
| 63 | 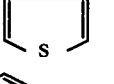 | n-$C_3H_7$ | A | +56° (dioxan) | 262.5 289 inf. | 16,000 11,200 | 1778 (Nujol) | 0.17 | 5.90, 8.32, 9.06 | 4.09 | 82 |
| 64 | (thienyl) | $C_2H_5$ | A | +53° (dioxan) | 261.5 | 20,300 | 1786 (Nujol) | 0.28 | 5.81, 8.75 | 4.1 | 95 |
| 65 | (benzofuryl) | $C_2H_5$ | A | +55.5° (dioxan) | 237 273 inf 303.5 | 12,900 15,500 23,600 | 1785 ($CHBr_3$) | 0.03 | 5.71, 8.68 | 4.09 | 77 |

A solution of t-butyl-3-acetoxymethyl-7β-(2-hydroxyiminopyrid-4-ylacetamido)-ceph-3-em-4-carboxylate (syn-isomer) (1.15 g) in tetrahydrofuran (20 ml) was treated with an excess of diazoethane at 20° for 40 minutes. The mixture was diluted with ether, washed with water and extracted with 2N-hydrochloric acid. The aqueous extract was neutralized with saturated sodium bicarbonate solution and extracted with ethyl acetate. Evaporation of the dried organic extract offered the title ester as a foam (0.84 g, 69%), $[\alpha]_D + 47°$ (c 0.84, DMSO), $\lambda_{max.}$ (EtOH) 259 nm (ε 15,450), $\nu_{max.}$ (Nujol) 3300 (NH), 1788 (β-lactam), 1740 (OAc), 1724 ($CO_2R$), 1678 and 1540 cm.$^{-1}$ (CONH), τ ($d_6$-DMSO) values include 0.12 (d, J 8Hz; NH), 1.26 and 2.42 (multiplets; aromatic protons), 5.69 (q, J 7Hz, $OCH_2CH_3$), 7.93 (s; $OCOCH_3$), 8.50 (s; $(CH_3)_3$) and 8.69 (t, J 7Hz; $OCH_2CH_3$).

(b) 3-Acetoxymethyl-7β-(2-ethoxyiminopyrid-4-ylacetamido)ceph-3-em-4-carboxylic acid trifluoroacetic acid salt (syn-isomer)

EXAMPLE 66

Sodium 3-Acetoxymethyl-7β-(2-phenoxyimino-2-phenylacetamido)-ceph-3-4-carboxylate (syn isomer)

A solution of syn-2-pheoxyimino-2-phenylacetic acid (8.6 g) in dry methanol (30 ml) was neutralised with 1.105N sodium methoxide solution in methanol (32.3 ml). The methanol was evaporated, and the residual sodium salt (dried 48 hr. in vacuo over phosphorus pentoxide) was suspended in dry benzene (75 ml) containing one drop of N,N-dimethylformamide. This suspension was treated with oxyalyl chloride (4.5 ml), the mixture was stirred for 1 hour, and then the solvent and excess reagent was evaporated. A solution of the residual acid chloride in acetone (250 ml) was added over 30 min. to a stirred ice-cooled solution of 7β-aminocephalosporanic acid (9.71 g) in water (500 ml) and acetone (250 ml), containing sodium bicarbonate (6.5 g). When addition was complete, the mixture was stirred for a further 2 hours, then the acetone was evaporated under reduced pressure. The aqueous mixture was covered with ether (500 ml) and acidified to pH 1.8; the acidic layer was further extracted with ether. The combined ether extracts were washed (water, saturated brine), dried and evaporated in dryness to give syn-3-acetoxymethyl-7β-(2-phenoxyimino-2-phenylacetamido)-ceph-3-em-4-carboxylic acid as a pale yellow foam (15.06 g).

To a stirred solution of the above acid (14.5 g) in acetone (150 ml) was added (15 min) a solution of sodium-2-ethylhexanoate (5.5 g) in acetone (50 ml). The precipitated solid was collected, washed with acetone and dried in vacuo to give the title compound (12.92 g); $[\alpha]_D^{22}$ + 111° (C 1.13 DMSO); $\lambda_{max.}$ (pH 6 buffer) 260 nm ($\epsilon$ 19,400), $\lambda$ infl. 285 nm ($\epsilon$ 12,000); $\nu_{max.}$ (Nujol) 3270 (NH), 1752 cm.$^{-1}$ (β-lactam); τ values (DMSO-d$_6$) include −0.05 (d) (NH), 4.16 (dd) (7-h), 4.82 (d) (6H), 7.97 (s) (—O.COCH$_3$).

EXAMPLES 67–76

General Procedures for the Preparation of 3-Acetoxymethyl-7β-(2-substituted oxyimino-2-arylacetamido)-ceph-3-em-4-carboxylic Acids Method A A solution of the appropriate syn-2-substituted oxyimino-2-arylacetyl chloride (prepared from 1 equiv. of the corresponding sodium salt with oxalyl chloride) was dissolved in acetone and the solution was added dropwise to a stirred, cold (0°–5°) solution of 7β-aminocephalosporanic acid (1 equiv.) in water containing sodium bicarbonate (2–2.5 equiv.). The mixture was stirred for 0.5–2.5 hr. allowing the temperature to rise to room temperature. Acetone was removed by evaporation under reduced pressure, ethyl acetate was added, the pH was adjusted to 1.5–2.0 and the product was extracted into ethyl acetate. The extracts were washed with water and saturated brine, dried and evaporated to a foam or solid.

Method B

As in Method A but the product was extracted into ether.

Cephalosporin derivatives so prepared are listed in Table 5.

TABLE 5

| Ex. No. | R | R$^a$ | Method | $[\alpha]_D$ (dioxan) | pH 6 $\lambda_{max}$ nm | $\epsilon$ | β-lactam $\nu_{max}$ cm$^{-1}$ (solvent) | τ values for DMSO-d$_6$ at 100 MHz | | | Yield % |
|---|---|---|---|---|---|---|---|---|---|---|---|
| | | | | | | | | x | R$^a$ | y | |
| 67 |  | Ph | A | + 72° | 270.5<br>296 | 14,750<br>13,300 | 1780<br>(Nujol) | −0.14 | 2.4–2.8 | 4.04 | 96 |
| 68 |  | Ph | A | + 68° | 263.5<br>305 | 16,200<br>10,700 | 1778<br>(Nujol) | −0.14 | 2.4–2.8 | 4.01 | 96 |
| 69 |  |  | A | + 69° | 275 | 16,800 | 1782<br>(Nujol) | 0.33 | 5.28;8.0–8.6 | 4.16 | 98 |
| 70 | 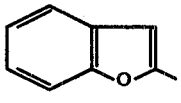 | " | A | + 59° | 262.5<br>294 | 15,700<br>12,300 | 1782<br>(Nujol) | 0.26 | 5.25;8.0–8.6 | 4.10 | 95 |
| 71 |  | —C(CH$_3$)$_3$ | B | + 52.5° | 235.5<br>273<br>301.5 | 13,100<br>17,000<br>24,300 | 1780<br>(CHBr$_3$) | 0.20 | 8.62 | 4.04 | 93 |
| 72 | Ph | 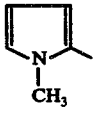 | B | + 96°<br>(Sodium salt in DMSO) | 260 | 19,800 | 1759<br>(Nujol)<br>(Sodium salt) | 0.30 | 5.20;8.0–8.6 | 4.09 | 92 |
| 73 |  | CH$_3$ | B | + 46° | 267<br>293 | 13,000<br>12,300 | 1790<br>(CHBr$_3$) | 0.40 | 6.14 | 4.18 | 75 |
| 74 | " | C(CH$_3$)$_3$ | B | + 56.5° | 270 | 15,300 | 1790<br>(CHBr$_3$) | 0.56 | 8.69 | 4.15 | 79 |

TABLE 5-continued $$R-\underset{\underset{OR^a}{\overset{\|}{N}}}{\overset{(x)}{C}}ONH\underset{(y)}{\overset{S}{\underset{N}{\overset{}{\bigcirc}}}}\underset{CO_2H}{\overset{}{\underset{}{\bigcirc}}}CH_2OAc$$

| Ex. No. | R | R$^a$ | Method | [α]$_D$ (dioxan) | pH 6 λ$_{max}$ nm | ε | β-lactam ν$_{max}$ cm$^{-1}$ (solvent) | τ values for DMSO-d$_6$ at 100 MHz | | | Yield % |
|---|---|---|---|---|---|---|---|---|---|---|---|
| | | | | | | | | x | R$^a$ | y | |
| 75 | " | (CH$_3$–S furan) | B | +39.5° | 237<br>266<br>295.5 | 17,500<br>13,400<br>14,700 | 1786<br>(CHBr$_3$) | 0.34 | 4.75<br>2.36;2.81,2.96 | 4.18 | 79 |
| 76 | (pyrrole-CH$_2$-OCH$_2$Ph) | CH$_2$ | B | +39.5° | 268.5<br>289 | 13,200<br>12,900 | 1792<br>(CHBr$_3$) | 0.30 | 6.18 | 4.15 | 76 |

EXAMPLE 77

3-(1-Methyltetrazol-5-ylthiomethyl)-7β-[2-phenoxyimino-2-phenylacetamido]-ceph-3-em-4-carboxylic acid (syn-isomer)

A suspension of 2-phenoxyimino-2-phenylacetic acid (464 mg) in dry methylene dichloride (25 ml) was added, over 5 minutes, to a stirred solution of diphenylmethyl 7β-amino-3-(1-methyltetrazol-5-ylthiomethyl)-ceph-3-em-4-carboxylate (989 mg) and dicyclohexylcarbodiimide (454 mg) in methylene dichloride (25 ml). After stirring for a further 2 hours, the solvent was evaporated in vacuo; the residue was suspended in ethyl acetate (60 ml), the insoluble material filtered off, and the filtrate washed with saturated sodium bicarbonate:-water = 1:1, water, and brine (30 ml of each), dried, and evaporated to a foam (1.56 g). A solution of this foam in benzene (10 ml) was purified by chromatography on kieselgel (60 g), with benzene-ethyl acetate = 10:1 as eluant. Appropriate fractions were combined and evaporated to dryness in vacuo to give diphenylmethyl 3-(1-methyltetrazol-5-ylthiomethyl)-7β-[2-phenoxyimino-2-phenylacetamido]ceph-3-4-carboxylate (syn-isomer) was an orange foam (1.16 g, 87%). A solution of this foam in a mixture of trifluoroacetic acid (4 ml) and anisole (1 ml) was kept at 23° for 5 minutes, and the solvents were removed at 40° (2 mm). The residue was suspended in ether (80 ml), saturated sodium bicarbonate:water = 1:3 (120 ml) was added, and the mixture was stirred until all the solid had dissolved (ca. 10 minutes). The aqueous phase was separated, covered with ethyl acetate (150 ml), and acidified to pH 2 with 2N-hydrochloric acid. The organic phase was separated, washed with water, and brine (50 ml of each), and the solvent evaporated in vacuo. The residue was dissolved in acetone (50 ml), the solution stirred for 5 minutes with charcoal (ca. 1 g), and the mixture filtered through a pad of kieselguhr. The filtrate was dried and evaporated to a foam (780 mg), which was dissolved in ethyl acetate, and the solution run into petroleum ether to give the title acid as a colourless, amorphous solid (640 mg, 63.3%); [α]$_D^{23}$ − 64° (c 1.01, acetone); λ$_{max}$ (0.1 M -pH 6 phosphate buffer) 261 nm. (ε 19,200); τ (DMSO-d6) values include-0.11 (NH, d, J 8 Hz.), 4.00 (7-H, dd, J 5 and 8 Hz.), 4.70 (6-H, d, J 5 Hz), and 6.04 (C$\underline{H}_3$—).

EXAMPLES 78–93

General Procedures for the Preparation of 7β-(2-substituted oxyimino-2-arylacetamido)-3-(substituted)-ceph-3-em-4-carboxylic acids using Dicyclohexylcarbodiimide (i) to a solution of a t-butyl (Example 93) or diphenylmethyl ester of 7β-amino-3-(substituted)-ceph-3-em-4-carboxylic acid (1 equiv.) and dicyclohexylcarbodiimide (1–1.2 equiv.) in dry methylene chloride was added at 0°–20°, a solution of the syn-2-alkoxy- or 2-aryloxyimino-2-arylacetic acid (1 equiv.) in dry methylene chloride. After stirring for 45 min.–3hr. at room temperature the mixture was filtered and the filtrate was evaporated to dryness. The residue in ethyl acetate was washed successively with sodium bicarbonate solution, water and brine. The organic phase was dried and evaporated to a foam or solid. The resulting ester was purified by crystallisation or chromatography on silica and characterised by p.m.r. and thin layer chromatography.

Where the 7β-amino starting material was available as its p-toluene sulphonic acid salt (Example 92) the free base was liberated by shaking with ethyl acetate and an excess of saturated sodium bicarbonate solution. After washing with water and brine the organic layer was evaporated to dryness and the free amine was redissolved in methylene chloride.

(ii) The intermediate esters so derived were deprotected by dissolving in a mixture of trifluoroacetic acid (3–10 ml/1g of ester) and anisole (1–5ml/1g of ester) and left at room temperature for 5–10 min. When the solvents were removed by evaporation under reduced pressure. The crude acid was shaken with ether or ethyl acetate and an excess of aqueous sodium bicarbonate and the aqueous layer was washed with ethyl acetate. The aqueous phase was separated, covered with ethyl acetate and acidified to pH 1–2 with 2N-hydrochloric acid. The organic layer was washed, dried and evaporated to give the required syn-7β-(2-alkoxy- or 2-aryloxy-2-arylacetamido)3-(substituted)-ceph-3-em-4-carboxylic acid, the compounds so obtained being listed in Table 6.

(iii) Diphenylmethyl 7β-Amino-3-(1-ethyltetrazol-5-yl-thiomethyl)-ceph-3-em-4-carboxylate (used as Starting Material for Example 79)

(a) Diphenylmethyl 3-(1-ethyltetrazol-5-ylthiomethyl)7β-(2-thienylacetamido)-ceph-3-em-4-carboxylate A solution of diphenylmethyl 3-bromomethyl-7β-(2-thienylacetamido)-ceph-3-em-4-carboxylate (11.67 g) and 1-ethyltetrazoline-5-thione (2.6 g) in dry tetrahydrofuran (150 ml) was stirred at 0° and a solution of triethylamine (2.8 ml) in tetrahydrofuran (25 ml) was added, dropwise, over 5 minutes. The resulting suspension was stirred for a further 25 minutes, during which time the temperature was allowed to rise to ca. 20°, and was then added, over 5 minutes, to a stirred mixture of 2N-hydrochloric acid (50 ml), water (350 ml), brine (350 ml), and ethyl acetate (600 ml). The organic phase was separated, and washed with 2N-hydrochloric acid, saturated sodium bicarbonate, water, and brine, and dried and evaporated to a foam (11.71 g). A solution of this foam in benzene (25 ml) was purified by chromatography on kieselgel (200 g), with benzene:ethyl acetate = 5:1 as eluant. Appropriate fractions were combined and the solvents evaporated in vacuo. The residue was dissolved in methylene dichloride, and the solution run into petroleum ether to give the ester as a pale-yellow, amorphous solid (8.585g, 68%); $[\alpha]_D^{23} - 131°$ (c 0.97. CHCl$_3$); $\lambda_{max}$ (EtOH) 264 nm ($\epsilon$ 7,300), $\tau$ (CDCl$_3$) values include 4.12 (7-H, dd, J 5 and 9 Hz.), 5.04 (6-H, d, J 5 Hz.), 5.83 (CH$_3$C$\underline{H}_2$—, q, J 7 Hz.), and 8.57 (C$\underline{H}_3$CH$_2$—, t, J 7 Hz.).

(b) A solution of pyridine (2.13 ml) in dry methylene dichloride (10 ml) was added, over 5 minutes, to a stirred suspension of phosphorus pentachloride (5.47 g) in methylene dichloride (20 ml). After 10 minutes, the suspension was cooled to 0°, and a solution of diphenylmethyl 3-(1-ethyltetrazol-5-yl-thiomethyl)-7β-(2-thienylacetamido)-ceph-3-em-4-carboxylate (8.3 g) in methylene dichloride (40 ml) was added, dropwise, over 10 minutes. The resulting solution was stirred for a further 1 hour, during which time the temperature was allowed to rise to ca. 23°, and then added, over 10 minutes, to a stirred and cooled (0°) mixture of methanol (30 ml) and methylene dichloride (60 ml). After 15 minutes, N-hydrochloric acid (50 ml) was added, and stirring continued for a further 10 minutes. The organic phase was separated, stirred for 30 minutes with saturated sodium bicarbonate (200 ml), and washed with saturated sodium bicarbonate and brine and treated with some charcoal. The suspension was filtered through a kieselguhr pad, the filtrate dried and evaporated to an oily solid (7.47 g). This material was triturated with ethyl acetate (15 ml) to give the amine as a pale-yellow solid (3.854 g, 58%); $[\alpha]_D^{23} - 213°$ (c. 1.14, CHCl$_3$); $\lambda_{max}$ (CHCl$_3$)265nm. ($\epsilon$ 7,900); 268.5 nm. ($\epsilon$ 7,900) and 279.5nm ($\epsilon$ 7,800); $\tau$ (DMSO-d6) values include 4.92 (d, J 5 Hz.) and 5.11 (d, J 5 Hz.), (6-H and 7H), and 5.72 (q, J 7 Hz.) and 8.61 (t, J 7Hz.), (CH$_3$CH$_2$—).

(iv) Diphenylmethyl 7β-Amino-3-(6-nitrobenzothiazol-2-ylthiomethyl)-ceph-3-em-4-carboxylate, hydrochloride (used as Starting Material for Examples 81 and 85).

A solution of diphenylmethyl 3-bromomethyl-7β-formamidoceph-3-em-4-carboxylate, 1β-oxide (10.068 g) and 2-mercapto-6-nitrobenzothiazole (4.244 g) in dry N,N-dimethylformamide (125 ml) was stirred at 0°; a solution of triethylamine (3.2 ml) in N,N-dimethylformamide (25 ml) was added, dropwise, over 5 minutes, and stirring continued for a further 2 hours, during which time the temperature was allowed to rise to ca. 23°. The solvent was removed at 40° (2 mm.); the residue was partitioned between methylene dichloride (300 ml) and water (300 ml), and the organic phase washed with 2N-hydrochloric acid, water, and brine and dried and evaporated to a foam (14.35 g), A solution of this foam in dry methylene dichloride (200 ml) was stirred at −20°, a solution of phosphorus tribromide (2.5 ml, ca 1.5 equiv.) in methylene dichloride (25 ml) was added, dropwise, over 5 minutes, and stirring continued for a further 30 minutes at −10° to −15°. The resulting solution was stirred for 30 minutes with saturated sodium bicarbonate (250 ml); the organic phase was separated, and washed with saturated sodium bicarbonate and brine and treated with some charcoal. The suspension was filtered through a kieselguhr pad, and the filtrate dried and evaporated to a foam (10.71 g). A suspension of this foam in methanol (200 ml) was stirred at 0°; phosphorus oxychloride (3.66 ml — 2 equivs.) was added, over 2 minutes, and stirring continued for a further 2 hours at ca. 23°, during which time the solid all dissolved. The solvent was evaporated off, ethyl acetate (100 ml) was added, and the resulting suspension evaporated to dryness in vacuo. The residual gum was dissolved in methylene dichloride (100 ml); the solution was stirred at 0° and ether (300 ml) was added, over 5 minutes. The precipitate was filtered off, and washed with ether (100 ml), and dried in vacuo to give the hydrochloride as pale-yellow flakes (9.744 g, 78%); $[\alpha]_D^{23} - 94°$ (c 1.0, DMSO); $\lambda_{max}$) (EtOH) 328 nm. ($\epsilon$ 13,400); $\tau$ (DMSO-d6) values include 4.72 (6H and 7-H), 5.10 and 5.57 (3-CH$_2$, q. J 14 Hz.), and 6.10 (2 CH$_2$).

(v) Diphenylmethyl 7β-Amino-3-(6-nitrobenzothiazol-2-ylthiomethyl)-ceph-3-em-4-carboxylate A solution of the hydrochloride described above (910 mg) in methylene dichloride (50 ml) was stirred for 30 minutes with saturated sodium bicarbonate (50 ml). The organic phase was separated, and washed with saturated sodium bicarbonate and brine and treated with some charcoal. The suspension was filtered through a kieselguhr pad, and the filtrate dried and evaporated to a foam (660 mg). This material was digested with methanol (50 ml) to give the amine as a pale-yellow solid (432 mg,50%); $[\alpha]_D^{20} - 195°$ (c 1.01, CHCl$_3$); $\lambda_{max}$ (CHCl$_3$) 251 nm. ($\epsilon$ 14,500) and 334 nm. ($\epsilon$ 16,800), $\tau$ (CDCl$_3$) values include 5.04 and 5.22 (doublets, J 5 Hz., 6-H and 7-H), and 7.96 (NH$_2$).

TABLE 3

Structure: R-C(=NOR^a)-CONH-(x)-[β-lactam with (y)H]-...-Y, with CO₂H

| Ex. No. | R | R^a | Y | $[\alpha]_D$ (acetone) | pH 6 $\lambda_{max}$ nm | $\epsilon$ | β-lactam $\nu_{max}$ (Solvent) | τ values for DMSO-d₄ at 100 MHz: X | R^a | Y | Yield* % |
|---|---|---|---|---|---|---|---|---|---|---|---|
| 78 | thienyl | C(CH₃)₂ | CH₂·S-(1-methyltetrazol-5-yl) | −89° | 268.5 | 15,900 | 1786 (Nujol) | 0.26 | 8.69 | 6.05 (CH₃) | 57 |
| 79 | " | C(CH₃)₂ | CH₂S-(1-ethyltetrazol-5-yl) | −96° | 268.5 | 18,200 | 1782 (Nujol) | 0.36 | 8.67 | 5.66;8.56 (C₂H₅) | 19 |
| 80 | " | C(CH₃)₃ | CH₂S-(2-phenyl-1,3,4-oxadiazol-5-yl) | −110° | 279 | 31,800 | 1788 (CHBr₃) | 0.27 | 8.70 | 2.0;2.36 (Ph) | |
| 81 | " | C(CH₃)₃ | CH₂S-(4-nitrobenzothiazol-2-yl) | −178° | 293.5 (EtOH) | 20,200 | 1780 (Nujol) | 0.33 | 8.72 | 0.93 1.67;1.97 (Ar) | 32 |
| 82 | furyl | C(CH₃)₃ | CH₂·S-(1-methyltetrazol-5-yl) | −95° | 277.5 | 21,200 | 1780 (Nujol) | 0.32 | 5.69 | 6.05 (CH₃) | 35 |
| 83 | thienyl | cyclopentyl | " | −78° | 271 | 18,100 | 1782 (Nujol) | 0.30 | 522; 8.25 | 6.00 (CH₃) | 59 |
| 84 | furyl | " | CH₃S-(1-methyltetrazol-5-yl) | −80° | 279 | 22,300 | 1780 (Nujol) | 0.29 | 5.22; 8.27 | 6.0 (CH₃) | 46 |
| 85 | " | " | CH₂S-(4-nitrobenzothiazol-2-yl) | −153° | 280.5 | 17,400 | 1780 (Nujol) | 0.30 | 3.25; 8.30 | 0.91 1.64 and 1.95 (Ar) | 24 |
| 86 | Ph | C₂H₅ | CH₂S-(1-methyltetrazol-5-yl) | −93° | 262 | 19,600 | 1782 (Nujol) | 0.24 | 5.79; 8.72 | 6.05 (CH₃) | 48 |
| 87 | thienyl | C(CH₃)₃ | CH=CH₂ | −47° | 292 (EtOH) | 17,200 | 1764 (CHBr₃) | 0.29 | 8.66 | 2.75 4.68 4.9 | 54 |
| 88 | Ph | C₂H₅ | CH=CH₂ | −77° | 276 | 19,200 | 1782 (CHBr₃) | 0.19 | 5.78; 8.70 | 3.01 4.35 4.64 | 47 |
| 89 | benzothienyl | C(CH₃)₃ | CH=CH₂ | −49° | 232 287.5 297 (EtOH) | 24,900 19,800 18,900 | 1764 (CHBr₃) | 0.32 | 8.57 | 2.75 4.69 4.93 | 60 |
| 90 | thienyl | C(CH₃)₃ | CH₂OCOCH=CHCH₃ | +44° (DMSO) | 260 | 15,000 | 1788 (Nujol) | 0.32 | 8.70 | 3.04; 4.07 8.14 | 50 |
| 91 | Ph | C₂H₅ | CH₂SCOCH₃ | −64° (DMSO) | 260 | 18,600 | 1780 (Nujol) | 0.27 | 5.78 8.73 | 7.64 (CH₃) | 64 |

TABLE 3-continued

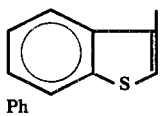

| Ex. No. | R | $R^a$ | Y | $[\alpha]_D$ (acetone) | pH 6 $\lambda_{max}$ nm | $\epsilon$ | β-lactam $\nu_{max}$ (Solvent) | τ values for DMSO-$d_4$ at 100 MHz | | | Yield* % |
|---|---|---|---|---|---|---|---|---|---|---|---|
| | | | | | | | | X | $R^a$ | Y | |
| 92 | [benzothiophene] | $C(CH_3)_3$ | $CH_2OCOCH=CHCH_3$ | +37.5° (DMSO) | 231.5 (EtOH) | 27,200 | 1790 (Nujol) | 0.28 | 8.56 | 3.0; 4.05 8.12 | 43 |
| 93 | Ph | $CH_2CO_2H$ | $CH_2OCOCH_3$ | +40° (dioxan) | 257 | 17,100 | 1780 (Nujol) | 0.26 | 5.30 ($CH_3$) | 7.96 ($CH_3$) | 32 |

*Yields are given as overall yields for the coupling and deprotection reactions [stages (i) and (ii) above].

EXAMPLE 94

3-(5-Methyl-1,3,4-thiadiazol-2-yl)thiomethyl-7β-[2-(then-2-yl)oxyimino-2-(thien-2-yl)-acetamido]-ceph-3-em-4-carboxylic acid (syn-isomer)

A solution of syn-then-2-yloxyiminothien-2-yl-acetic acid (715 mg) in methanol (20 ml) was neutralised with 0.32 N sodium methoxide solution (8.7 ml). The solvent was removed in vacuo, and the residual sodium salt dried by azeotroping with benzene (2 × 20 ml). Oxalyl chloride (685 mg) was added to a suspension of the above salt in benzene (30 ml) containing N,N-dimethylformamide (1 drop). The resulting solution was stirred at 20° for 1.5 hr, and evaporated to dryness in vacuo to give the acid chloride.

A solution of this acid chloride in acetone (20 ml) was added dropwise to a stirred solution of 7β-amino-3-(5-methyl-b 1,3,4-thiadiazol-2-yl)-thiomethylceph-3-em-4-carboxylic acid hydrochloride (1.00 g) in water (30 ml) containing sodium bicarbonate (660 mg), at 0°. The mixture was stirred for 2 hr. and allowed to reach room temperature. The acetone was removed in vacuo and the solution acidified to pH 1.9. The solution was extracted with ethyl acetate (6 × 70 ml) and the combined extracts were washed with water, dried and evaporated to dryness. The crude product was washed with benzene cyclohexane (1:1, 2 × 20 ml) and cyclohexane and dried to give the title carboxylic acid (863 mg) $[\alpha]_D$ − 61° (c 1.44, DMSO), λHd max. (pH 6 buffer) 239 nm ($\epsilon$ 17,900), 273 nm ($\epsilon$ 19,150), $\lambda_{max}$ (Nujol) 1784 cm$^{-1}$ (β-lactam) τ (DMSO-$_6$) values include 0.09 (d, N$\underline{H}$), 4.68 (s, C$\underline{H}_2$-thienyl), 7.31 (s, C$\underline{H}_3$).

The sodium and potassium salts of the compounds of the Examples are prepared in conventional manner by reaction with sodium or potassium 2-ethylhexanoate respectively. To illustrate such salt preparation the formation of sodium 3-acetoxymethyl-7β-(2-methoxyimino-2-phenylacetamido)ceph-3-em-4-carboxylate (syn-isomer) is described in more detail below.

EXAMPLE 95

Syn-3-acetoxymethyl-7β-(2-methoxyimino-2-phenylacetamido)ceph-3-em-4-carboxylic acid (10.84 g.), was dissolved in the minimum amount of ethyl acetate (280 ml.) and a 1M solution of sodium ethyl hexanoate (25 ml.) was added dropwise to the stirred solution, which was stirred for 20 minutes, and cooled at 0° for 2 hours. The precipitated salt was removed by filtration, and stirred with ethyl acetate (100 ml.) for 2 hours, and the solid (9.6 g.) filtered, washed and dried. This was then stirred with ether (2 × 200 ml.) at room temperature for 30 minutes, producing the title compound (8.9 g., 78%), $[\alpha]_D^{22}$ + 60° (c, 1.06 in water), $\lambda_{max}$ (pH 6 buffer) 258–259 nm ($\epsilon$ 19,150).

The following example illustrates the preparation of an amine base salt, such salts otherwise being prepared conveniently from the appropriate amine.

EXAMPLE 96

Diethanolammonium 3-Acetoxymethyl-7β-(2-phenoxyimino-2-phenylacetamido)-ceph-3-em-4-carboxylate (syn-isomer)

To a stirred solution of crude syn-3-acetoxymethyl-7β-(2-phenoxyimino-2-phenylacetamido)ceph-3-em-4-carboxylic acid (prepared as in Example 66) (5.94 g) in 2-propanol (30 ml) was added a solution of diethanolamine (3.8 ml) in 2-propanol (8 ml). The precipitated solid was collected, washed (2-propanol, then ether), and dried in vacuo to give the title compound (3.43 g), m.p. 139.5°; τ values (DMSO-d6) include −0.06 (d) (NH), 4.13 (dd) (7-H), 4.78 (d) (6-H), 6.96 and 7.96 (—CH$_2$—CH$_2$—).

The following Examples illustrate the formulation of pharmaceutical preparations.

EXAMPLE A

Dry Powder for Injection

Sterile sodium 3-acetoxymethyl-7β-(2-methoxyimino-2-phenylacetamido)ceph-3-em-4-carboxylate (syn-isomer) powder is filled into glass vials so that the glass vials contain 500 mg. and 1.0 g of the antibiotic as desired. Filling is carried out aseptically under a blanket of nitrogen. The vials are closed using rubber discs held in position by aluminum sealing rings, thereby preventing gaseous exchange or ingress of microorganisms. The product is intended for reconstitution woth water for injections or other suitable sterile vehicle shortly before administration.

EXAMPLE B

Intramammary Infusion for Cattle

| Percentage composition (w/w) | |
|---|---|
| Sodium 3-acetoxymethyl-7β-(2-ethoxyimino-2-phenylacetamido)-ceph-3-em-4-carboylate (syn-issomer) | 10.00 |
| Vehicle to: | 100.00 |

-continued

| Vehicle: Tween 60 | 3.00 |
| --- | --- |
| White Beeswax | 6.00 |
| Arachis Oil | 91.00 |

The last three ingredients are heated together at 150° C for 1 hour and then cooled to room temperature with stirring. The sterile antibiotic powder is added aseptically to this vehicle and the product refined with a high speed stirrer. The preparation is filled aseptically into sterile collapsible aluminium tubes so that each tube contains 3.0 g of the preparation comprising 300 mg. of the cephalosporin derivative.

EXAMPLE C

Dry Blend for an Oral Syrup

| Sodium 3-acetoxymethyl-7-β(2-methoxyimino-2-thien-2'-ylacetamido)ceph-3-cm-4-carboxylate (sym isomer) | 5.00 g. |
| --- | --- |
| Sodium Saccharin | 0.10 g. |
| Sodium Citrate (anhydrous) | 1.00 g. |
| Citric Acid (anhydrous) | 0.10 g. |
| Amoranth | 0.01 g. |
| Spray-dried Raspberry Flavour | 1.00 g. |
| Sucrose to | 75.00 g. |

The product is intended for reconstitution with sufficient purified water to give a final volume of 100 ml., which should all be administered with a few days, each 5 ml. dose of syrup containing 250 mg. of the cephalosporin derivative.

In order to prepare the blend, the amaranth is intimately mixed with some of the sodium citrate and milled. The sodium saccharin and citric acid are blended together. They are mixed thoroughly with the colour triturate, then with the remainder of the sodium citrate, flavour and antibiotic powder in that order. This blend is milled, mixed with sucrose and then 75 g. is filled into each of a number of 150 ml. capacity bottles, which are closed with moisture-proof screw caps.

EXAMPLE D

(a) Oral Capsules

Sodium 3-acetoxymethyl-7β-(2-ethoxyimino-2-phenylacetamido)ceph-3-em-4-carboxylate (syn-isomer) is blended with 1 percent magnesium stearate and filled into size 0 hard gelatin capsules, each capsule containing a claimed dose of 250 mg. of the cephalosporin antibiotic. The capsules are packed in glass vials with plastic caps giving a moisture-proof seal.

We claim:

1. A compound selected from the group consisting of a highly active cephalosporin antibiotic highly stable to β-lactamases, having the formula

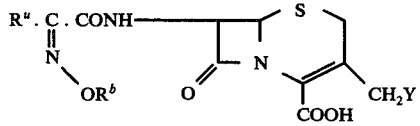

wherein $R^u$ is phenyl or naphthyl or each of these groups substituted by chloro, bromo, iodo, fluoro, hydroxy, lower alkyl, nitro, amino, loweralkylamino, diloweralkylamino, lower alkanoyl, lower alkanoylamino, lower alkoxy, lower alkylthio or carbamoyl;

$R^b$ is lower alkyl or cycloalkyl containing 3-7 carbon atoms;

Y is a group of formula $-OCO.NH(CH_2)_mD$ wherein m is an integer from 1-4 and D is chlorine, bromine, iodine or fluorine, said cephalosporin antibiotic being in the form of a syn isomer free of the corresponding anti isomer to the extent of at least 75% based on the total weight of said antibiotic; and a physiologically acceptable salt thereof.

2. A compound of claim 1 which is 3-(2-chloroethylcarbamoyloxymethyl)-7β-(2-methoxyimino-2-phenylacetamido)ceph-3-em-4-carboxylic acid (syn isomer).

* * * * *